(12) United States Patent
Gharat et al.

(10) Patent No.: US 7,943,634 B2
(45) Date of Patent: May 17, 2011

(54) SUBSTITUTED BENZO[4,5]FURO[3,2-C]PYRIDINE DERIVATIVES AS PDE 4 INHIBITORS

(75) Inventors: Laxmikant Atmaram Gharat, Thane (IN); Balasubramanian Gopalan, Mumbai (IN); Neelima Khairatkar Joshi, Thane (IN)

(73) Assignee: Glenmark Pharmaceuticals S.A., La Chaux de-Fonds (CH)

( * ) Notice: Subject to any disclaimer, the term of this patent is extended or adjusted under 35 U.S.C. 154(b) by 333 days.

(21) Appl. No.: 11/721,912

(22) PCT Filed: Dec. 15, 2005

(86) PCT No.: PCT/IB2005/003798
§ 371 (c)(1),
(2), (4) Date: Aug. 25, 2009

(87) PCT Pub. No.: WO2006/064355
PCT Pub. Date: Jun. 22, 2006

(65) Prior Publication Data
US 2009/0306082 A1    Dec. 10, 2009

Related U.S. Application Data

(60) Provisional application No. 60/637,232, filed on Dec. 17, 2004.

(30) Foreign Application Priority Data

Dec. 17, 2004  (IN) .................. 1352/MUM/2004

(51) Int. Cl.
*A61K 31/44* (2006.01)
(52) U.S. Cl. .................. 514/291; 546/89; 546/284.1
(58) Field of Classification Search .................. 514/291; 546/89, 284.1
See application file for complete search history.

(56) References Cited

U.S. PATENT DOCUMENTS

| | | | |
|---|---|---|---|
| 3,759,948 | A | 9/1973 | Shen et al. |
| 3,846,553 | A | 11/1974 | Shen et al. |
| 4,222,944 | A | 9/1980 | Berger et al. |
| 5,814,651 | A | 9/1998 | Duplantier et al. |
| 6,110,962 | A | 8/2000 | Wrobel et al. |
| 6,131,566 | A | 10/2000 | Ashurst et al. |
| 6,228,346 | B1 | 5/2001 | Zhang et al. |
| 6,273,086 | B1 | 8/2001 | Ohki et al. |
| 6,402,733 | B1 | 6/2002 | Daugherty |
| 7,223,789 | B2 | 5/2007 | Gopalan et al. |
| 2002/0128290 | A1 | 9/2002 | Ohshima et al. |
| 2006/0178418 | A1 | 8/2006 | Balasubramanian et al. |
| 2007/0105854 | A1 | 5/2007 | Gopalan et al. |
| 2007/0105855 | A1 | 5/2007 | Gopalan et al. |

FOREIGN PATENT DOCUMENTS

| | | |
|---|---|---|
| EP | 0497564 | 8/1992 |
| EP | 1270577 | 1/2003 |
| GB | 1041861 | 9/1966 |
| GB | 1285398 | 8/1972 |
| GB | 1289187 | 9/1972 |
| JP | 62158253 | 7/1987 |
| JP | 63014156 | 1/1988 |
| WO | 9210476 | 6/1992 |
| WO | 9319747 | 10/1993 |
| WO | 9402465 | 2/1994 |
| WO | 94/08995 | 4/1994 |
| WO | 9420446 | 9/1994 |
| WO | 9501338 | 1/1995 |
| WO | 9504046 | 2/1995 |
| WO | 9509837 | 4/1995 |
| WO | 9520578 | 8/1995 |
| WO | 9524381 | 9/1995 |
| WO | 9603377 | 2/1996 |
| WO | 98/09934 | 3/1998 |
| WO | 9947545 | 9/1999 |
| WO | 9958521 | 11/1999 |
| WO | 0127107 | 4/2001 |
| WO | 0170673 | 9/2001 |
| WO | 0170746 | 9/2001 |
| WO | 02/060867 | 8/2002 |
| WO | 02/072567 | 9/2002 |

(Continued)

OTHER PUBLICATIONS

Koyama, et al., Heterocycles 1981; 16(6):969-972.

(Continued)

*Primary Examiner* — James O Willis
*Assistant Examiner* — Douglas M Willis
(74) *Attorney, Agent, or Firm* — Blank Rome LLP

(57) ABSTRACT

The present invention relates to novel Phosphodiesterase type 4 (PDE4) inhibitors of the formula (1) and analogs, tautomers, enantiomers, diasteromers, regioisomers, stereoisomers, polymorphs, pharmaceutically acceptable salts, appropriate N-oxides, pharmaceutically acceptable solvates thereof and the pharmaceutical compositions containing them which are useful in the treatment of allergic and inflammatory diseases including asthma, chronic bronchitis, atopic dermatitis, urticaria, allergic rhinitis, allergic conjunctivitis, vernal conjunctivitis, eosinophilic granuloma, psoriasis, rheumatoid arthritis, septic shock, ulcerative colitis, Crohn's disease, reperfusion injury of the myocardium and reperfusion injury of the brain, chronic glomerulonephritis, endotoxic shock and adult respiratory distress syndrome.

15 Claims, No Drawings

FOREIGN PATENT DOCUMENTS

| | | |
|---|---|---|
| WO | 04016596 | 2/2004 |
| WO | 04022536 | 3/2004 |
| WO | 2004/037805 | 5/2004 |
| WO | 2004/069831 | 8/2004 |
| WO | 2004/089940 | 10/2004 |

OTHER PUBLICATIONS

Hulme, et al., Bioorganic and Medicinal Chemistry Letters 1998; 8:175-178.

Silvestre, et al., Drugs of the Future 1998; 23(6):607-615.

Fox et al. "Design, Synthesis, and Preliminary Pharmacological Evaluation of N-Acyl-3-aminoglutarimides as Broad-Spectrum Chemokine Inhibitors in Vitro and Anti-inflammatory Agents in Vivo." J. Med. Chem. 2002; 45(2):360-370.

Rogers, D.F., Giembycz, M.A., *Trends Pharmacol. Sci.* 1998; 19:160-164.

Barnes, P.J., *Trends Pharmacol. Sci.* 1998; 19:415-423.

Soderling, S.H., Bayuga, S.J., and Beavo, J.A., *Proc. Natl. Acad. Sci.*, USA 1999; 96:7071-7076.

Fujishige, K, Kotera, J., Michibata, H., Yuasa, K., Takebayashi, Si, Okamura, K. and Omori, K., *J. Biol. Chem.*1999; 274:18438-18445.

Trophy,T. J., *Am. J. Respir. Crit. Care Med.* 1998; 157: 351-370.

*Nature Medicine* 1995; 1:211-214.

*Nature Medicine* 1995; 1:244-248.

*British Journal of Pharmacology* 1999; 128:1393-1398.

Barnette, M.S., Grous, M., Cieslinsky, L.B., Burman, M., Christensen, S.B., Trophy, T J., *J. Pharmacol. Exp. Ther.* 1995; 273:1396-1402.

Zeller E. et. al., *Pharmacopsychiatr*,1984; 17:188-190.

Jacobitz, S., McLaughlin, M.M., Livi, G.P., Burman, M., Trophy, T.J., *Mol. Pharmaco.* 1996; 50:891-899.

Muller, T., Engels, P., Fozard, J.R., *Trends Pharmacol. Sci.* 1996; 17:294-298.

Hughes. B et.al., *Br. J. Pharmacol.* 1996; 118:1183-1191.

Newman et al., *Thorax* 1985; 40:671-676.

Berenberg, M., *J. Asthma* USA 1985; 22:87-92.

*Biochemistry* 1971; 10:311-316.

*Proc. Natl. Acad. Sci.* U.S.A. 1974; 71:3844-3848.

SUBSTITUTED BENZO[4,5]FURO[3,2-C]PYRIDINE DERIVATIVES AS PDE 4 INHIBITORS

CROSS-REFERENCE TO RELATED APPLICATIONS

This application is a national phase of PCT Application No. PCT/IB2005/003798, filed Dec. 15, 2005, which claims priority to Indian Provisional Application 1352/MUM/2004 filed on Dec. 17, 2004, and U.S. Provisional Application 60/637,232 filed on Dec. 17, 2004, both of which are incorporated herein by reference in their entirety.

FIELD OF THE INVENTION

The present invention relates to novel tricyclic phosphodiesterase type 4 (PDE4) inhibitors, and analogs, tautomers, enantiomers, diasteromers, regioisomers, stereoisomers, polymorphs, pharmaceutically acceptable salts, appropriate N-oxides, and pharmaceutically acceptable solvates thereof, pharmaceutical compositions containing them, and their use for treating conditions mediated by PDE-IV inhibition, such as asthma and chronic obstructive pulmonary disease (COPD).

BACKGROUND OF THE INVENTION

Airway inflammation characterizes a number of severe lung diseases including asthma and chronic obstructive pulmonary disease (COPD). Events leading to airway obstruction include edema of airway walls, infiltration of inflammatory cells into the lung, production of various inflammatory mediators and increased mucous production. The airways of asthmatic patients are infiltrated by inflammatory leukocytes, of which eosinophils are the most prominent component. The magnitude of asthmatic reactions is correlated with the number of eosinophils present in the lungs.

The accumulation of eosinophils is found dramatically in the lungs of asthmatic patients although there are very few in the lungs of a normal individual. They are capable of lysing and activating cells and destroying tissues. When activated, they synthesize and release inflammatory cytokines such as IL-1, IL-3, and TNF-α and inflammatory mediators such as PAF, LTD4 and related oxygen species that can produce edema and broncho-constriction. Tumor necrosis factor (TNF-α) is also known to be involved in the pathogenesis of a number of autoimmune and inflammatory diseases. Consequently, manipulation of the cytokine signaling or biosynthetic pathways associated with these proteins may provide therapeutic benefit in those disease states. It has been well demonstrated that TNF-α production in pro-inflammatory cells becomes attenuated by an elevation of intracellular cyclic adenosine 3',5'-monophosphate (cAMP). This second messenger is regulated by the phosphodiesterase (PDE) family of enzymes. The phosphodiesterase enzymes play an integral role in cell signaling mechanisms by hydrolyzing cAMP and cGP to their inactive 5' forms. Inhibition of PDE enzymes thus results in an elevation of cAMP and/or cGP levels and alters intracellular responses to extra cellular signals by affecting the processes mediated by cyclic nucleotides. Since eosinophilis are believed to be a critical proinflammatory target for asthma, identification of the expression of the PDE 4 gene family in eosinophils led to PDE 4 as a potential therapeutic target for asthma [Rogers, D. F., Giembycz, M. A., *Trends Pharmacol. Sci.,* 19, 160-164 (1998); Barnes, P. J., *Trends Pharmacol. Sci.,* 19, 415-423 (1998)].

The mammalian cyclic nucleotide phosphodiesterases (PDEs) are classified into ten families on the basis of their amino acid sequences and/or DNA sequence, substrate specificity and sensitivity to pharmacological agents [Soderling, S. H., Bayuga, S. J., and Beavo, J. A., *Proc. Natl. Acad. Sci., USA,* 96, 7071-7076 (1999); Fujishige, K, Kotera, J., Michibata, H., Yuasa, K., Takebayashi, Si, Okamura, K. and Omori, K., *J. Biol. Chem.,* 274, 18438-18445 (1999)]. Many cell types express more than one PDE and distribution of isoenzymes between the cells varies markedly. Therefore development of highly isoenzyme selective PDE inhibitors provides a unique opportunity for selective manipulation of various pathophysiological processes.

Phosphodiesterase type 4 (PDE4) is an enzyme which regulates activities in cells which lead to inflammation in the lungs. PDE4, a cAMP-specific and $Ca^{+2}$-independent enzyme, is a key isozyme in the hydrolysis of cAMP in mast cells, basophils, eosinophils, monocytes and lymphocytes. The association between cAMP elevation in inflammatory cells with airway smooth muscle relaxation and inhibition of mediator release has led to widespread interest in the design of PDE4 inhibitors [Trophy, T. J., *Am. J. Respir. Crit. Care Med.,* 157, 351-370 (1998)]. Excessive or unregulated TNF-α production has been implicated in mediating or exacerbating a number of undesirable physiological conditions such as osteoarthritis and other arthritic conditions, septic shock, endotoxic shock, respiratory distress syndrome and bone resorption diseases. Since TNF-α also participates in the onset and progress of autoimmune diseases, PDE4 inhibitors may find utility as therapeutic agents for rheumatoid arthritis, multiple sclerosis and Crohn's disease. [*Nature Medicine,* 1, 211-214 (1995) and ibid., 244-248].

Strong interest in drugs capable of selective inhibition of PDE 4 is due to several factors. Tissue distribution of PDE4 suggests that pathologies related to the central nervous and immune systems could be treated with selective PDE-4 inhibitors. In addition, the increase in intracellular cAMP concentration, the obvious biochemical consequence of PDE-4 inhibition, has been well characterized in immunocompetent cells where it acts as a deactivating signal.

Recently the PDE4 family has grown to include four subtypes—PDE4A to PDE4D, each encoded by a distinct gene (*British Journal of Pharmacology;* 1999; v. 128; p. 1393-1398).

It has been demonstrated that increasing cAMP levels within these cells results in suppression of cell activation, which in turn inhibits the production and release of pro-inflammatory cytokines such as TNF-α. Since eosinophils are believed to be a critical pro-inflammatory target for asthma, identification of the expression of the PDE-4 gene family in eosinophils led to the PDE-4 as a potential therapeutic target for asthma.

The usefulness of several PDE-4 inhibitors, unfortunately, is limited due to their undesirable side effect profile which include nausea and emesis (due to action on PDE-4 in the central nervous system) and gastric acid secretion due to action on PDE-4 in parietal cells in the gut. Barnette, M. S., Grous, M., Cieslinsky, L. B., Burman, M., Christensen, S. B., Trophy, T J., *J. Pharmacol. Exp. Ther.,* 273, 1396-1402 (1995). One of the earliest PDE-4 inhibitors, Rolipram™, was withdrawn from clinical development because of its severe unacceptable side effect profile. Zeller E. et. al., *Pharmacopsychiatr.,* 17, 188-190 (1984) which is herein incorporated by reference in their entirety. The cause of severe side effects of several PDE-4 inhibitor molecules in human clinical trials has recently become apparent.

There exist two binding sites on mammalian PDE-4 at which inhibitor molecules may bind. Also PDE-4 exists in two distinct forms which represent different conformations. They are designated as High affinity Rolipram binding site PDE-4H and Low affinity Rolipram binding site PDE-4L [Jacobitz, S., McLaughlin, M. M., Livi, G. P., Burman, M., Trophy, T. J., *Mol. Pharmaco.*, 50, 891-899 (1996)]. It was shown that certain side effects (vomiting and gastric acid secretion) are associated with inhibition of PDE-4H whereas some beneficial actions are associated with PDE-4L inhibition. It was also found that human recombinant PDE-4 exists in 4 isoforms A, B, C and D [Muller, T., Engels, P., Fozard, J. R., *Trends Pharmacol. Sci.*, 17, 294-298 (1996)]. Compounds having more PDE-4D isoenzyme selectivity over the A, B or C isoenzymes have been found to have fewer side effects than Rolipram [Hughes. B et. al., *Br. J. Pharmacol.* 1996, 118, 1183-1191]. Therefore, selective inhibitors of PDE-4 isozymes have therapeutic efficacy in the treatment of inflammatory diseases, such as asthma and other respiratory diseases, without the undesirable side effects of prior non-selective PDE-4 inhibitors.

Although several research groups all over the world are working to find highly selective PDE-4 isozyme inhibitors, so far success has been limited. Various compounds have shown PDE-4 inhibition.

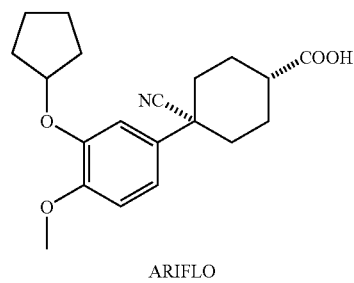

ARIFLO

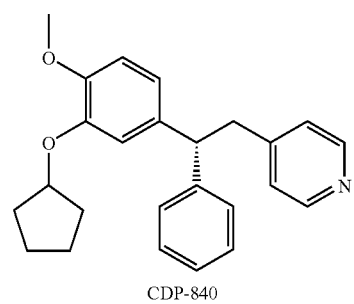

CDP-840

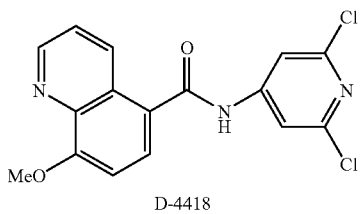

D-4418

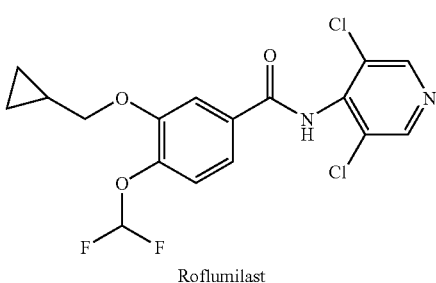

Roflumilast

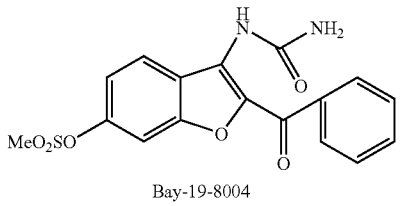

Bay-19-8004

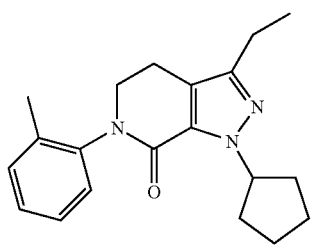

CP - 220,629

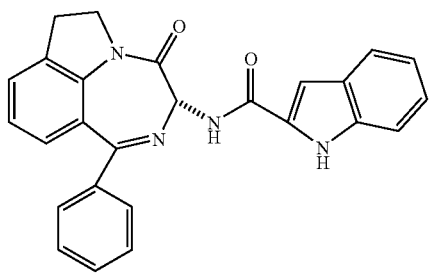

PD-168787

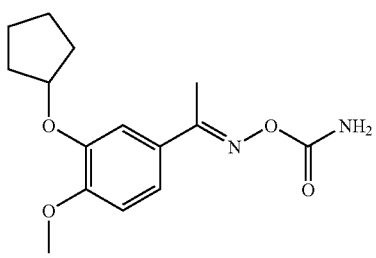

Filminast

SmithKline Beecham's "Ariflo" of the formula A, Byk Gulden's Roflumilast of the formula D and Bayer's Bay-19-8004 of the formula E have reached advanced stage of human clinical trials. Other compounds which have shown potent PDE-4 inhibitory activity include Celltech's CDP-840 of the formula B, Schering Plough's D-4418 of the formula C, Pfizer's 5CP-220,629 of the formula F, Parke Davis's PD-168787 of the formula G and Wyeth's Filminast of the formula H. However, it is believed that due to efficacy and side effects problems, Ariflo, CDP-840 and Bay-19-8004 were discontinued from clinical trials as a treatment for asthma. Other compounds of the formulae C and F are presently undergoing phase-1 clinical trials.

International Publication Nos. WO 2004/037805 and WO 2004/089940 disclose tricyclic compounds useful for the treatment of inflammatory and allergic disorders.

SUMMARY OF THE INVENTION

The present invention relates to new heterocyclic compounds which inhibit PDE-4 having the formula below:

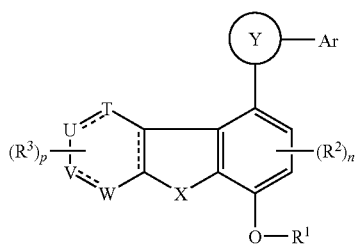

(1)

wherein each occurrence of $R^1$, $R^2$ and $R^3$ may be same or different and are independently hydrogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted aryl, substituted or unsubstituted arylalkyl, substituted or unsubstituted heteroaryl, substituted or unsubstituted heteroarylalkyl, substituted or unsubstituted heterocyclic group, substituted or unsubstituted heterocyclylalkyl, —$NR^5R^6$, —C(=L)-$R^5$, —C(O)—$R^5$, —C(O)O—$R^5$, —C(O)$NR^5R^6$, —S(O)$_m$—$R^5$, —S(O)$_m$—$NR^5R^6$, nitro, —OH, cyano, oxo, formyl, acetyl, halogen, —$OR^5$, —$SR^5$, or a protecting group, or when two $R^2$ or two $R^3$ substituents are ortho to each other, the two substituents may be joined to a form a 3-7 member optionally substituted saturated or unsaturated cyclic ring, which may optionally include up to two heteroatoms selected from O, $NR^5$ or S;

each occurrence of $R^5$ and $R^6$ may be same or different and are independently hydrogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted aryl, substituted or unsubstituted arylalkyl, substituted or unsubstituted heteroaryl, substituted or unsubstituted heteroarylalkyl, substituted or unsubstituted heterocyclic group, substituted or unsubstituted heterocyclylalkyl, nitro, halo, —OH, cyano, —C(O)—$R^a$, —C(O)O—$R^a$, —C(O)$NR^aR^b$, —S(O)$_m$—$R^a$, —S(O)$_m$—$NR^aR^b$, —C(=$NR^a$)—$R^b$, —C(=$NR^a$)—$NR^aR^b$, —C(=S)—$NR^aR^b$, —C(=S)—$R^a$, —N=C($R^aR^b$), $NR^aR^b$, —$OR^a$, —$SR^a$, or a protecting group or $R^5$ and $R^6$ may be joined together with the atom to which they are attached to form a 3-7 member optionally substituted saturated or unsaturated cyclic ring, which may optionally include up to two heteroatoms selected from O, $NR^a$ or S;

each occurrence of $R^a$ and $R^b$ may be same or different and are independently hydrogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted aryl, substituted or unsubstituted arylalkyl, substituted or unsubstituted heteroaryl, substituted or unsubstituted heteroarylalkyl, substituted or unsubstituted heterocyclic group, substituted or unsubstituted heterocyclylalkyl, nitro, —OH, cyano, formyl, acetyl, halogen, a protecting group, —C(O)—$R^a$, —C(O)O—$R^a$, —C(O)$NR^aR^b$, —S(O)$_m$—$R^a$, —S(O)$_m$—$NR^aR^b$, —$NR^aR^b$, —$OR^a$, or —$SR^a$;

Ar is substituted or unsubstituted aryl, substituted or unsubstituted arylalkyl, substituted or unsubstituted heterocyclic ring, substituted or unsubstituted heterocycloalkyl, substituted or unsubstituted heteroaryl ring, or substituted or unsubstituted heteroarylalkyl;

L is O, S or $NR^a$, where $R^a$ is as defined above;

n is an integer from 0 to 2;

p is an integer from 0 to 8;

T, U, V and W are each independently C, C=O, N, $NR^a$, O or S, with the proviso that at least one of T, U, V and W are N, $NR^a$, O or S, where $R^a$ is as defined above;

each dotted line [----] in the ring represents an optional double bond;

X is O, S(O)$_m$ or $NR^b$, where $R^b$ is as defined above;

each occurrence of m is independently 0, 1 or 2;

Y is —C(O)$NR^4$—, —$NR^4SO_2$—, —$SO_2NR^4$— or —$NR^4C(O)$—;

$R^4$ is hydrogen, substituted or unsubstituted alkyl, hydroxyl, —$OR^a$ (wherein $R^a$ is defined above), substituted or unsubstituted cycloalkyl, substituted or unsubstituted cycloalkylalkyl, substituted or unsubstituted aryl, substituted or unsubstituted arylalkyl, substituted or unsubstituted heterocyclic ring, substituted or unsubstituted heterocycloalkyl, substituted or unsubstituted heteroaryl ring or substituted or unsubstituted heteroarylalkyl, or an analog, tautomer, regioisomer, stereoisomer, enantiomer, diastereomer, polymorph, pharmaceutically acceptable salt, N-oxide, or pharmaceutically acceptable solvate thereof.

Further preferred is a compound according to Formula I wherein the substituents in the substituted alkyl, substituted alkenyl, substituted alkynyl, substituted cycloalkyl, substituted cycloalkylalkyl, substituted cycloalkenyl, substituted cycloalkenylalkyl, substituted arylalkyl, substituted aryl, substituted heteroaryl ring, substituted heteroarylalkyl, substituted heterocyclylalkyl ring, substituted cyclic ring, and substituted alkylcarbonyl may be the same or different and are selected from hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted amino, substituted or unsubstituted heteroaryl, substituted or unsubstituted heterocyclic ring, substituted heterocyclylalkyl ring, substituted or unsubstituted heteroarylalkyl, substituted or unsubstituted guanidine, —$COOR^x$, —C(O)$R^x$, —C(S)$R^x$, —C(O)$NR^xR^y$, —C(O)$ONR^xR^y$, —$NR^xCONR^yR^z$, —N($R^x$)$SOR^y$, —N($R^x$)$SO_2R^y$, —(=N—N($R^x$)$R^y$), —$NR^xC(O)OR^y$, —$NR^xR^y$, —$NR^xC(O)R^y$—, —$NR^xC(S)R^y$ —$NR^xC(S)NR^yR^z$, —$SONR^xR^y$—, —$SO_2NR^xR^y$—, —$OR^x$, —$OR^xC(O)$$NR^yR^z$, —$OR^xC(O)OR^y$—, —$OC(O)R^x$, —$OC(O)NR^xR^y$, —$R^xNR^yC(O)R^z$, —$R^xOR^y$, —$R^xC(O)OR^y$, —$R^xC(O)$$NR^yR^z$, —$R^xC(O)R^y$, —$R^xOC(O)R^y$, —$SR^x$, —$SOR^x$, —SO$_2$R$^x$, or —ONO$_2$, wherein R$^x$, R$^y$ and R$^z$ in each of the above groups can be hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted amino, substituted or unsubstituted aryl, substituted or unsubstituted heteroaryl, substituted heterocyclylalkyl ring, substituted or unsubstituted heteroarylalkyl, or substituted or unsubstituted heterocyclic ring.

Further preferred is a compound according to Formula I wherein Ar is optionally substituted phenyl, optionally substituted pyridyl or optionally substituted pyridyl-N-oxide in which the one or more optional substituents may be same or different and are independently hydrogen, hydroxyl, halogen, cyano, nitro, carboxyl, trifluoroalkyl, substituted or unsubstituted alkyl, substituted or unsubstituted alkoxy, substituted or unsubstituted alkoxycarbonyl, substituted or unsubstituted alkylcarbonyl, substituted or unsubstituted alkylcarbonyloxy, substituted or unsubstituted amino or mono or di substituted or unsubstituted alkylamino.

Further preferred is a compound according to Formula I wherein Ar is

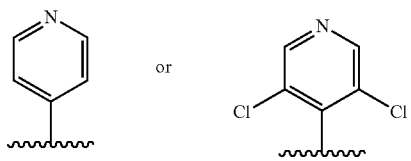

Further preferred is a compound according to Formula I wherein U and V are both N and T and W are both C.

Further preferred is a compound according to Formula I wherein T and V are both N and U and W are both C.

Further preferred is a compound according to Formula I wherein T, V, and W are C and U is N.

Further preferred is a compound according to Formula I wherein T, V, and W are C and U is NR$^a$.

Further preferred is a compound according to Formula I wherein T, U, and W are C and V is NR$^a$.

Further preferred is a compound according to Formula I wherein T and U are C, V is NR$^a$, and W is C(═O).

Further preferred is a compound according to Formula I or any of the aforementioned preferred embodiments where T, U, V, or W is NR$^a$, where R$^a$ is hydrogen. More preferably, T and W are not NR$^a$.

Further preferred is a compound according to Formula I or any of the aforementioned preferred embodiments where T, U, V, or W is NR$^a$, where R$^a$ is methyl. More preferably, T and W are not NR$^a$.

Further preferred is a compound according to Formula I or any of the aforementioned preferred embodiments where T, U, V, or W is NR$^a$, where R$^a$ is —COO-t-Butyl (tert-butyloxy carbonyl). More preferably, T and W are not NR$^a$.

Further preferred is a compound according to Formula I or any of the aforementioned preferred embodiments where T, U, V, or W is NR$^a$, where R$^a$ is —COOEt. More preferably, T and W are not NR$^a$.

Further preferred is a compound according to Formula I where X is O.

Further preferred is a compound according to Formula I where X is S(O)$_m$ wherein m is 0.

Further preferred is a compound according to Formula I where X is NR$^b$.

Further preferred is a compound according to Formula I where X is NR$^b$, where R$^b$ is methyl.

Further preferred is a compound according to Formula I where X is NR$^b$, where R$^b$ is cyclopropylmethyl.

Further preferred is a compound according to Formula I where X is NR$^b$, where R$^b$ is benzyl.

Further preferred is a compound according to Formula I where R$^1$ is substituted or unsubstituted alkyl.

Further preferred is a compound according to Formula I where R$^1$ is —CH$_3$.

Further preferred is a compound according to Formula I where R$^1$ is —CHF$_2$.

Further preferred is a compound according to Formula I where n is 0.

Further preferred is a compound according to Formula I where p is 0.

Further preferred is a compound according to Formula I where Y is —C(O)NH—.

According to one preferred embodiment, the compound has the formula

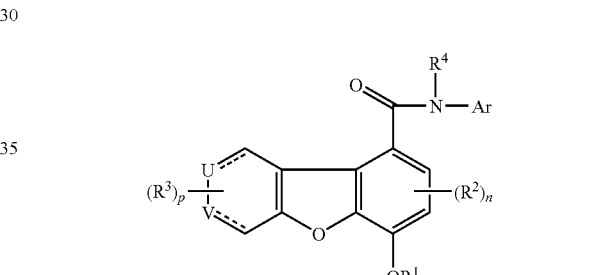

wherein

U and V are each independently C, N, or NR$^a$ (where R$^a$ is as defined above), with the proviso that at least one of U and V is N or NR$^a$;

both dotted lines represent double bonds or both dotted lines are absent;

each occurrence of R$^1$, R$^2$ and R$^3$ may be same or different and are as defined above; and Ar, R$^4$, n, and p are as defined above, or a pharmaceutically acceptable salt thereof.

According to a more preferred embodiment, n and p are 0, R$^1$ is substituted or unsubstituted alkyl (preferably CH$_3$ or CHF$_2$), and R$^4$ is hydrogen. R$^a$ can be, for example, —COO—R$^{a'}$, where R$^{a'}$ is a substituted or unsubstituted alkyl and preferably an unsubstituted C$_1$-C$_6$ alkyl. Preferably, Ar is an optionally substituted phenyl, optionally substituted pyridyl or optionally substituted pyridyl-N-oxide in which the one or more optional substituents may be same or different and are independently hydrogen, hydroxyl, halogen, cyano, nitro, carboxyl, trifluoroalkyl, substituted or unsubstituted alkyl, substituted or unsubstituted alkoxy, substituted or unsubstituted alkoxycarbonyl, substituted or unsubstituted alkylcarbonyl, substituted or unsubstituted alkylcarbonyloxy, substituted or unsubstituted amino or mono or di substituted or unsubstituted alkylamino. According to one embodiment, Ar is

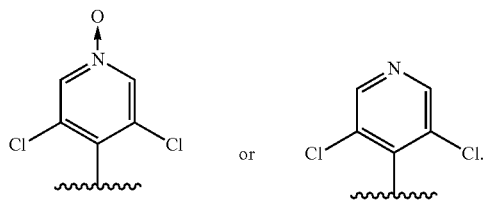

According to another preferred embodiment, the compound has the formula

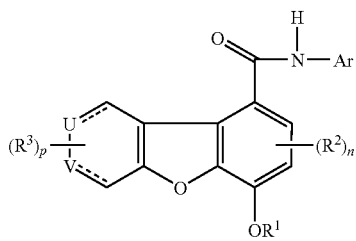

wherein
either (i) U is N, V is N or C, and both dotted lines represent double bonds, or (ii) U is $NR^a$ (where $R^a$ is as defined above), V is C, and both dotted lines are absent;
each occurrence of $R^1$, $R^2$ and $R^3$ may be same or different and are as defined above; and
Ar, n, and p are as defined above,
or a pharmaceutically acceptable salt thereof.

According to a more preferred embodiment, n and p are 0, and $R^1$ is substituted or unsubstituted alkyl. $R^a$ can be, for example, —COO—$R^{a'}$, where $R^{a'}$ is a substituted or unsubstituted alkyl and preferably an unsubstituted $C_1$-$C_6$ alkyl. Preferably, Ar is an optionally substituted phenyl, optionally substituted pyridyl or optionally substituted pyridyl-N-oxide in which the one or more optional substituents may be same or different and are independently hydrogen, hydroxyl, halogen, cyano, nitro, carboxyl, trifluoroalkyl, substituted or unsubstituted alkyl, substituted or unsubstituted alkoxy, substituted or unsubstituted alkoxycarbonyl, substituted or unsubstituted alkylcarbonyl, substituted or unsubstituted alkylcarbonyloxy, substituted or unsubstituted amino or mono or di substituted or unsubstituted alkylamino. According to one embodiment, Ar is

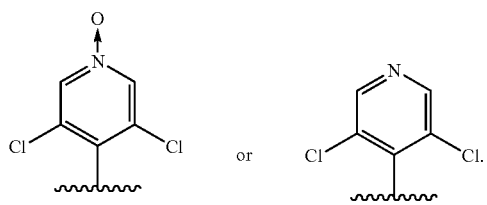

It will be appreciated that some of the compounds of formula (1) can contain one or more asymmetrically substituted carbon atoms. The presence of one or more of these asymmetric centers in the compounds of formula (1) can give rise to stereoisomers and in each case the invention is to be understood to extend to all such stereoisomers, including enantiomers and diastereomers and their mixtures, including racemic mixtures. The invention may also contain E and Z geometrical isomers wherever possible in the compounds of formula (1) which includes the single isomer or mixture of both the isomers Another embodiment of the invention is a pharmaceutical composition containing one or more of the heterocyclic compounds of the present invention and a pharmaceutically acceptable excipient (such as a pharmaceutically acceptable carrier or diluent). The pharmaceutical composition may be, for example, a unit dosage form (such as a tablet or capsule).

The compounds of formula (1) down regulate or inhibit the production of TNF-α as they are PDE4 inhibitors and therefore are useful in the treatment of allergic and inflammatory diseases including asthma, chronic bronchitis, atopic dermatitis, urticaria, allergic rhinitis, allergic conjunctivitis, vernal conjunctivitis, eosinophilic granuloma, psoriasis, rheumatoid arthritis, septic shock, diabetes, ulcerative colitis, Crohn's disease, reperfusion injury of the myocardium and brain, chronic glomerulonephritis, endotoxic shock and adult respiratory distress syndrome. The compounds of the present invention are particularly useful for the treatment of asthma and chronic obstructive pulmonary disease (COPD).

Yet another embodiment of the invention is a method of treating an inflammatory disease, disorder or condition characterized by or associated with an undesirable inflammatory immune response, or a disease or condition induced by or associated with an excessive secretion of TNF-α and PDE-4 in a subject in need thereof by administering to the subject a therapeutically effective amount of a PDE-4 inhibitor or a pharmaceutical composition of the present invention.

Yet another embodiment of the invention is a method of treating an inflammatory condition or an immune disorder in a subject in need thereof by administering to the subject a therapeutically effective amount of a compound according to formula (I) or a pharmaceutical composition of the present invention. Inflammatory conditions and immune disorders which can be treated with the PDE-4 inhibitors of the present invention include, but are not limited to, asthma, bronchial asthma, chronic obstructive pulmonary disease, allergic rhinitis, eosinophilic granuloma, nephritis, rheumatoid arthritis, cystic fibrosis, chronic bronchitis, multiple sclerosis, Crohn's disease, psoriasis, uticaria, adult vernal conjunctivitis, respiratory distress syndrome, rheumatoid spondylitis, osteoarthritis, gouty arthritis, uveits, allergic conjunctivitis, inflammatory bowel conditions, ulcerative coalitis, eczema, atopic dermatitis and chronic inflammation. Preferred inflammatory conditions include, but are not limited to, allergic inflammatory conditions.

Further preferred are inflammatory conditions and immune disorders selected from inflammatory conditions and immune disorders of the lungs, joints, eyes, bowels, skin or heart.

Further preferred are inflammatory conditions chosen from the group consisting of asthma and chronic obstructive pulmonary disease.

Yet another embodiment of the invention is a method for abating inflammation in an affected organ or tissue by delivering to the organ or tissue a therapeutically effective amount of a PDE4 inhibitor or a pharmaceutical composition of the present invention.

Yet another embodiment of the invention is a method of treating a disease of the central nervous system in a subject in need thereof by administering to the subject a therapeutically effective amount of a PDE-4 inhibitor or a pharmaceutical composition of the present invention.

Preferred diseases of the central nervous system include, but are not limited to, depression, amnesia, dementia, Alzheimers disease, cardiac failure, shock and cerebrovascular disease.

Yet another embodiment of the invention is a method of treating insulin resistant diabetes in a subject in need thereof by administering to the subject a therapeutically effective amount of a PDE-4 inhibitor or a pharmaceutical composition of the present invention.

The present invention also relates to processes for the preparation of the novel heterocyclic compounds of formula (1) as defined above.

DETAILED DESCRIPTION OF THE INVENTION

The term "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl).

The term "alkenyl" refers to an aliphatic hydrocarbon group containing a carbon-carbon double bond and which may be a straight or branched chain having 2 to about 10 carbon atoms, e.g., ethenyl, 1-propenyl, 2-propenyl (allyl), iso-propenyl, 2-methyl-1-propenyl, 1-butenyl, and 2-butenyl.

The term "alkynyl" refers to a straight or branched chain hydrocarbyl radical having at least one carbon-carbon triple bond, and having in the range of 2 up to about 12 carbon atoms (with radicals having in the range of about 2 up to 10 carbon atoms presently being preferred), e.g., ethynyl, propynyl, and butynyl.

The term "alkoxy" refers to an alkyl group as defined above attached via an oxygen linkage to the rest of the molecule. Non-limiting examples of such groups include —OCH$_3$, and —OC$_2$H$_5$.

The term "alkylcarbonyl" refers to an alkyl group as defined above attached via a carbonyl linkage to the rest of the molecule. Non-limiting examples of such groups include —C(O)CH$_3$, and —C(O)C$_2$H$_5$.

The term "alkoxycarbonyl" refers to an alkoxy group as defined above attached via a carbonyl linkage to the rest of the molecule. Non-limiting examples of such groups include —C(O)—OCH$_3$, and —C(O)—OC$_2$H$_5$.

The term "alkylcarbonyloxy" refers to an alkylcarbonyl group as defined above attached via an oxygen linkage to the rest of the molecule. Non-limiting examples of such groups include —C(O)CH$_3$, and —O—C(O)C$_2$H$_5$.

The term "alkylamino" refers to an alkyl group as defined above attached via an amino linkage to the rest of the molecule. Non-limiting examples of such groups include —NH$_2$CH$_3$, —NH(CH$_3$)$_2$, and —N(CH$_3$)$_3$.

The term "cycloalkyl" refers to a non-aromatic mono or multicyclic ring system of 3 to about 12 carbon atoms, such as cyclopropyl, cyclobutyl, cyclopentyl, and cyclohexyl. Non-limiting examples of multicyclic cycloalkyl groups include perhydronaphthyl, adamantyl and norbornyl groups, bridged cyclic groups or spirobicyclic groups, e.g., spiro(4,4)non-2-yl.

The term "cycloalkylalkyl" refers to a cyclic ring-containing radical containing in the range of 3 up to about 8 carbon atoms directly attached to an alkyl group which are then attached to the main structure at any carbon from the alkyl group that results in the creation of a stable structure. Non-limiting examples of such groups include cyclopropylmethyl, cyclobutylethyl, and cyclopentylethyl.

The term "cycloalkenyl" refers to a cyclic ring-containing radical containing in the range of 3 up to about 8 carbon atoms with at least one carbon-carbon double bond such as cyclopropenyl, cyclobutenyl, and cyclopentenyl.

The term "cycloalkenylalkyl" refers to a cyclic ring-containing radical containing in the range of about 3 up to 8 carbon atoms with at least one carbon-carbon double bond directly attached to an alkyl group which is then attached to the main structure at any carbon from the alkyl group that results in the creation of a stable structure. Non-limiting examples of such groups include cyclopropenylmethyl, cyclobutenylethyl, and cyclopentenylethyl.

The term "aryl" refers to an aromatic radical having in the range of 6 up to 14 carbon atoms such as phenyl, naphthyl, tetrahydronaphthyl, indanyl, and biphenyl.

The term "arylalkyl" refers to an aryl group as defined above directly bonded to an alkyl group as defined above, e.g., —CH$_2$C$_6$H$_5$, and —C$_2$H$_5$C$_6$H$_5$.

The term "heterocyclic ring" refers to a stable 3- to 15 membered ring radical which consists of carbon atoms and from one to five heteroatoms selected from the group consisting of nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic). Examples of such heterocyclic ring radicals include, but are not limited to, azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofuranyl, tetrahydropyranyl, thienyl, benzothienyl, thiamorpholinyl, thiamorpholinyl sulfoxide thiamorpholinyl sulfone, dioxaphospholanyl, oxadiazolyl, chromanyl, and isochromanyl. The heterocyclic ring radical may be attached to the main structure at any heteroatom or carbon atom that results in the creation of a stable structure.

The term "heteroaryl" refers to an aromatic heterocyclic ring radical. The heteroaryl ring radical may be attached to the main structure at any heteroatom or carbon atom that results in the creation of a stable structure.

The term "heteroarylalkyl" refers to heteroaryl ring radical as defined above directly bonded to an alkyl group. The heteroarylalkyl radical may be attached to the main structure at any carbon atom from alkyl group that results in the creation of a stable structure.

The term "heterocyclyl" refers to a heterocyclic ring radical as defined above. The heterocyclyl ring radical may be attached to the main structure at any heteroatom or carbon atom that results in the creation of a stable structure.

The term "heterocyclylalkyl" refers to a heterocylic ring radical as defined above directly bonded to an alkyl group. The heterocyclylalkyl radical may be attached to the main structure at any carbon atom in the alkyl group that results in the creation of a stable structure.

The term "cyclic ring" refers to a cyclic ring containing 3-10 carbon atoms.

The term "protecting group" or "PG" refers to a substituent that is employed to block or protect a particular functionality while other functional groups on the compound may remain reactive. For example, an "amino-protecting group" is a substituent attached to an amino group that blocks or protects the amino functionality in the compound. Suitable amino-protecting groups include, but are not limited to, acetyl, trifluoroacetyl, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable hydroxy-protecting groups include, but are not limited to, acetyl, benzyl, tetrahydropyranyl and silyl. A "carboxy-protecting group" refers to a substituent of the carboxy group that blocks or protects the carboxy functionality. Suitable carboxy-protecting groups include, but are not limited to, —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, and nitroethyl. For a general description of protecting groups and their use, see, T. W. Greene, Protective Groups in Organic Synthesis, John Wiley & Sons, New York, 1991.

The term "halogen" refers to a radical of fluorine, chlorine, bromine or iodine.

Unless otherwise specified, the term "substituted" as used herein refers to substitution with any one or any combination of the following substituents: hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted amino, substituted or unsubstituted aryl, substituted or unsubstituted heteroaryl, substituted or unsubstituted heteroarylalkyl, substituted or unsubstituted heterocyclic ring, substituted or unsubstituted heterocyclylalkyl ring, substituted or unsubstituted guanidine, —$COOR^x$, —$C(O)R^x$, —$C(S)R^x$, —$C(O)NR^xR^y$, —$C(O)ONR^xR^y$, —$NR^xCONR^yR^z$, —$N(R^x)SOR^y$, —$N(R^x)SO_2R^y$, —(=N—N($R^x$)$R^y$), —$NR^xC(O)OR^y$, —$NR^xR^y$, —$NR^xC(O)R^y$, —$NR^xC(S)R^y$, —$NR^xC(S)NR^yR^z$, —$SONR^xR^y$, —$SO_2NR^xR^y$, —$OR^x$, —$OR^xC(O)NR^yR^z$, —$OR^xC(O)OR^y$, —$OC(O)R^x$, —$OC(O)NR^xR^y$, —$R^xNR^yC(O)R^z$, —$R^xOR^y$, —$R^xC(O)OR^y$, —$R^xC(O)NR^yR^z$, —$R^xC(O)R^y$, —$R^xOC(O)R^y$, —$SR^x$, —$SOR^x$, —$SO_2R^x$, and —$ONO_2$, wherein $R^x$, $R^y$ and $R^z$ are independently selected from hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, or substituted or unsubstituted heterocyclic ring. According to one embodiment, the substituents in the aforementioned "substituted" groups cannot be further substituted. For example, when the substituent on "substituted alkyl" is "substituted aryl", the substituent on "substituted aryl" cannot be "substituted alkenyl".

Pharmaceutically acceptable salts forming part of this invention include salts derived from inorganic bases (such as Li, Na, K, Ca, Mg, Fe, Cu, Zn, and Mn), salts of organic bases (such as N,N'-diacetylethylenediamine, glucamine, triethylamine, choline, hydroxide, dicyclohexylamine, metformin, benzylamine, trialkylamine, thiamine, and the like), salts of chiral bases (such as alkylphenylamine, glycinol, phenyl glycinol and the like), salts of natural amino acids (such as glycine, alanine, valine, leucine, isoleucine, norleucine, tyrosine, cystine, cysteine, methionine, proline, hydroxy proline, histidine, ornithine, lysine, arginine, serine, and the like), salts of non-natural amino acids (such as D-isomers or substituted amino acids), salts of guanidine, salts of substituted guanidine (wherein the substituents are selected from nitro, amino, alkyl, alkenyl, or alkynyl), ammonium salts, substituted ammonium salts, and aluminum salts. Other pharmaceutically acceptable salts include acid addition salts (where appropriate) such as sulphates, nitrates, phosphates, perchlorates, borates, hydrohalides, acetates, tartrates, maleates, citrates, fumarates, succinates, palmoates, methanesulphonates, benzoates, salicylates, benzenesulfonates, ascorbates, glycerophosphates, ketoglutarates and the like. Yet other pharmaceutically acceptable salts include, but are not limited to, quaternary ammonium salts of the compounds of the present invention with alkyl halides or alkyl sulphates (such as MeI and (Me)$_2$SO$_4$). Pharmaceutically acceptable solvates may be hydrates or comprise other solvents of crystallization such as alcohols.

Pharmaceutically acceptable solvates include hydrates and other solvents of crystallization (such as alcohols). The compounds of the present invention may form solvates with low molecular weight solvents by methods known in the art.

The term "treating" or "treatment" of a state, disorder or condition includes:
(1) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition;
(2) inhibiting the state, disorder or condition, i.e., arresting or reducing the development of the disease or at least one clinical or subclinical symptom thereof, or
(3) relieving the disease, i.e., causing regression of the state, disorder or condition or at least one of its clinical or subclinical symptoms.

The benefit to a subject to be treated is either statistically significant or at least perceptible to the subject or to the physician.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disorder or condition, is sufficient to effect such treatment. The "therapeutically effective amount" will vary depending on the compound, the disease and its severity and the age, weight, physical condition and responsiveness of the subject to be treated.

"Delivering" a therapeutically effective amount of an active ingredient to a particular location within a host means causing a therapeutically effective blood concentration of the active ingredient at the particular location. This can be accomplished, e.g., by local or by systemic administration of the active ingredient to the host.

The classic symptoms of acute inflammation are redness, elevated temperature, swelling, and pain in the affected area, and loss of function of the affected organ.

Symptoms and signs of inflammation associated with specific conditions include:

rheumatoid arthritis—pain, swelling, warmth and tenderness of the involved joints; generalized and morning stiffness;

insulin-dependent diabetes mellitus—insulitis; this condition can lead to a variety of complications with an inflammatory component, including: retinopathy, neuropathy, nephropathy; coronary artery disease, peripheral vascular disease, and cerebrovascular disease;

autoimmune thyroiditis—weakness, constipation, shortness of breath, puffiness of the face, hands and feet, peripheral edema, bradycardia;

multiple sclerosis—spasticity, blurry vision, vertigo, limb weakness, paresthesias;

uveoretinitis—decreased night vision, loss of peripheral vision;

lupus erythematosus—joint pain, rash, photosensitivity, fever, muscle pain, puffiness of the hands and feet, abnormal urinalysis (hematuria, cylinduria, proteinuria), glomerulonephritis, cognitive dysfunction, vessel thrombosis, pericarditis;

scleroderma—Raynaud's disease; swelling of the hands, arms, legs and face; skin thickening; pain, swelling and stiffness of the fingers and knees, gastrointestinal dysfunction, restrictive lung disease; pericarditis; renal failure;

other arthritic conditions having an inflammatory component such as rheumatoid spondylitis, osteoarthritis, septic arthritis and polyarthritis—fever, pain, swelling, tenderness;

other inflammatory brain disorders, such as meningitis, Alzheimer's disease, AIDS dementia encephalitis—photophobia, cognitive dysfunction, memory loss;

other inflammatory eye inflammations, such as retinitis—decreased visual acuity;

inflammatory skin disorders, such as, eczema, other dermatites (e.g., atopic, contact), psoriasis, burns induced by UV radiation (sun rays and similar UV sources)—erythema, pain, scaling, swelling, tenderness;

inflammatory bowel disease, such as Crohn's disease, ulcerative colitis—pain, diarrhea, constipation, rectal bleeding, fever, arthritis;

asthma—shortness of breath, wheezing;

other allergy disorders, such as allergic rhinitis—sneezing, itching, runny nose conditions associated with acute trauma such as cerebral injury following stroke—sensory loss, motor loss, cognitive loss;

heart tissue injury due to myocardial ischemia—pain, shortness of breath;

lung injury such as that which occurs in adult respiratory distress syndrome—shortness of breath, hyperventilation, decreased oxygenation, pulmonary infiltrates;

inflammation accompanying infection, such as sepsis, septic shock, toxic shock syndrome—fever, respiratory failure, tachycardia, hypotension, leukocytosis;

other inflammatory conditions associated with particular organs or tissues, such as nephritis (e.g., glomerulonephritis)—oliguria, abnormal urinalysis;

inflamed appendix—fever, pain, tenderness, leukocytosis;

gout—pain, tenderness, swelling and erythema of the involved joint, elevated serum and/or urinary uric acid;

inflamed gall bladder—abdominal pain and tenderness, fever, nausea, leukocytosis;

chronic obstructive pulmonary disease—shortness of breath, wheezing;

congestive heart failure—shortness of breath, rales, peripheral edema;

Type II diabetes—end organ complications including cardiovascular, ocular, renal, and peripheral vascular disease, lung fibrosis—hyperventilation, shortness of breath, decreased oxygenation;

vascular disease, such as atherosclerosis and restenosis—pain, loss of sensation, diminished pulses, loss of function and alloimmunity leading to transplant rejection—pain, tenderness, fever.

Subclinical symptoms include without limitation diagnostic markers for inflammation the appearance of which may precede the manifestation of clinical symptoms. One class of subclinical symptoms is immunological symptoms, such as the invasion or accumulation in an organ or tissue of proinflammatory lymphoid cells or the presence locally or peripherally of activated pro-inflammatory lymphoid cells recognizing a pathogen or an antigen specific to the organ or tissue. Activation of lymphoid cells can be measured by techniques known in the art.

The compounds of the invention are effective over a wide dosage range. For example, in the treatment of adult humans, dosages from about 0.05 to about 1000 mg, preferably from about 0.1 to about 500 mg, per day may be used. A most preferable dosage is about 0.5 mg to about 250 mg per day. In choosing a regimen for patients it may frequently be necessary to begin with a higher dosage and when the condition is under control to reduce the dosage. The exact dosage will depend upon the mode of administration, on the therapy desired, form in which administered, the subject to be treated and the body weight of the subject to be treated, and the preference and experience of the physician or veterinarian in charge.

Generally, the compounds of the present invention are dispensed in a unit dosage form comprising from about 0.05 to about 1000 mg of active ingredient together with a pharmaceutically acceptable carrier.

Generally, dosage forms suitable for oral, nasal, pulmonal or transdermal administration comprise from about 0.05 mg to about 1000 mg, preferably from about 0.5 mg to about 250 mg of the compounds admixed with a pharmaceutically acceptable carrier or diluent.

Some of the representative compounds according to the present invention are specified below but should not construed to be limited thereto;

1. N9-(3,5-dichloro-4-pyridyl)-6-methoxybenzo[4,5]furo[2,3-d]pyridazine-9-carboxamide
2. N9-(3,5-dichloro-4-pyridyl)-6-methoxybenzo[4,5]furo[3,2-d]pyrimidine-9-carboxamide
3. N9-(3,5-dichloro-4-pyridyl)-6-methoxybenzo[4,5]furo[3,2-c]pyridine-9-carboxamide
4. N9-(3,5-dichloro-4-pyridyl)-6-difluoromethoxybenzo[4,5]furo[2,3-d]pyridazine-9-carboxamide
5. N9-(3,5-dichloro-4-pyridyl)-6-difluoromethoxybenzo[4,5]furo[2,3-d]pyridazine-9-carboxamide sodium
6. 2-ethyl-5-(4-nitrophenyl)-8-methoxy-1,2,3,4-tetrahydrobenzo[4,5]thieno[2,3-c]pyridine-2,5-dicarboxylate
7. 5-(3,5-dichloro-4-pyridylcarbamoyl)-8-methoxy-1,2,3,4-tetrahydrobenzo[4,5]thieno[2,3-c]pyridine-2-carboxylate 8. N5-(3,5-dichloro-4-pyridyl)-8-methoxy-1,2,3,4-tetrahydrobenzo[4,5]thieno[2,3-c]pyridine-5-carboxamide hydrochloride
9. Ethyl 9-(3,5-dichloro-4-pyridylcarbamoyl)-8-methoxy-1,2,3,4-tetrahydro benzo[4,5]furo[3,2-c]pyridine-2-carboxylate
10. tert-butyl 9-(3,5-dichloro-4-pyridylcarbamoyl)-6-methoxy-5-methyl-1,3,4,5-tetrahydro-1H-pyrido[4,3-b]indole-2-carboxylate
11. tert-butyl 9-(3,5-dichloro-4-pyridylcarbamoyl)-6-methoxy-5-benzyl-1,3,4,5-tetrahydro-1H-pyrido[4,3-b]indole-2-carboxylate
12. tert-butyl-9-(3,5-dichloro-4-pyridylcarbamoyl)-6-methoxy-5-cyclopropyl methyl-1,3,4,5-tetrahydro-1H-pyrido[4,3-b]indole-2-carboxylate
13. N9-(3,5-dichloro-4-pyridylcarbamoyl)-6-methoxy-5-methyl-1,3,4,5-tetrahydro-1H-pyrido[4,3-b]indole hydrochloride
14. N9-(3,5-dichloro-4-pyridylcarbamoyl)-6-methoxy-5-benzyl-1,3,4,5-tetrahydro-1H-pyrido[4,3-b]indole hydrochloride
15. N9-(3,5-dichloro-4-pyridylcarbamoyl)-6-methoxy-2,5-methyl-1,3,4,5-tetrahydro-1H-pyrido[4,3-b]indole
16. N9-(3,5-dichloro-4-pyridylcarbamoyl)-6-methoxy-2-methyl-5-benzyl-1,3,4,5-tetrahydro-1H-pyrido[4,3-b]indole
17. tert-butyl-9-(4-pyridinylcarbamoyl)-6-methoxy-5-methyl-1,3,4,5-tetrahydro-1H-pyrido[4,3-b]indole-2-carboxylate
18. N9-(3,5-dichloro-4-pyridyl)-6-methoxybenzo[4,5]furo[2,3-d]pyridazine-9-carboxamide sodium
19. N-(3,5-dichloropyridin-4-yl)-2-(ethoxycarbonyl)-8-methoxy-1,2,3,4-tetrahydro[1]benzofuro[2,3-c]pyridine-5-carboxamide
20. N-(3,5-dichloropyridin-4-yl)-8-methoxy-1,2,3,4-tetrahydro[1]benzofuro[2,3-c]pyridine-5-carboxamide hydrochloride
21. N-(3,5-dichloropyridin-4-yl)-6-methoxy-1,2,3,4-tetrahydro[1]benzofuro[3,2-c]pyridine-9-carboxamide hydrochloride
22. N-(3,5-dichloropyridin-4-yl)-2,9-dimethyl-8-methoxy-1-oxo-1,2,3,4-tetrahydro-β-carboline-5-carboxamide
23. N9-(3,5-dichloro-4-pyridyl)-6-difluoromethoxybenzo[4,5]furo[3,2-c]pyridine-9-carboxamide
24. N9-(3,5-dichloro-4-pyridyl)-6-difluoromethoxybenzo[4,5]furo[3,2-c]pyridine-9-carboxamide sodium
25. 3,5-dichloro-4-(6-difluoromethoxybenzo[4,5]furo[2,3-d]pyridazine-9-ylcarboxamido)-1-pyridiniumolate
26. 3,5-dichloro-4-(6-difluoromethoxybenzo[4,5]furo[3,2-c]pyridin-9-ylcarboxamido)-1-pyridiniumolate
27. 3,5-dichloro-4-(6-difluoromethoxybenzo[4,5]furo[3,2-c]pyridin-9-ylcarboxamido)-1 pyridiniumolate sodium
28. N9-(3,5-dichloro-4-pyridyl)-6-difluoromethoxy-3-ethyl-4-oxo-3,4-dihydro benzo[4,5]furo[2,3-d]pyridazine-9-carboxamide
29. N9-(3,5-dichloro-4-pyridyl)-3-(4-chlorophenyl)-6-difluoromethoxy-4-oxo-3,4-dihydrobenzo[4,5]furo[2,3-d]pyridazine-9-carboxamide
30. N9-(3,5-dichloro-4-pyridyl)-6-difluoromethoxy-3-butyl-4-oxo-3,4-dihydrobenzo[4,5]furo[2,3-d]pyridazine-9-carboxylate
31. N9-(3,5-dichloro-4-pyridyl)-6-difluoromethoxy-3-cyclopentyl-4-oxo-3,4-dihydrobenzo[4,5]furo[2,3-d]pyridazine-9-carboxylate and pharmaceutically acceptable salts thereof (when the compound is described as its free base) or the free base and other pharmaceutically acceptable salts thereof (when the compound is described as a salt).

Methods of Preparation

The compounds of formula (I) may be prepared by the following processes. The symbols Ar, T, U, V, W, X, Y, $R^1$, $R^2$, and $R^3$ when used in the formulae below are to be understood to represent those groups described above in relation to formula (1) unless otherwise indicated.

In one embodiment the compounds of formula (1) wherein Y is —CONR$^4$, T and W are C, U and V are N, the dotted lines [---] in the ring indicate double bonds, p=0, and Ar, X, $R^1$, $R^2$, $R^3$, and n are as described in the general description, can be synthesized as described in the general synthetic scheme I.

General Scheme I:

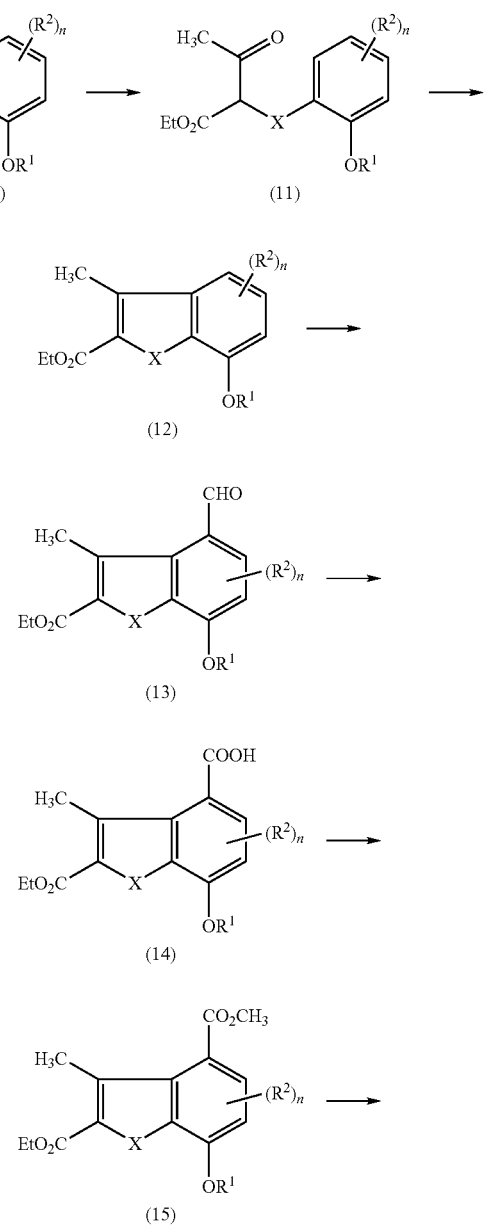

-continued

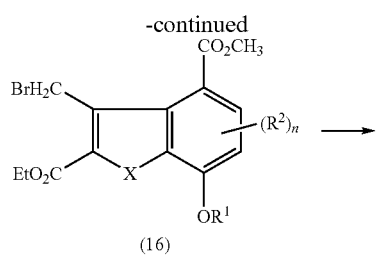
(16)

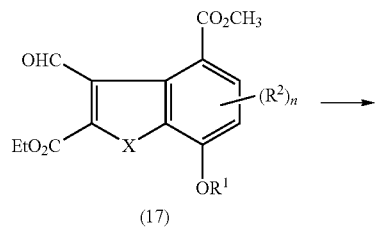
(17)

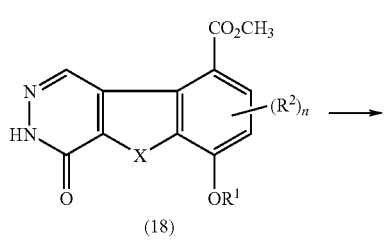
(18)

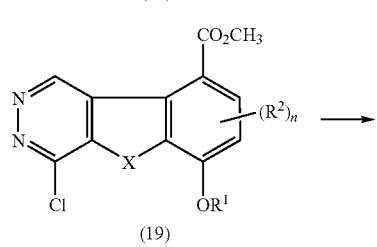
(19)

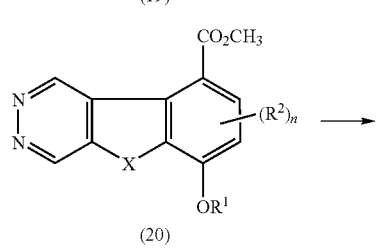
(20)

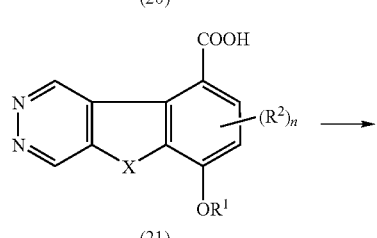
(21)

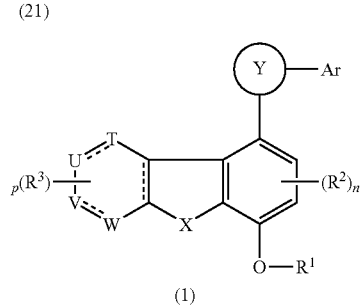
(1)

In the above scheme, an appropriately substituted aromatic compound (10) can be reacted with 2-chloroacetoacetate, for example, in the presence of a base (such as sodium hydroxide and the like), to obtain the intermediate of the formula (11) which can then be cyclised, for example, under acidic conditions (such as polyphosphoric acid (PPA) or methanesulfonic acid and the like), to obtain the intermediate of the formula (12). The intermediate of the formula (12) can then be formylated, for example, with dichloromethyl methyl ether in the presence of tin chloride, to the intermediate of the formula (13). The intermediate of the formula (13) can then be oxidized to the carboxylic acid intermediate of the formula (14), for example with oxidizing agents such as sodium chlorite or potassium permanganate. The intermediate of the formula (14) can then be esterified to give the intermediate of the formula (15). The intermediate of formula (15) can then be converted to the intermediate of the formula (17) via the intermediate of formula (16) using radical bromination followed by oxidation with, for example, alkaline DMSO. The intermediate (17) thus formed can then be reacted with hydrazine hydrate to obtain the intermediate of the formula (18) which can be aromatized using known methods in the art such as phosphorus oxychloride to give the intermediate of formula (19). The intermediate of formula (19) is converted to the intermediate of formula (21). For example, dechlorination, such as under palladium catalysed hydrogenation, (which produces the intermediate of formula (20)) followed by basic hydrolysis will give the intermediate of the formula (21). The final compounds (1) can be prepared by reacting the acid halide or the mixed anhydride or active ester of the intermediate of the formula (21) with an appropriate amine of the formula ArNHR$^4$, for example, using standard basic conditions such as those known in the literature (e.g., in the presence of sodium hydride in DMF or diisopropylethylamine in THF).

In another embodiment, the compounds of the formula (1) wherein Y is —CONR$^4$, T is C, W is C=O, U is N, V is NR$^a$, the dotted line [---] between V and W in the ring is absent, the remaining dotted lines represent double bonds, p=0, and Ar, X, R$^1$, R$^2$, R$^3$, R$^a$ and n are as described in the general description, can be synthesized as described in the general synthetic scheme Ia.

Scheme Ia:

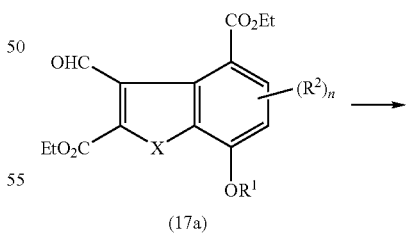
(17a)

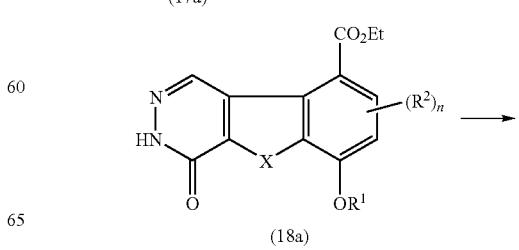
(18a)

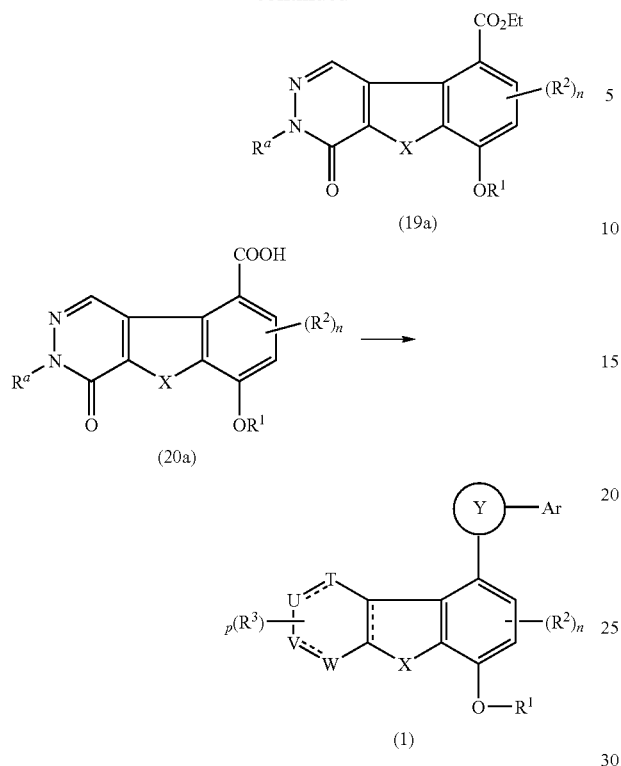

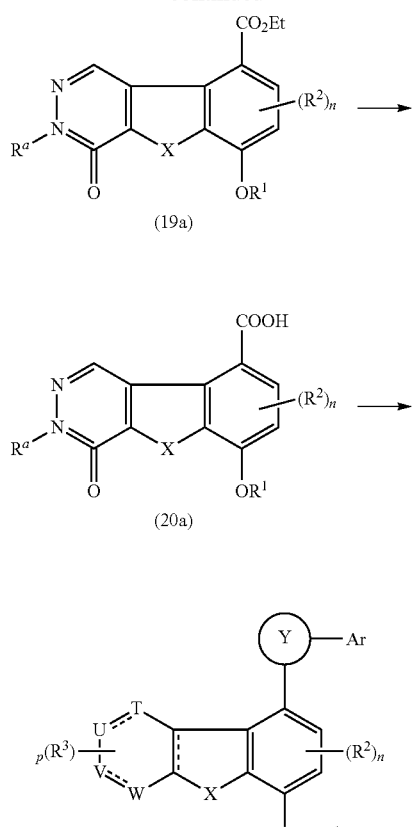

In the above scheme, the intermediate (17a) can be reacted with hydrazine hydrate to obtain the intermediate of formula (18a). Intermediate (18a) can then be reacted with a compound of formula R$^a$-G (wherein G is a leaving group) to yield the intermediate of formula (19a). The intermediate of formula (19a) can be hydrolysed to give the intermediate of formula (20a). The final compound of formula (1) can be prepared by reacting the acid halide or the mixed anhydride or active ester of the intermediate of the formula (20a) with an appropriate amine of the formula ArNHR$^4$, for example, using standard basic conditions such as those known in the literature (e.g., in the presence of sodium hydride in DMF or diisopropylethylamine in THF).

In yet another embodiment, the compounds of formula (1) wherein Y is —CONR$^4$, T is C, W is C=O, U is N, V is NR$^a$, the dotted line [---] between V and W in the ring is absent, the remaining dotted lines represent double bonds, p=0, and Ar, X, R$^1$, R$^2$, R$^3$, R$^a$ and n are as described in the general description, can be synthesized as described in the general synthetic scheme Ib.

Scheme Ib:

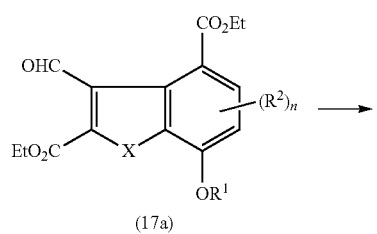

In the above scheme, the intermediate (17a) can be reacted with a intermediate of general formula NH$_2$—NHR$^a$ to obtain the intermediate of formula (19a). The intermediate of formula (19a) can then be hydrolyzed to give the intermediate of formula (20a). The final compounds of formula (1) can be prepared by reacting the acid halide or the mixed anhydride or active ester of the intermediate of the formula (20a) with an appropriate amine of the formula ArNHR$^4$, for example, using standard basic conditions such as those known in the literature (e.g., in the presence of sodium hydride in DMF or diisopropylethylamine in THF).

In yet another embodiment, the desired compounds of formula (1) wherein Y is —CONR$^4$, T and V are N, U and W are C, the dotted lines [---] in the ring indicate double bonds, p=0 or 1, and Ar, X, R$^1$, R$^2$, R$^3$, and n are as described in the general description, can be synthesized as described in the general scheme II.

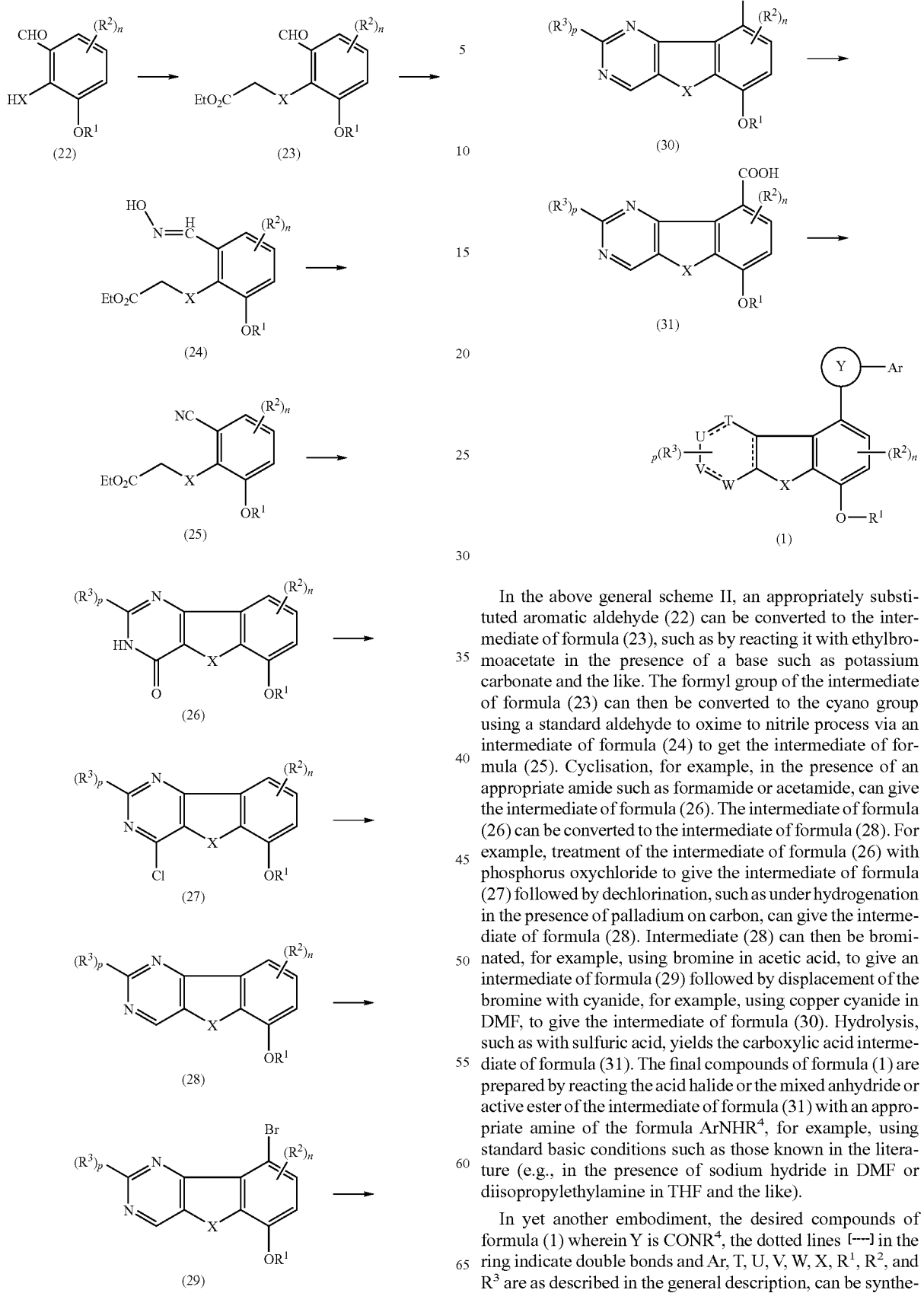

In the above general scheme II, an appropriately substituted aromatic aldehyde (22) can be converted to the intermediate of formula (23), such as by reacting it with ethylbromoacetate in the presence of a base such as potassium carbonate and the like. The formyl group of the intermediate of formula (23) can then be converted to the cyano group using a standard aldehyde to oxime to nitrile process via an intermediate of formula (24) to get the intermediate of formula (25). Cyclisation, for example, in the presence of an appropriate amide such as formamide or acetamide, can give the intermediate of formula (26). The intermediate of formula (26) can be converted to the intermediate of formula (28). For example, treatment of the intermediate of formula (26) with phosphorus oxychloride to give the intermediate of formula (27) followed by dechlorination, such as under hydrogenation in the presence of palladium on carbon, can give the intermediate of formula (28). Intermediate (28) can then be brominated, for example, using bromine in acetic acid, to give an intermediate of formula (29) followed by displacement of the bromine with cyanide, for example, using copper cyanide in DMF, to give the intermediate of formula (30). Hydrolysis, such as with sulfuric acid, yields the carboxylic acid intermediate of formula (31). The final compounds of formula (1) are prepared by reacting the acid halide or the mixed anhydride or active ester of the intermediate of formula (31) with an appropriate amine of the formula ArNHR$^4$, for example, using standard basic conditions such as those known in the literature (e.g., in the presence of sodium hydride in DMF or diisopropylethylamine in THF and the like).

In yet another embodiment, the desired compounds of formula (1) wherein Y is CONR$^4$, the dotted lines [---] in the ring indicate double bonds and Ar, T, U, V, W, X, R$^1$, R$^2$, and R$^3$ are as described in the general description, can be synthesized as described in the general synthetic scheme III.

General Scheme III:

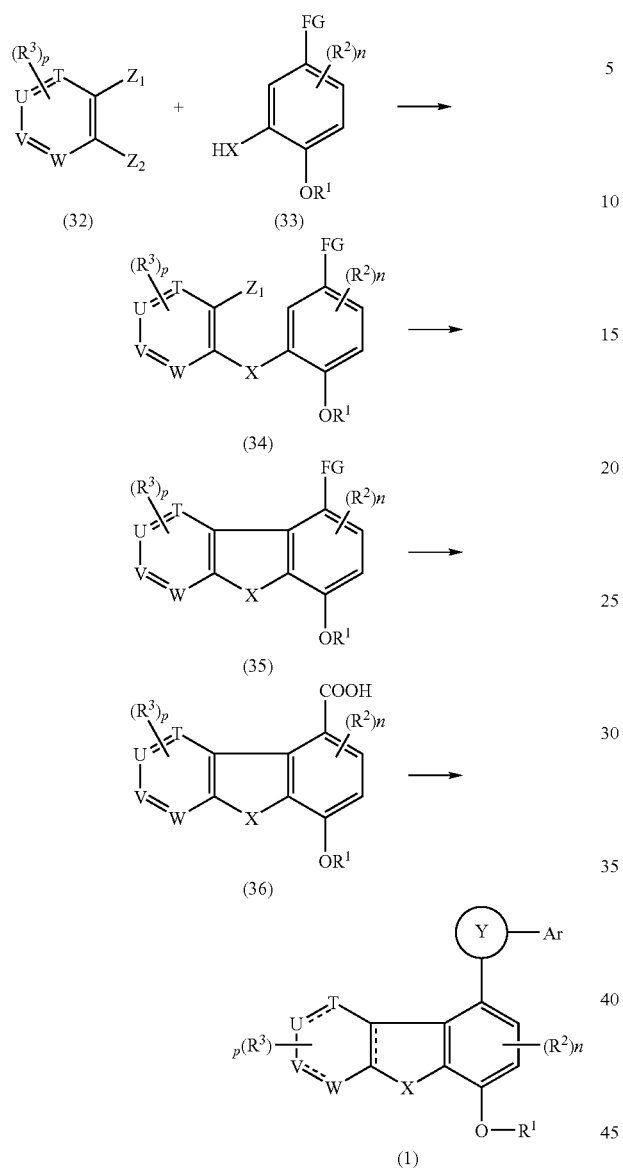

(32) (33)

(34)

(35)

(36)

(1)

In the above general scheme III, the intermediate (34) can be obtained by reacting the compound of formula (32) (wherein $Z_1$ is Br or I and $Z_2$ is F or Cl) with the compound of formula (33) (wherein FG is alkyl, formyl, acetyl, cyano or ester), for example, under appropriate basic conditions such as potassium carbonate in DMF. The intermediate of formula (34) can then be cyclised to the intermediate of formula (35), for example, using catalytic palladium or nickel salts. The functional group (FG) in the intermediate of formula (35) can then be converted to the carboxylic acid (if FG is alkyl, formyl or acetyl then it can be oxidized or if FG is cyano or ester then it can be hydrolysed to the carboxylic acid) to obtain the intermediate of formula (36). The final compounds of formula (1) can then be prepared by reacting the acid halide or the mixed anhydride or active ester of the intermediate of formula (36) with an appropriate amine of the formula ArNHR⁴, for example, using standard basic conditions such as those known in the literature (e.g., in the presence of sodium hydride in DMF or diisopropylethylamine in THF and the like).

In yet another embodiment, the desired compounds of formula (1) wherein Y is $CONR^4$, the dotted lines [---] between T and U and between V and W in the ring are absent, the dotted line in the center ring represents a double bond, and Ar, T, U, V, W, X, $R^1$, $R^2$, and $R^3$ are as described in the general description, can be synthesized as described in the general synthetic scheme IV.

General Scheme IV

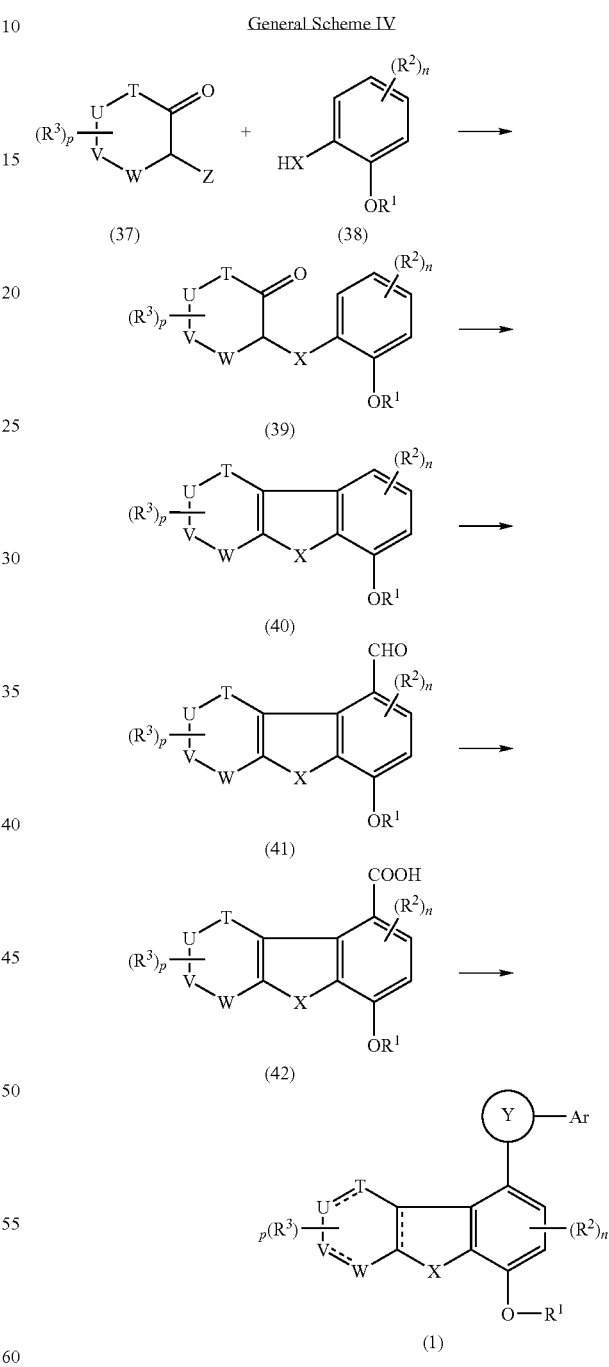

(37) (38)

(39)

(40)

(41)

(42)

(1)

In the above scheme, the intermediate of formula (39) can synthesized by reacting the appropriately substituted or unsubstituted intermediate of formula (37) (wherein Z is a halogen) with an appropriately substituted aryl intermediate of formula (38), for example, under appropriate basic conditions such as potassium carbonate in DMF. Intermediate (39)

can be cyclized, for example, under standard acidic conditions such as with polyphosphoric acid or methane sulfonic acid, to give the intermediate of formula (40) which further can be formylated, for example, using standard literature methods such as dichlormethylmethyl ether in the presence of a lewis acid (such as tin chloride), to give the intermediate of formula (41). The formyl group of the intermediate of formula (41) can then be oxidized to a carboxylic acid to obtain the intermediate of formula (42). The final compounds of formula (1) can then be prepared by reacting the acid halide or the mixed anhydride or active ester of the intermediate of formula (42) with an appropriate amine of the formula $ArNHR^4$, for example, using standard basic conditions such as those known in the literature (e.g., in the presence of sodium hydride in DMF or diisopropylethylamine in THF and the like).

In yet another embodiment the desired compounds of formula (1) wherein Y is $-CONR^4$, U is N, T, V, and W are C, the dotted lines [---] in the ring indicate double bonds, p=0 or 1, and Ar, X, $R^1$, $R^2$, $R^3$, and n are as described in the general description, can be synthesized as described in the general scheme V.

General Scheme V:

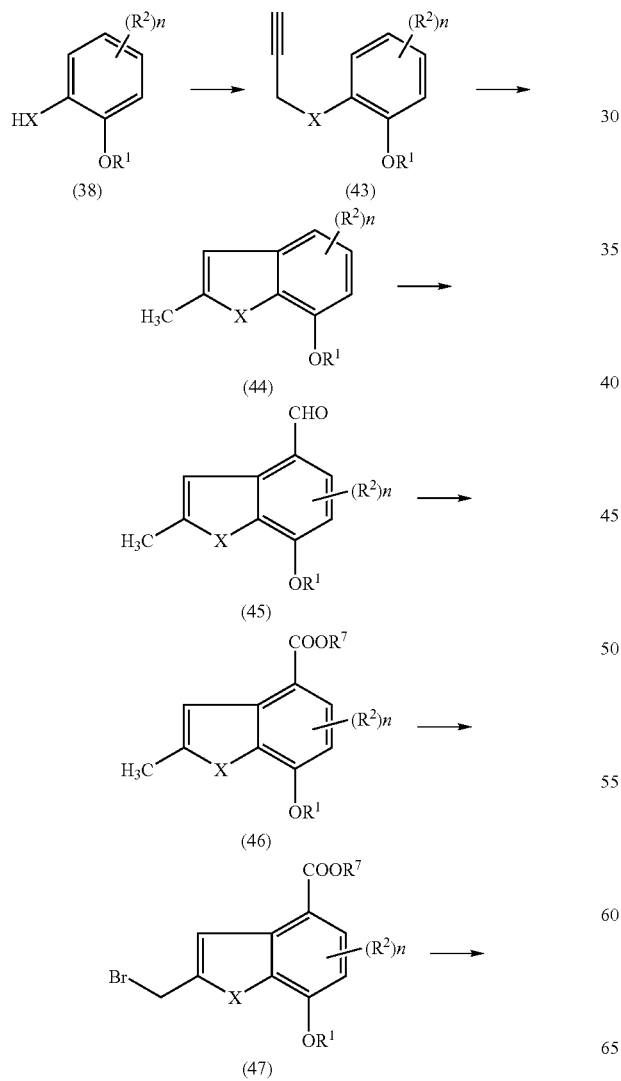

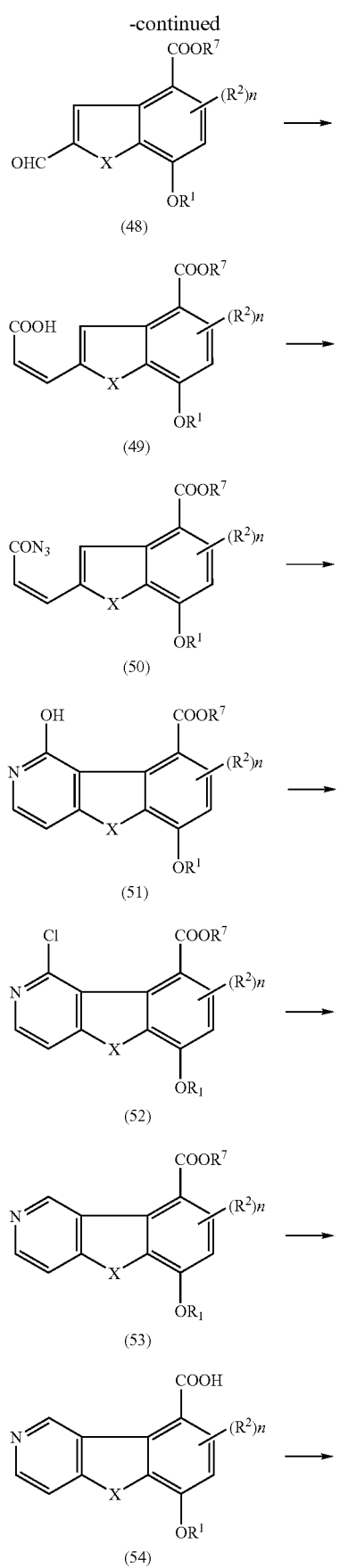

-continued

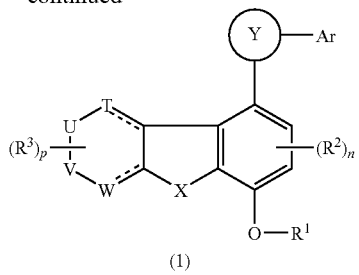

(1)

In the above scheme V, the intermediate (43) can be synthesized by reacting the intermediate of formula (38) and propargyl bromide, for example, in the presence of a suitable base such as potassium carbonate. The intermediate of formula (43) can be subjected to cyclisation, such as in the presence of cesium fluoride, to afford the intermediate (44). Intermediate (45) can be formed by formylation of the intermediate (44), such as with dichloromethylmethyl ether in the presence of tin (IV) chloride. Intermediate (45) can be oxidized, such as with an oxidizing agent (e.g., sodium chlorite, potassium permanganate, or hydrogen peroxide), followed by esterification to yield the intermediate of formula (46), wherein $R^7$ is unsubstituted or substituted alkyl, unsubstituted or substituted aryl, or substituted or substituted arylalkyl. The intermediate of formula (48) can be further obtained by bromination of the intermediate of formula (46), such as with NBS, to yield the intermediate of formula (47), followed by oxidative debromination, such as with dimethylsulfoxide in the presence of a base such as sodium carbonate. The intermediate (48) can be converted to the intermediate of formula (49), such as with malonic acid in the presence of a base such as piperidine. The azido intermediate of formula (50) can then be obtained by treatment of intermediate (49) with, for example, ethyl chloroformate followed by sodium azide. The azido intermediate (50) can be cyclized, for example at a temperature of 180° C. or more, to provide the intermediate of formula (51). Intermediate (51) can be converted, for example, by treatment with phosphorus oxychloride, to form the intermediate of formula (52). Reductive dechlorination of the intermediate (52), for example, with Pd/C or Raney nickel, affords the intermediate (53). Hydrolysis of the intermediate of formula (53), for example, in the presence of a base such as sodium hydroxide and the like, provides the intermediate of formula (54). The final compounds of formula (1) can be prepared by reacting the acid halide or the mixed anhydride or active ester of the intermediate of formula (54) with an appropriate amine of the formula $ArNHR^4$, for example, using standard basic conditions such as those known in the literature (e.g., in the presence of sodium hydride in DMF or diisopropylethylamine in THF and the like).

In yet another embodiment, the desired compounds of formula (1) wherein Y is —$CONR^4$, V is —$NR^a$, T, U, and W are C, the dotted lines [---] between T and U and between V and W in the ring are absent, the remaining dotted line represents a bond, p=0 or 1, and Ar, X, $R^1$, $R^2$, $R^3$, $R^a$ and n are as described in the general description, can be synthesized as described in the general scheme VI.

General Scheme VI:

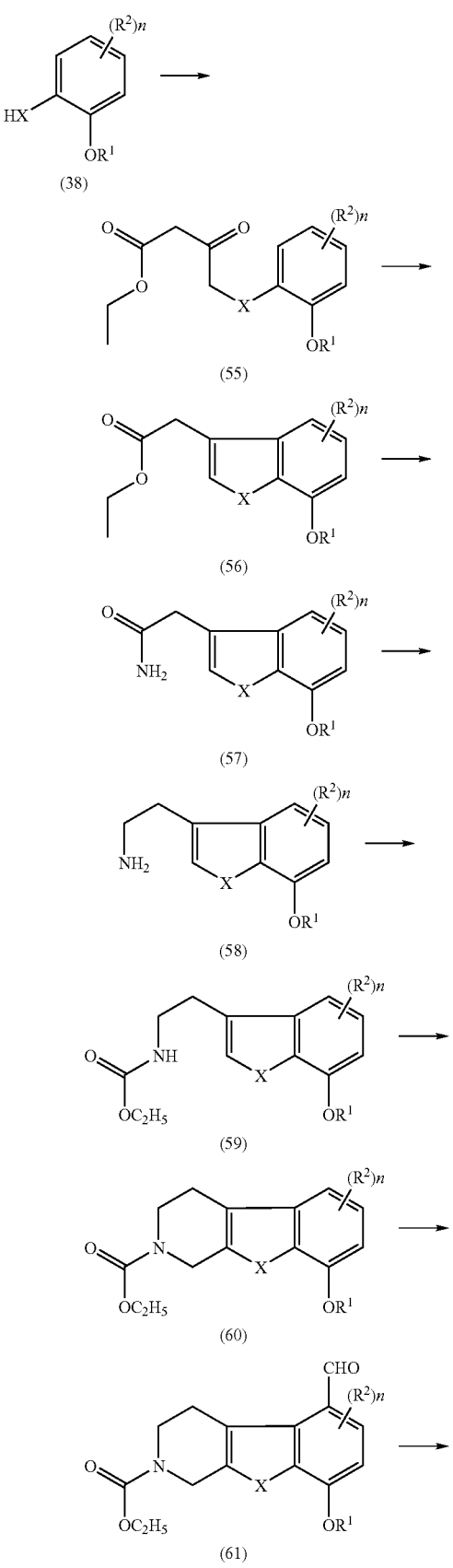

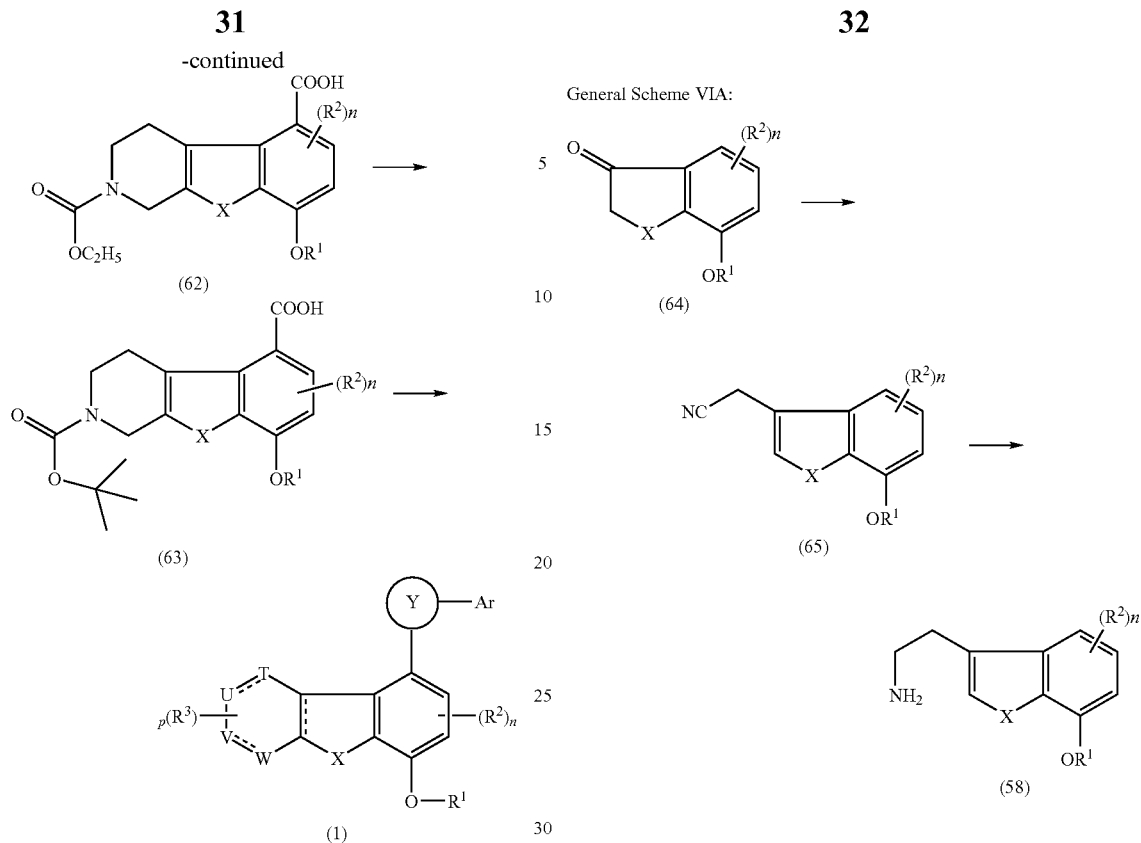

In the above scheme VI, the intermediate (55) can be synthesized by reacting the intermediate of formula (38) with 4-chloroethylacetoacetate, for example, in the presence of a suitable base such as potassium carbonate. Intermediate (55) can be cyclized, such as in the presence of polyphosphoric acid or sulfuric acid, to afford the intermediate of formula (56). This intermediate can be converted to the amide intermediate of formula (57), for example with ammonia (such as in methanol). Reduction of amide intermediate (57) using reducing agents such as borane in THF or lithium aluminium hydride provides the amine intermediate of formula (58). The intermediate of formula (60) can be obtained by treating amine intermediate (58), for example, with ethyl chloroformate, to form the intermediate of formula (59) followed by cyclization, for example, in the presence of formaldehyde and an acid catalyst such as p-toluenesulfonic acid. Intermediate (60) can be formylated, for example using standard conditions such as dichloromethylmethyl ether in the presence of tin (IV) chloride, to obtain the intermediate of formula (61). Intermediate (61) can be oxidized, for example with an oxidizing agent such as sodium chlorite, potassium permanganate or hydrogen peroxide, to form the intermediate of formula (62). The ethyl carbamate portion of the intermediate (62) can be converted to t-butyl carbamate, for example, by basic hydrolysis followed by treatment with, for example, BOC-anhydride to obtain the intermediate of formula (63). The final compounds of formula (1) can be prepared by reacting the acid halide or the mixed anhydride or active ester of the intermediate of the formula (63) with an appropriate amine of the formula ArNHR$^4$, for example, using standard basic conditions such as those known in the literature (e.g., in the presence of sodium hydride in DMF or diisopropylethylamine in THF and the like).

In yet another embodiment, the intermediate (58) can be synthesized as described in general scheme VIA.

In the above scheme VIA, treatment of the intermediate (64) with, for example, cyanoacetic acid in the presence of ammonium acetate can provide the nitrile intermediate (65) which on reduction with a reducing agent, such as lithium aluminum hydride, borane, or Pd/C hydrogenation, can provide the amino intermediate (58). Intermediate (58) can then be converted to compounds of formula (1) by the process described in scheme VI.

In yet another embodiment, the desired compounds of formula (1) wherein Y is —CONR$^4$, U is —NR$^a$, T=V=W is C, the dotted lines [----] between T and U and between V and W in the ring are absent, the remaining dotted line is a bond, p=0 or 1, and Ar, X, R$^1$, R$^2$, R$^3$, R$^a$ and n are as described in the general description, can be synthesized as described in the general scheme VII.

General Scheme VII:

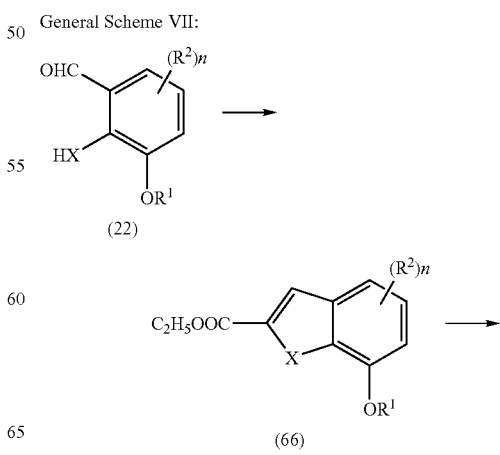

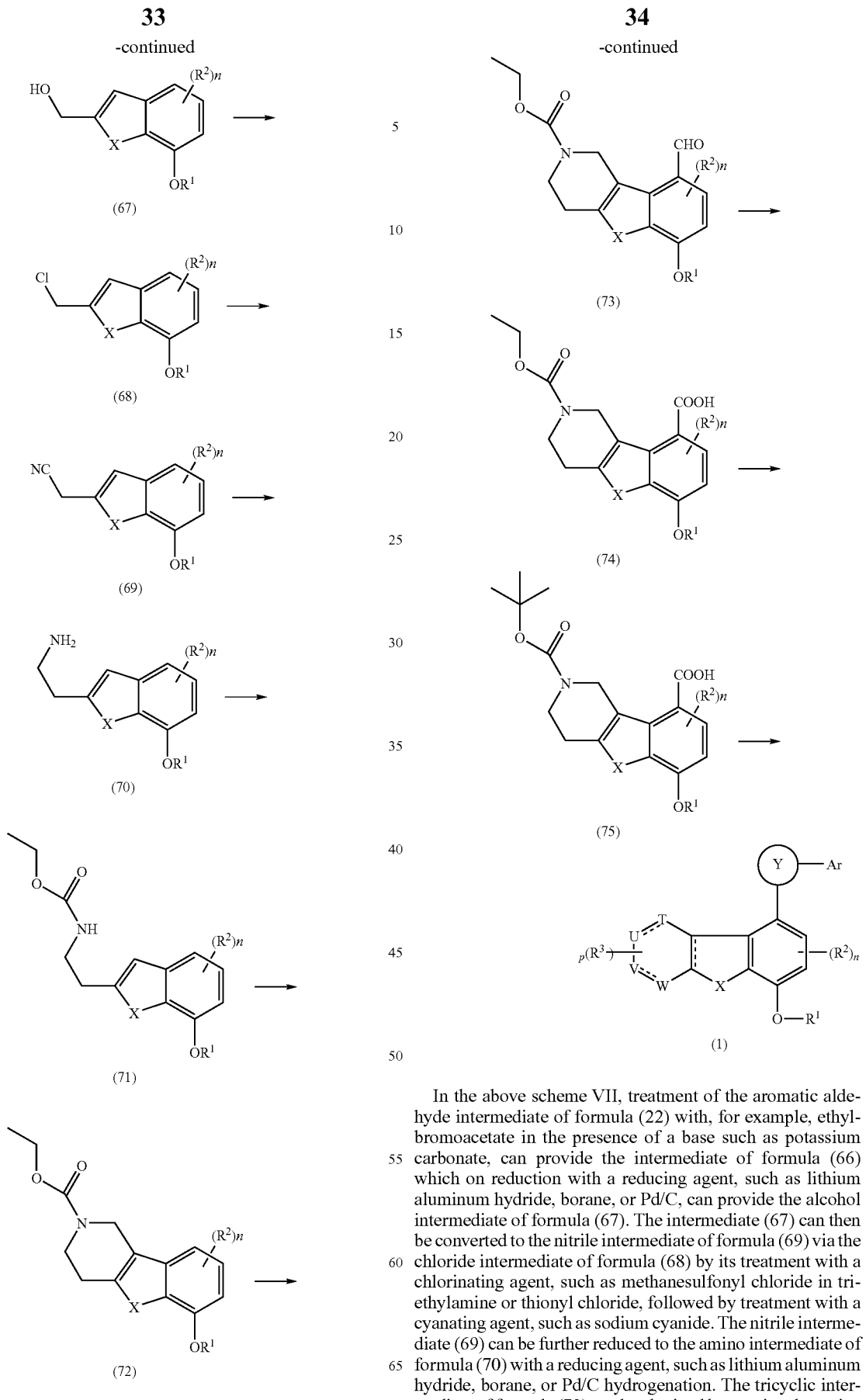

In the above scheme VII, treatment of the aromatic aldehyde intermediate of formula (22) with, for example, ethylbromoacetate in the presence of a base such as potassium carbonate, can provide the intermediate of formula (66) which on reduction with a reducing agent, such as lithium aluminum hydride, borane, or Pd/C, can provide the alcohol intermediate of formula (67). The intermediate (67) can then be converted to the nitrile intermediate of formula (69) via the chloride intermediate of formula (68) by its treatment with a chlorinating agent, such as methanesulfonyl chloride in triethylamine or thionyl chloride, followed by treatment with a cyanating agent, such as sodium cyanide. The nitrile intermediate (69) can be further reduced to the amino intermediate of formula (70) with a reducing agent, such as lithium aluminum hydride, borane, or Pd/C hydrogenation. The tricyclic intermediate of formula (72) can be obtained by treating the amine intermediate of formula (70) with, for example, ethyl chloroformate, to form the intermediate of formula (71) followed by cyclization, for example, in the presence of formaldehyde and an acid catalyst such as p-toluenesulfonic acid. Intermediate (72) can be formylated, for example using standard conditions such as dichloromethylmethyl ether in the presence of tin (IV) chloride to obtain the intermediate of formula (73). Intermediate (73) can be oxidized with an oxidizing agent, such as sodium chlorite, potassium permanganate, or hydrogen peroxide, to form the acid intermediate of formula (74). The ethyl carbamate portion of intermediate (74) can be converted to t-butyl carbamate by, for example, basic hydrolysis followed by treatment with BOC-anhydride to obtain the intermediate of formula (75). The final compounds of formula (1) can be prepared by reacting the acid halide or the mixed anhydride or active ester of the intermediate of formula (75) with an appropriate amine of the formula ArNHR$^4$, for example, using standard basic conditions such as those known in the literature (e.g., in the presence of sodium hydride in DMF or diisopropylethylamine in THF and the like).

In yet another embodiment, the desired compounds of formula (1) wherein Y is —CONR$^4$, V is —NR$^a$, W is —C(=O), T and U are C, the dotted lines [---] between T and U and between V and W in the ring are absent, the remaining dotted line represents a double bond, p=0 or 1, and Ar, X, R$^1$, R$^2$, R$^3$, R$^a$ and n are as described in the general description, can be synthesized as described in the general scheme VIII.

General Scheme VIII:

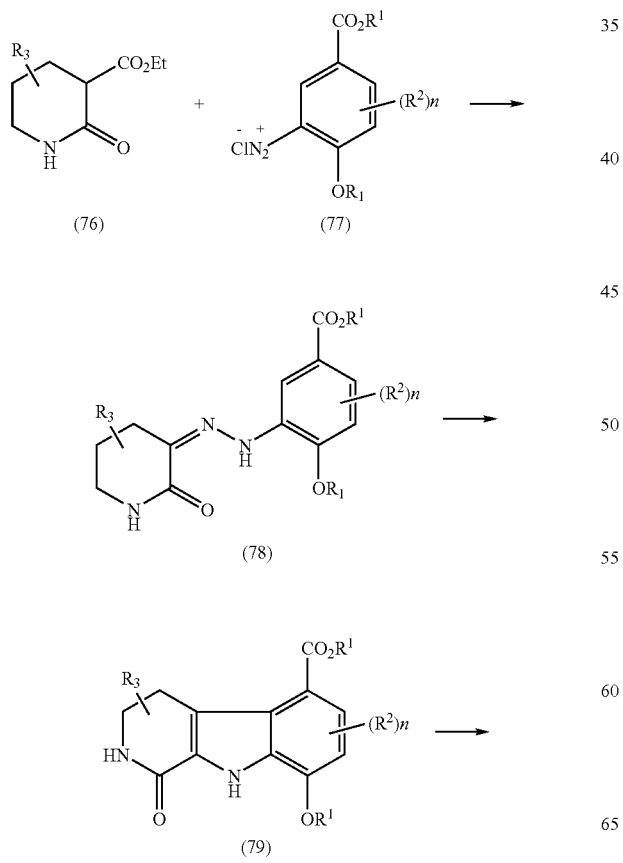

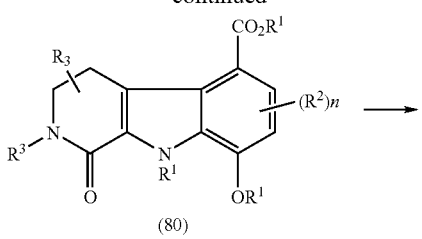

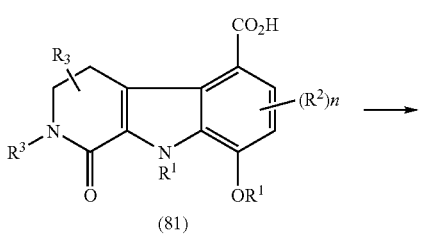

In the above scheme VIII, the intermediate of formula (76) when reacted with the intermediate of formula (77) can provide the intermediate of formula (78), which on acid catalyzed cyclization can provide the intermediate of formula (79). Reacting intermediate (79) with an intermediate of the formula R$^a$-G wherein G is a leaving group (for example R$^a$-G can be an alkyl halide (e.g., iodomethane, ethyl bromide and the like)) in the presence of a base (such as sodium hydride or potassium carbonate) forms the intermediate of formula (80). Hydrolysis of intermediate (80), for example, in the presence of a base, such as sodium hydroxide, provides the acid intermediate of formula (81). The final compounds of formula (1) can be prepared by reacting the acid halide or the mixed anhydride or active ester of intermediate (81) with an appropriate amine of the formula ArNHR$^4$, for example, using standard basic conditions such as those known in the literature (e.g., in the presence of sodium hydride in DMF or diisopropylethylamine in THF and the like).

In yet another embodiment, the desired compounds of formula (1) wherein Y is —CONR$^4$, U is —NR$^a$, S(O)$_m$, or O, T, V, and W are C, the dotted lines [---] between T and U and between V and W in the ring are absent, the remaining dotted line represents a double bond, p=0, X is NR$^b$, and Ar, R$^1$, R$^2$, R$^3$, R$^b$ and n are as described in the general description, can be synthesized as described in the general scheme IX.

General Scheme IX:

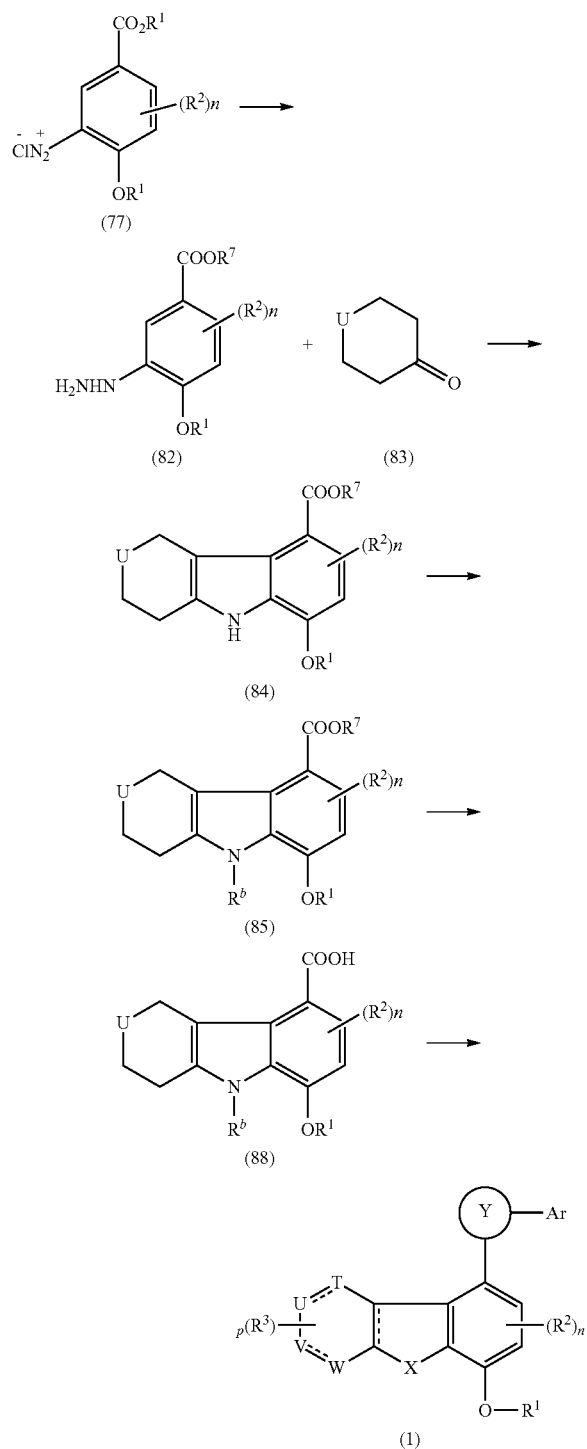

(for example $R^b$-G can be an alkyl halide (e.g., iodomethane, ethyl bromide and the like)) in the presence of a base (such as sodium hydride or potassium carbonate) to provide the intermediate of formula (85). Hydrolysis of intermediate (85), for example, in the presence of a base such as sodium hydroxide, provides the acid intermediate of formula (86). The final compounds of formula (1) can be prepared by reacting the acid halide or the mixed anhydride or active ester of intermediate (86) with an appropriate amine of the formula ArNHR$^4$, for example, using standard basic conditions such as those known in the literature (e.g., in the presence of sodium hydride in DMF or diisopropylethylamine in THF and the like).

In yet another embodiment, the desired compounds of formula (1) wherein Y is $SO_2NR^4$, and Ar, T, U, V, W, X, $R^1$, $R^2$, and $R^3$ are as described in the general description, the dotted lines [---] in the rings represent double bonds, p=0, and n=0-2, can be synthesized as described in the general synthetic scheme below.

Scheme X

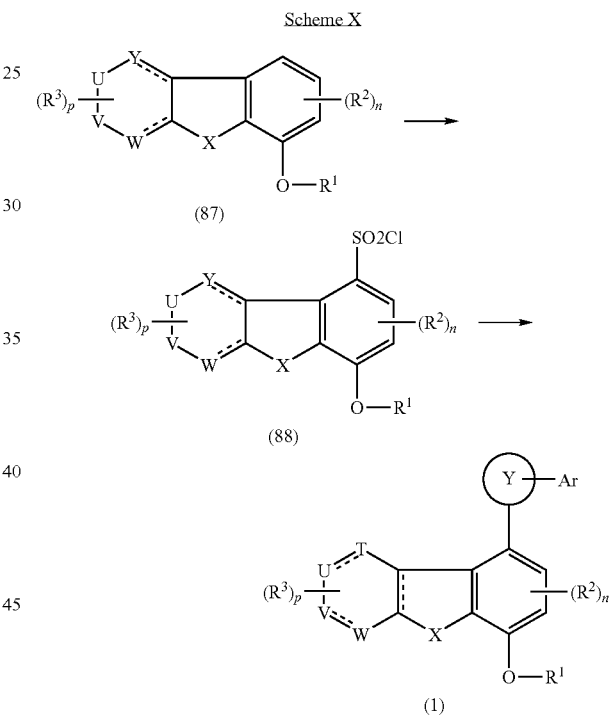

In the above scheme X, the intermediate of formula (87) wherein T, U, V, W, $R^1$, $R^2$, $R^3$, n and p are the same as defined above, can be converted to the intermediate of formula (88), for example with chlorosulphonic acid. The final compounds of formula (1) can be prepared by reacting the intermediate of the formula (88) with an appropriate amine of the formula ArNHR$^4$, for example, using standard basic conditions such as those known in the literature (e.g., in the presence of sodium hydride in DMF or diisopropylethylamine in THF and the like).

In yet another embodiment, the compounds of formula (1) where Y is —NR$^4$SO$_2$ or —NR$^4$CO and Ar, T, U, V, W, X, $R^1$, $R^2$, and $R^3$ are as described in the general description, the dotted lines [---] in the rings represent double bonds, p=0, and n=0-2, can be synthesized using the process described in scheme XI.

In the above scheme IX, the intermediate of formula (82) can be obtained by reduction of the intermediate of formula (77), wherein $R^7$ is unsubstituted or substituted alkyl, unsubstituted or substituted aryl or substituted or substituted arylalkyl. Intermediate (82) can then be treated with the intermediate of formula (83) (wherein U=NR$^a$, S(O)$_m$ or O) which will undergo Fischer-indole cyclization to provide the intermediate of formula (84). Reaction of intermediate (84) with an intermediate of formula $R^b$-G wherein G is a leaving group Scheme XI:

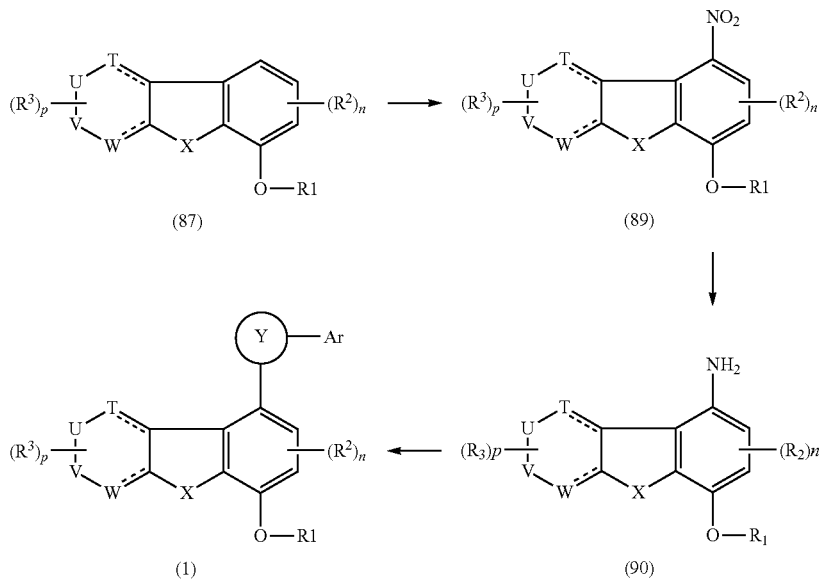

In the above scheme XI, the intermediate of formula (87) wherein T, U, V, W, R$^1$, R$^2$, R$^3$, n and p are the same as defined above, can be converted to the intermediate of formula (89) by treatment with a nitrating mixture such as for example HNO$_3$/H$_2$SO$_4$. The intermediate of formula (89) can then be reduced with a suitable reducing agent (such as H$_2$/Pd/C or Raney-Ni/NH$_2$NH$_2$) to provide the intermediate of formula (90). The final compounds of formula (1) can be prepared by reacting the intermediate of the formula (90) with an appropriate intermediate of the formula ArSO$_2$Cl or ArCOCl for example, using standard basic conditions such as those known in the literature (e.g., in the presence of sodium hydride in DMF or diisopropylethylamine in THF and the like).

The desired compounds of formula (1) obtained by any of the aforementioned schemes can then be converted into their salts and/or the N-oxides and, if desired, salts of the compounds of the formula (1) obtained are then converted into the free compounds. The N-oxidation may be carried out by any manner known in the art, e.g. with the aid of m-chloroperoxybenzoic acid in dichloromethane at room temperature.

The substances according to the invention may be isolated and purified by any method known in the art, e.g., by distilling off the solvent in vacuum and recrystallizing the residue obtained from a suitable solvent or subjecting it to one of the customary purification methods, such as column chromatography on a suitable support material.

Salts can be obtained by dissolving the free compound in a suitable solvent, e.g., in a chlorinated hydrocarbon, such as methylene chloride or chloroform, or a low molecular weight aliphatic alcohol (e.g., ethanol, isopropanol) which contains the desired acid or base, or to which the desired acid or base is then added. The salts can be obtained by filtering, reprecipitating, precipitating with a non-solvent for the addition salt or by evaporating the solvent. Salts obtained can be converted by basification or acidification into the free compounds which, in turn can be converted into salts.

The chlorinated solvent which may be employed may be selected from dichloromethane, 1,2-dichloroethane, chloroform, carbontetrachloride and the like. The aromatic solvents which may be employed may be selected from benzene and toluene. The alcoholic solvents which may be employed may be selected from methanol, ethanol, n-propanol, iso propanol, tert-butanol and the like.

In general, the compounds prepared in the above described processes can be obtained in pure form by using known techniques such as crystallization using solvents such as pentane, diethyl ether, isopropyl ether, chloroform, dichloromethane, ethyl acetate, acetone, methanol, ethanol, isopropanol, water or their combinations, or column chromatography using alumina or silica gel and eluting the column with solvents such as hexane, petroleum ether (pet.ether), chloroform, ethyl acetate, acetone, methanol or their combinations.

Various polymorphs of a compound of formula (1) forming part of this invention may be prepared by crystallization of compound of formula (1) under different conditions. For example, using different solvents commonly used or their mixtures for recrystallization; crystallizations at different temperatures, various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffraction or other techniques.

Pharmaceutical Compositions

The present invention also provides pharmaceutical compositions containing one or more compounds of formula (1) (including derivatives, analogs, tautomeric forms, stereoisomers, polymorphs, enantiomers, and diasteromers) and pharmaceutically acceptable salts thereof (and pharmaceutically acceptable solvates) in combination with a pharmaceutically acceptable excipient, such as a pharmaceutically acceptable carrier or diluent.

The pharmaceutical compositions may be in the form of dosage unit forms, such as tablets, capsules, powders, syrups, solutions, and suspensions and the like. The pharmaceutical compositions may contain suitable solid or liquid carriers or diluents, or be in suitable sterile media to form injectable solutions or suspensions. For oral administration, the compounds of formula (1) can be combined with a suitable solid, liquid carrier or diluent to form capsules, tablets, powders, syrups, solutions, suspensions or the like. The pharmaceutical compositions, may, if desired, contain additional components such as flavorants, sweeteners, excipients and the like. For parenteral administration, the compounds of the formula (1) can be combined with sterile aqueous or organic media to form injectable solutions or suspensions. For example, solutions in sesame or peanut oil, aqueous propylene glycol and the like can be used as well as aqueous solutions of water-soluble pharmaceutically-acceptable acid addition salts or salts with a base of the compounds of formula (1). The injectable solutions prepared in this manner can then be administered intravenously, intraperitoneally, subcutaneously, or intramuscularly.

The compounds can also be administered by inhalation when application within the respiratory tract is intended. For example, the compound of Formula (1) can be delivered by respiratory inhalation in the form of an aerosol under pressure. It is preferred to micronize the compound of Formula (1) after it has been homogenised, e.g., in lactose, glucose, higher fatty acids, sodium salt of dioctylsulfosuccinic acid or, most preferably, in carboxymethyl cellulose, in order to achieve a microparticle size of 5 μm or less for the majority of particles. For the inhalation formulation, the aerosol can be mixed with a gas or a liquid propellant for dispensing the active substance. An inhaler or atomizer or nebulizer may be used. Such devices are known. See, e.g., Newman et al., *Thorax*, 1985, 40:61-676 and Berenberg, M., *J. Asthma USA*, 1985, 22:87-92, both of which are incorporated herein by reference in their entirety. A Bird nebulizer can also be used. See also U.S. Pat. Nos. 6,402,733; 6,273,086; and 6,228,346, incorporated herein by reference in their entirety. The compound of the structure (1) for inhalation is preferably formulated in the form of a dry powder with micronized particles. The compounds of the invention may also be used in a metered dose inhaler using methods disclosed in U.S. Pat. No. 6,131,566, incorporated herein by reference in their entirety.

In addition to the compounds of formula (1) the pharmaceutical compositions of the present invention may also contain or be co-administered with one or more known therapeutic agents.

Methods of Treatment

The pharmaceutical compositions according to this invention can be used for the treatment of allergic disorders.

The compounds of formula (1) down regulate or inhibit the production of TNF-α as they are PDE4 inhibitors and therefore are useful in the treatment of variety of allergic and inflammatory diseases including asthma, chronic bronchitis, atopic dermatitis, urticaria, allergic rhinitis, allergic conjunctivitis, vernal conjunctivitis, eosinophilic granuloma, psoriasis, rheumatoid arthritis, septic shock, diabetes, ulcerative colitis, Crohn's disease, reperfusion injury of the myocardium and brain, chronic glomerulonephritis, endotoxic shock and adult respiratory distress syndrome. The compounds of the present invention are particularly useful for the treatment of asthma and chronic obstructive pulmonary disease (COPD).

Yet another embodiment of the invention is a method of treating an inflammatory disease, disorder or condition characterized by or associated with an undesirable inflammatory immune response, or a disease or condition induced by or associated with an excessive secretion of TNF-α and PDE4 in a subject in need thereof by administering to the subject a therapeutically effective amount of a PDE-4 inhibitor or a pharmaceutical composition of the present invention.

Yet another embodiment of the invention is a method of treating an inflammatory condition or an immune disorder in a subject in need thereof by administering to the subject a therapeutically effective amount of a compound according to formula (I) or a pharmaceutical composition of the present invention. Inflammatory conditions and immune disorders which can be treated with the PDE-4 inhibitors of the present invention include, but are not limited to, asthma, bronchial asthma, chronic obstructive pulmonary disease, allergic rhinitis, eosinophilic granuloma, nephritis, rheumatoid arthritis, cystic fibrosis, chronic bronchitis, multiple sclerosis, Crohn's disease, psoriasis, uticaria, adult vernal conjunctivitis, respiratory distress syndrome, rheumatoid spondylitis, osteoarthritis, gouty arthritis, uvelitis, allergic conjunctivitis, inflammatory bowel conditions, ulcerative coalitis, eczema, atopic dermatitis and chronic inflammation. Preferred inflammatory conditions include, but are not limited to, allergic inflammatory conditions.

Further preferred are inflammatory conditions and immune disorders chosen from inflammatory conditions and immune disorders of the lungs, joints, eyes, bowels, skin or heart.

Further preferred are inflammatory conditions chosen from asthma and chronic obstructive pulmonary disease.

Yet another embodiment of the invention is a method for abating inflammation in an affected organ or tissue by delivering to the organ or tissue a therapeutically effective amount of a PDE-4 inhibitor or a pharmaceutical composition of the present invention.

Yet another embodiment of the invention is a method of treating a disease of the central nervous system in a subject in need thereof by administering to the subject a therapeutically effective amount of a PDE-4 inhibitor or a pharmaceutical composition of the present invention.

Diseases of the central nervous system treatable with the compounds of the present invention include, but are not limited to, depression, amnesia, dementia, Alzheimers disease, cardiac failure, shock and cerebrovascular disease.

Yet another embodiment of the invention is a method of treating insulin resistant diabetes in a subject in need thereof by administering to the subject a therapeutically effective amount of a PDE-4 inhibitor or a pharmaceutical composition of the present invention.

The following examples are illustrative in nature and do not in anyway restrict the actual scope of the invention.

Example 1

N9-(3,5-dichloro-4-pyridyl)-6-methoxybenzo[4,5]furo[2,3-d]pyridazine-9-carboxamide

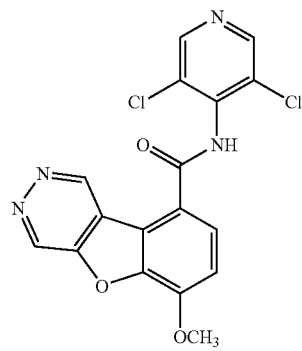

Step 1: ethyl 2-(2-methoxyphenoxy)-3-oxobutanoate

A mixture of guaicol (20.0 g, 186.9 mmol) and sodium hydroxide (8.9 g, 224.4 mmol) in benzene (300 ml) was refluxed for 34 hrs. Then the reaction mixture was cooled to room temperature and 2-chloro ethyl acetoacetate (37 g, 224.4 mmol) was added dropwise. The reaction mixture was stirred at room temp for 24 hrs. Water (300 ml) was added to reaction mixture, acidified with dilute HCl and extracted by ethyl acetate (3×100 ml). The combined organic phases were washed with water (3×100 ml) and dried over anhydrous sodium sulfate. After concentrating the organic extract, the crude mass was purified by silica gel column chromatography using 10% ethyl acetate in petroleum ether. 15.0 g of pure product was obtained as pale yellow oil.

IR (KBr): 3067, 2983, 2942, 2839, 1750, 1730, 1660, 1593, 1500, 1457, 1259, 1206, 1178, 1114, 1092, 1026, 750 cm$^{-1}$.

$^1$H nmr (300 MHz, CDCl$_3$) δ 1.26 (t, 3H), 2.43 (s, 3H), 3.84 (s, 3H), 4.22 (q, 2H), 5.022 (s, 1H), 6.84-7.08 (m, 4H).

Step 2: ethyl 7-methoxy-3-methylbenzo[b]furan-2-carboxylate

Ethyl 2-(2-methoxyphenoxy)-3-oxobutanoate (12.0 g, 47.8 mmol) was added to the polyphosphoric acid at 80-90° C. under stirring. After completion of the reaction, reaction mixture was cooled to room temp and ice (250 g) was added to the reaction mass. The organic mass was extracted by dichloro methane (3×100 ml). The combined organic phases were washed with water (3×100 ml) followed by brine (100 ml) and dried over anhydrous sodium sulfate. After concentrating organic volume, brown colored solid (8.5 g) was obtained.

IR (KBr): 3078, 3061, 3002, 2978, 2931, 2908, 1719, 1586, 1500, 1397, 1384, 1306, 1280, 1182, 1164, 1150, 1047, 1020, 853, 789, 741 cm$^{-1}$.

$^1$H nmr (300 MHz, DMSO-d$_6$) δ 1.34 (t, 3H), 2.53 (s, 3H), 3.95 (s, 3H), 4.36 (q, 2H), 7.12 (dd, 1H, J=7.8, 1.2 Hz), 7.31 (t, 1H, J=7.8 Hz), 7.34 (dd, 1H, J=7.8, 1.2 Hz).

Step 3: ethyl 4-formyl-7-methoxy-3-methylbenzo[b]furan-2-carboxylate

The solution of ethyl 7-methoxy-3-methylbenzo[b]furan-2-carboxylate (5.0 g, 21.3 mmol) in dichloromethane (50 ml) was cooled to −10-0° C. Tin(IV) chloride (11.3 g, 42.7 mmol) was added at once to the reaction mixture at −10-0° C. Then dichloromethyl methyl ether (3.6 g, 31.95 mmol) was added dropwise at the same temp. Water (200 ml) was added to reaction mixture and dichloromethane was distilled off under vacuum. The solid obtained was filtered and suck dried. The solid was purified by column chromatography using 10% ethyl acetate in petroleum ether. 3.3 g of pure product was obtained as pale yellow solid.

IR (KBr): 3051, 2986, 2968, 2937, 2866, 1707, 1680, 1609, 1573, 1463, 1367, 1337, 1287, 1294, 1264, 1166, 1083, 1045, 938, 783 cm$^{-1}$.

$^1$H nmr (300 MHz, DMSO-d$_6$) δ 1.60 (t, 3H), 2.83 (s, 3H), 4.06 (s, 3H), 4.40 (q, 2H), 7.33 (d, 1H, J=8.4 Hz), 7.95 (d, 1H, J=8.7 Hz), 10.23 (s, 1H).

Step 4: 2-ethoxycarbonyl-7-methoxy-3-methylbenzo[b]furan-4-carboxylic acid

The solution of ethyl 4-formyl-7-methoxy-3-methylbenzo[b]furan-2-carboxylate (3.0 g, 11.4 mmol) in acetone (30 ml) was cooled to 10-20° C. Sulfamic acid (1.55 g, 17.1 mmol) was added at once to the reaction mixture at 10-20° C. Then solution of sodium chlorite (1.6 g, 17.1 mmol) in water (10 ml) was added dropwise at the same temp. Water (100 ml) was added to reaction mixture. Acetone was distilled off under vacuum. The solid obtained was filtered and suck dried. Yellow coloured solid (3.0 g) was obtained.

$^1$H nmr (300 MHz, DMSO-d$_6$) δ 1.34 (t, 3H), 2.69 (s, 3H), 4.01 (s, 3H), 4.38 (q, 2H), 7.18 (d, 1H, J=8.4 Hz), 7.82 (d, 1H, J=8.7 Hz), 12.9 (s, 1H).

Step 5: 2-ethyl-4-methyl-7-methoxy-3-methylbenzo[b]furan-2,4-dicarboxylate

A mixture of 2-ethoxycarbonyl-7-methoxy-3-methylbenzo[b]furan-4-carboxylic acid (3.0 g, 10.79 mmol) and potassium carbonate (7.4, 54.0 mmol) in N,N-dimethyl formamide (30 ml) was heated to reflux temp at 80-90° C. Then dimethyl sulfate (4.06 g, 32.3 mmol was added dropwise to the reaction mixture at 80-90° C. Reaction mixture was cooled to room temp. Water (300 ml) was added to reaction mixture and acidified with dilute HCl. The precipitate obtained was filtered and dried in oven. Yellow coloured solid (2.8 g) was obtained.

IR (KBr): 2978, 2937, 1702, 1615, 1573, 1441, 1432, 1342, 1297, 1266, 1240, 1177, 1129, 1083, 1043, 1012, 930, 850, 781 cm$^{-1}$.

$^1$H nmr (300 MHz, DMSO-d$_6$) δ 1.35 (t, 3H), 2.65 (s, 3H), 3.82 (s, 3H), 4.02 (s, 3H), 4.38 (q, 2H), 7.20 (d, 1H, J=8.4 Hz), 7.83 (d, 1H, J=8.4 Hz).

Step 6: 2-ethyl-4-methyl-3-bromomethyl-7-methoxybenzo[b]furan-2,4-dicarboxylate A mixture of 2-ethyl-4-methyl-7-methoxy-3-methylbenzo[b]furan-2,4-dicarboxylate (2.80 g, 9.5 mmol), n-bromo succinimide (2.04 g, 1.1 mmol) and benzoyl peroxide (0.45 g, 1.9 mmol) in carbon tetrachloride (30 ml) was heated to reflux temp at 80-90° C. Water (100 ml) was added to reaction mixture. Organic mass was extracted by dichloromethane (3×50 ml). The combined organic phases were washed with water (3×50 ml) followed by brine (100 ml) and dried over anhydrous sodium sulfate. After concentrating organic volume, 3.2 g of brown coloured solid was obtained.

IR (KBr): 3076, 2984, 2957, 2852, 1727, 1711, 1617, 1574, 1426, 1373, 1272, 1297, 1228, 1193, 1142, 1023, 920, 774, 657 cm$^{-1}$.

$^1$H nmr (300 MHz, DMSO-d$_6$) δ 1.37 (t, 3H), 3.91 (s, 3H), 4.04 (s, 3H), 4.46 (q, 2H), 5.40 (s, 2H), 7.28 (d, 1H, J=8.4 Hz), 7.93 (d, 1H, J=8.4 Hz).

Step 7: 2-ethyl-4-methyl 3-formyl-7-methylbenzo[b]furan-2,4-dicarboxylate

A mixture of potassium iodide (1.71 g, 10.3 mmol), and sodium carbonate (1.82 g, 17.2 mmol) in dimethyl sulfoxide (20 ml) was heated to 80-90° C. under nitrogen. Then 2-ethyl-4-methyl-3-bromomethyl-7-methoxybenzo[b]furan-2,4-dicarboxylate (3.2 g, 8.6 mmol) was added to the reaction mixture at once at the same temp. Reaction mixture was cooled to room temp. and water (200 ml) was added to reaction mixture. Organic mass was extracted by dichloromethane (3×100 ml). The combined organic phases were washed with water (3×100 ml) followed by brine (100 ml) and dried over anhydrous sodium sulfate. After concentrating organic volume under vacuum, the crude mass was purified by column chromatography using 20% ethyl acetate in petroleum ether. 568 mg of pure product was obtained as pale yellow solid.

IR (KBr): 2986, 2960, 1721, 1706, 1615, 1581, 1515, 1434, 1375, 1339, 1280, 1231, 1194, 1178, 1026, 920, 778 cm$^{-1}$.

$^1$H nmr (300 MHz, DMSO-d$_6$) δ 1.35 (t, 3H), 3.80 (s, 3H), 4.06 (s, 3H), 4.42 (q, 2H), 7.31 (d, 1H, J=8.4 Hz), 7.88 (d, 1H, J=8.4 Hz), 10.51 (s, 1H).

Step 8: methyl(6-methoxy-4-oxo-3,4-dihydrobenzo[4,5]furo[2,3-d]pyridazine)-9-carboxylate To a solution of 2-ethyl 4-methyl 3-formyl-7-methylbenzo[b]furan-2,4-dicarboxylate (568 mg, 1.8 mmol) in ethanol (20 ml), hydrazine hydrate (185 mg, 3.7 mmol) was added at room temp. The reaction mixture was stirred at room temp. for 3-4 hrs. Water (100 ml) was added to reaction mixture and the solid obtained was filtered and suck dried. The solid was dried in oven. White colored solid (397 mg) was obtained.

IR (KBr): 3168, 3078, 3006, 2951, 2909, 2347, 1698, 1591, 1281, 1028, 981, 921 cm$^{-1}$.

$^1$H nmr (300 MHz, DMSO-d$_6$) δ 3.93 (s, 3H), 4.10 (s, 3H), 7.41 (d, 1H, J=8.4 Hz), 8.19 (d, 1H, J=8.4 Hz), 9.10 (s, 1H), 13.51 (s, 1H).

Step 9: methyl (4-chloro-6-methoxybenzo[4,5]furo[2,3-d]pyridazine)-9-carboxylate A suspension of methyl 6-methoxy-4-oxo-3,4-dihydrobenzo[4,5]furo[2,3-d]pyridazine-9-carboxylate (396 mg, 1.44 mmol) in phosphorous oxychloride (10 ml) was heated to reflux temp at 120-130° C. Reaction mixture was cooled to 0-10° C. Water (100 ml) was added dropwise to the reaction mixture at 0-10° C. The precipitate obtained was filtered and dried in oven. Yellow colored solid (390 mg) was obtained.

$^1$H nmr (300 MHz, DMSO-d$_6$) δ 4.04 (s, 3H), 4.14 (s, 3H), 7.61 (d, 1H, J=8.4 Hz), 8.24 (d, 1H, J=8.4 Hz), 10.35 (s, 1H).

Step 10: methyl (6-methoxybenzo[4,5]furo[2,3-d]pyridazine)-9-carboxylate

A suspension of methyl 4-chloro-6-methoxybenzo[4,5]furo[2,3-d]pyridazine-9-carboxylate (390 mg, 1.33 mmol), catalytic amount of aqueous ammonia and 10% palladium on carbon (180 mg) in methanol (30 ml) was hydrogenated at 30 psi hydrogen pressure at room temp. Progress of reaction was monitored by TLC. At the end, reaction mixture was filtered through cellite bed. Bed was washed with methanol (3×10 ml). The filtrate was concentrated under vacuum. 210 mg yellow colored solid was obtained.

IR (KBr): 3113, 2950, 2852, 1711, 1624, 1588, 1438, 1301, 1298, 1117, 1021, 979, 842 cm$^{-1}$.

$^1$H nmr (300 MHz, DMSO-d$_6$) δ 4.04 (s, 3H), 4.13 (s, 3H), 7.57 (d, 1H, J=8.4 Hz), 8.22 d, 1H, J=8.4 Hz), 10.01 (s, 1H), 10.40 (s, 1H).

Step 11: 6-methoxybenzo[4,5]furo[2,3-d]pyridazine-9-carboxylic acid

A mixture of methyl 6-methoxybenzo[4,5]furo[2,3-d]pyridazine-9-carboxylate (210 mg, 0.81 mmol) and sodium hydroxide (65 mg, 1.64 mmol) in methanol (20 ml) was heated to reflux temp at 60-70° C. for 3-4 hrs. Reaction mixture was concentrated under vacuum. Then water (50 ml) was added to reaction mixture and acidified with dilute HCl. The precipitate obtained was filtered and dried in oven. 200 mg buff colored solid was obtained.

IR (KBr): 3064, 2943, 2848, 2522, 1696, 1595, 1455, 1277, 1289, 1120, 997 cm$^{-1}$.

$^1$H nmr (300 MHz, DMSO-d$_6$) δ 4.11 (s, 3H), 7.53 (d, 1H, J=8.4 Hz), 8.19 d, 1H, J=8.4 Hz), 9.98 (s, 1H), 10.47 (s, 1H).

Step 12: 4-nitrophenyl 6-methoxybenzo[4,5]furo[2,3-d]pyridazine-9-carboxylate

A mixture of 6-methoxybenzo[4,5]furo[2,3-d]pyridazine-9-carboxylic acid (200 mg, 0.819 mmol), 4-N,N-dimethyl amino pyridine (29 mg, 0.24 mmol), p-nitro phenol (170 mg, 1.22 mmol) and EDCl (233 mg, 1.22 mmol) in dichloromethane (300 ml) was stirred at room temp for 6-7 hrs. Reaction mixture was concentrated under vacuum. Then water (50 ml) was added to reaction mixture and acidified with dilute HCl. The precipitate obtained was filtered and dried in oven. 190 mg buff colored solid was obtained.

IR (KBr): 3109, 2940, 2858, 2346, 1740, 1591, 1517, 1352, 1270, 1217, 1117, 1130, 1013, 975 cm$^{-1}$.

$^1$H nmr (300 MHz, DMSO-d$_6$) δ 4.18 (s, 3H), 7.63 (d, 1H, J=8.4 Hz), 7.78 (d, 2H, J=9.0 Hz), 8.44 (d, 2H, J=9.0 Hz), 8.51 (d, 1H, J=8.4 Hz), 10.04 (s, 1H), 10.31 (s, 1H).

Step 13: N9-(3,5-dichloro-4-pyridyl)-6-methoxybenzo[4,5]furo[2,3-d]pyridazine-9-carboxamide A suspension of 4-nitrophenyl 6-methoxybenzo[4,5]furo[2,3-d]pyridazine-9-carboxylate (70 mg, 0.19 mmol) and 4-amino-3,5-dichloro pyridine (46 mg, 0.28 mmol) in dimethyl formamide (300 ml) was cooled to −10-0° C. under nitrogen Then sodium hydride (15 mg, 0.38 mmol) was added at once at the same temp. under nitrogen. Reaction mixture was cooled to 0-10° C. Water (300 ml) was added dropwise to the reaction mixture at 0-10° C. and acidified with dilute HCl. The precipitate obtained was filtered and dried in oven. The solid was purified by column chromatography using 20% acetone in chloroform. 18 mg pure product was obtained as off white solid.

IR (KBr): 3195, 3045, 3028, 2937, 2842, 2344, 1655, 1596, 1490, 1303, 1286, 1122, 1024, 981, 812 cm$^{-1}$.

$^1$H nmr (300 MHz, DMSO-d$_6$) δ 4.15 (s, 3H), 7.65 (d, 1H, J=8.4 Hz), 8.26 (d, 1H, J=8.4 Hz), 8.84 (s, 2H), 9.99 (s, 1H), 10.21 (s, 1H), 11.04 (s, 1H).

Example 2

N9-(3,5-dichloro-4-pyridyl)-6-methoxybenzo[4,5]furo[3,2-d]pyrimidine-9-carboxamide

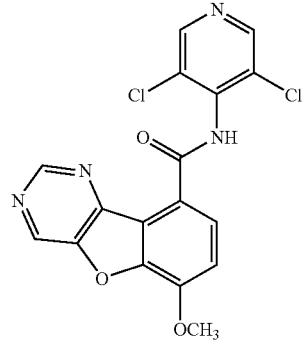

Step 1: ethyl 2-(2-formyl-6-methoxyphenoxy)acetate

A mixture of o-vanillin (5.0 g, 32.9 mmol), ethyl bromoacetate (8.24 g, 49.3 mmol) and potassium carbonate (9.1 g, 65.8 mmol) in N,N-dimethylformamide (50 ml) was heated to 80-90° C. for 3-4 hrs. The reaction mixture was cooled to room temperature. Water (300 ml) was added to reaction mixture and acidified with dilute HCl. The solid obtained was filtered, suck dried and dried in oven. 8.5 g of pure product was obtained as pale yellow solid.

m.p: 65.5-68° C.

IR (KBr): 2997, 2978, 2948, 2914, 1756, 1693, 1587, 1482, 1399, 1380, 1260, 1233, 1173, 1055, 908, 780, 746 $cm^{-1}$.

$^1$H nmr (300 MHz, DMSO-$d_6$) δ 1.17 (t, 3H), 3.86 (s, 3H), 4.13 (q, 2H), 4.88 (s, 1H), 7.31 (t, 1H, J=7.8 Hz), 7.12 (dd, 1H, J=7.8, 1.5 Hz), 7.34 (dd, 1H, J=7.8, 1.5 Hz), 10.51 (s, 1H).

Step 2a: ethyl 2-(2-cyano-6-methoxyphenoxy)acetate

To the mixture of sodium bicarbonate (4.47 g, 53.2 mmol) and hydroxyl amine hydrochloride (2.96 g, 42.6 mmol) in ethanol (30 ml), suspension of ethyl 2-(2-formyl-6-methoxyphenoxy)acetate (8.40 g, 35.5 mmol) in ethanol (50 ml) was added at room temperature under stirring. Water (100 ml) was added to reaction mixture, acidified with dilute HCl and ethanol was distilled off under vacuum. The solid obtained was filtered and suck dried. Pale yellow coloured solid (7.8 g) was obtained m.p. 79-81° C.

IR (KBr): 3256, 2990, 1752, 1582, 1478, 1254, 1224, 1197, 1179, 1060, 966, 783, 744 $cm^{-1}$.

$^1$H nmr (300 MHz, DMSO-$d_6$) δ 1.20 (t, 3H), 3.81 (s, 3H), 4.15 (q, 2H), 4.70 (s, 1H), 7.06 (m, 2H), 7.29 (t, 1H, J=7.8 Hz), 8.50 (s, 1H), 11.25 (s, 1H).

Step 2b

The solution of dimethyl amino pyridine (3.73 g, 30.65 mmol) in dichloromethane (30 ml) was cooled to −10-0° C. Thionyl chloride (7.95 g, 67.39 mmol) was added dropwise to the reaction mixture at −10-0° C. under nitrogen. Then solution of oxime (from step 2a) (7.75 g, 30.63 mmol) in dichloromethane (50 ml) was added dropwise at the same temp under nitrogen. After 15 min. a solution of dimethyl amino pyridine (5.6 g, 45.93 mmol) in dichloro methane (50 ml) was added dropwise. Water (200 ml) was added to reaction mixture and basified with saturated sodium bicarbonate solution Organic mass was extracted by dichloromethane (3×150 ml). The combined organic phases were washed with water (3×150 ml) followed by brine (100 ml) and dried over anhydrous sodium sulfate. After concentrating organic volume, 7.0 g of brown coloured solid was obtained.

m.p. 61-62° C.

IR (KBr): 3082, 2971, 2943, 2843, 2236, 1752, 1579, 1476, 1442, 1381, 1307, 1284, 1263, 1189, 1090, 1071, 1053, 1019, 787, 751 $cm^{-1}$.

$^1$H nmr (300 MHz, DMSO-$d_6$) δ 1.20 (t, 3H), 3.84 (s, 3H), 4.16 (q, 2H), 4.91 (s, 1H), 7.23 (t, 1H, J=7.8 Hz), 7.31 (dd, 1H, J=7.8, 1.5 Hz), 7.40 (dd, 1H, J=7.8, 1.5 Hz).

Step 3: 6-methoxy-3,4-dihydrobenzo[4,5]furo[3,2-d]pyrimidine-4-one

Ethyl 2-(2-cyano-6-methoxyphenoxy)acetate (6.95 g, 29.5 mmol) was heated in formamide (35 ml) at 180-200° C. for 12-14 hrs. Progress of reaction was monitored by TLC. The reaction mixture was cooled to room temperature. Water (100 ml) was added to reaction mixture. The solid obtained was filtered and suck dried. Yellow coloured solid (3.50 g) was obtained.

m.p. 279-282° C.

IR (KBr): 3060, 2970, 2951, 1701, 1604, 1447, 1424, 1311, 1272, 1243, 1207, 1178, 1124, 1065, 994, 900, 801, 764, 728 $cm^{-1}$.

$^1$H nmr (300 MHz, DMSO-$d_6$) δ 4.01 (s, 3H), 7.31 (dd, 1H, J=7.8, 1.5 Hz), 7.42 (t, 1H, J=7.8 Hz), 7.59 (dd, 1H, J=7.8, 1.5 Hz), 8.24 (s, 1H), 12.99 (brs, 1H).

Step 4:
4-chloro-6-methoxybenzo[4,5]furo[3,2-d]pyrimidine

A suspension of 6-methoxy-3,4-dihydrobenzo[4,5]furo[3,2-d]pyrimidine-4-one (3.45 g, 1.44 mmol) in phosphorous oxychloride (30 ml) was heated to reflux temp at 120-130° C. Reaction mixture was cooled to 0-10° C. Water (100 ml) was added dropwise to the reaction mixture at 0-10° C. The precipitate obtained was filtered and dried in oven. Yellow colored solid (3.25 g) was obtained.

m.p. 174.5-176° C.

IR (KBr): 2936, 1638, 1596, 1587, 1543, 1381, 1278, 1134, 1058, 931, 764 $cm^{-1}$.

$^1$H nmr (300 MHz, DMSO-$d_6$) δ 4.06 (s, 3H), 7.65 (m, 2H), 7.80 (dd, 1H, J=7.8, 1.5 Hz), 9.02 (s, 1H).

Step 5: 6-methoxybenzo[4,5]furo[3,2-d]pyrimidine

A suspension of 4-chloro-6-methoxybenzo[4,5]furo[3,2-d]pyrimidine (3.2 g, 13.63 mmol), catalytic amount of aqueous ammonia and 10% palladium on carbon (680 mg) in methanol (40 ml) was hydrogenated at 30 psi hydrogen pressure at room temp. Reaction mixture was filtered through cellite bed. Bed was washed with methanol (3×10 ml). The filtrate was concentrated under vacuum. 2.9 g yellow colored solid was obtained.

m.p. 140-142° C.

IR (KBr): 2923, 1637, 1597, 1584, 1561, 1396, 1293, 1277, 1180, 1098, 1032, 910, 840, 756 $cm^{-1}$.

$^1$H nmr (300 MHz, DMSO-$d_6$) δ 4.04 (s, 3H), 7.50 (m, 2H), 7.80 (dd, 1H, J=7.8, 1.5 Hz), 9.24 (s, 1H), 9.34 (s, 1H).

Step 6:
9-bromo-6-methoxybenzo[4,5]furo[3,2-d]pyrimidine

A mixture of 6-methoxybenzo[4,5]furo[3,2-d]pyrimidine (2.0 g, 10.0 mmol), and iron (0.042 g, 0.82 mmol) in glacial acetic acid was heated to 80-90° C. Then bromine (3.2 g, 20.0 mmol) was added dropwise to the reaction mixture at the same temp. Reaction mixture was cooled to room temp. and Water (100 ml) was added dropwise to the reaction mixture at 0-10° C. The precipitate obtained was filtered, washed with water and dried in oven. Yellow colored solid (2.25 g) was obtained.

pale yellow solid.

m.p. 194-196° C.

IR (KBr): 3056, 2935, 1631, 1586, 1558, 1500, 1455, 1402, 1384, 1286, 1262, 1213, 1093, 1032, 893, 828, 791 $cm^{-1}$.

$^1$H nmr (300 MHz, DMSO-$d_6$) δ 4.03 (s, 3H), 7.40 (d, 1H, J=8.4 Hz), 7.70 (d, 1H, J=8.4 Hz), 9.32 (s, 1H), 9.40 (s, 1H).

Step 7:
6-methoxybenzo[4,5]furo[3,2-d]pyrimidin-9-yl cyanide

A mixture of 9-bromo-6-methoxybenzo[4,5]furo[3,2-d]pyrimidine (1.30 g, 4.66 mmol), and copper (I) cyanide (0.625 g, 6.989 mmol) in N-methylpyrrolidone (10 ml) was heated to 180-190° C. for 34 hrs. The reaction mixture was cooled to room temperature. The reaction mixture was quenched by aqueous solution of $FeCl_3$ (0.625 g), water (50 ml) was added and organic mass was extracted by dichloromethane (6×50 ml). The combined organic phases were washed with water (3×100 ml) followed by brine (100 ml) and dried over anhydrous sodium sulfate. After concentrating organic volume, the crude mass was purified by silica gel column chromatography using 5% ethyl acetate in chloroform. 0.807 g of pure product was obtained as pale yellow solid.

m.p.—decomposes above 268° C.

IR (KBr): 3104, 3019, 2943, 2226, 1628, 1395, 1293, 1190, 1028, 904, 825 $cm^{-1}$.

$^1$H nmr (300 MHz, DMSO-$d_6$) δ 4.13 (s, 3H), 7.62 (d, 1H, J=8.4 Hz), 8.10 (d, 1H, J=8.4 Hz), 9.38 (s, 1H), 9.49 (s, 1H).

Step 8: 6-methoxybenzo[4,5]furo[3,2-d]pyrimidine-9-carboxylic acid

A solution of 6-methoxybenzo[4,5]furo[3,2-d]pyrimidin-9-yl cyanide (600 mg, 2.66 mmol) in 50% sulphuric acid (5 ml $H_2SO_4$+5 ml water) was heated to reflux temp at 140-150° C. Progress of reaction was monitored by TLC. At the end, reaction mixture was cooled to 0-10° C. Water (100 ml) was added dropwise to the reaction mixture at 0-10° C. The precipitate obtained was filtered and dried in oven. The solid was purified by silica gel column chromatography using 10% acetone in chloroform. White colored solid (400 mg) was obtained.

m.p.—decomposes above 280° C.

IR (KBr): 3067, 2918, 2710, 2639, 2517, 1697, 1627, 1579, 1554, 1442, 1384, 1294, 1255, 1123, 1026, 898, 769 $cm^{-1}$.

$^1$H nmr (300 MHz, DMSO-$d_6$) δ 4.13 (s, 3H), 7.55 (d, 1H, J=8.4 Hz), 8.01 (d, 1H, J=8.4 Hz), 9.27 (s, 1H), 9.43 (s, 1H), 13.5 (brs, 1H).

Step 9: 4-nitrophenyl 6-methoxybenzo[4,5]furo[3,2-d]pyrimidine-9-carboxylate A mixture of 6-methoxybenzo[4,5]furo[3,2-d]pyrimidine-9-carboxylic acid (100 mg, 0.409 mmol) and catalytic amount of DMF in thionyl chloride (5 ml) was refluxed for 34 hrs. Thionyl chloride was distilled off under vacuum. To the concentrated mass, tetrahydrofuran (5 ml) was added under nitrogen at room temperature. A solution of p-nitrophenol (85 mg, 0.613 mmol) in tetrahydrofuran (5 ml) was added to reaction mixture under nitrogen at room temperature. Triethyl amine (82 mg, 0.818 mmol) was added at room temperature under nitrogen. Water was added to the reaction mixture at room temperature. The solid obtained was filtered and purified by silica gel column chromatography using 10% ethyl acetate in chloroform buff colored solid (96 mg) was obtained.

m.p.—decomposes above 260° C.

IR (KBr): 2925, 1727, 1627, 1592, 1518, 1392, 1351, 1291, 1265, 1229, 1124, 1024, 900, 873, 806 $cm^{-1}$.

$^1$H nmr (300 MHz, DMSO-$d_6$) δ 4.16 (s, 3H), 7.30 (d, 2H, J=8.7 Hz), 7.80 (d, 2H, J=8.7 Hz), 8.27 (d, 1H, J=8.4 Hz), 8.42 (d, 1H, J=8.4 Hz), 9.32 (s, 1H), 9.48 (s, 1H).

Step 10: N9-(3,5-dichloro-4-pyridyl)-6-methoxybenzo[4,5]furo[3,2-d]pyrimidine-9-carboxamide A suspension of 4-nitrophenyl 6-methoxybenzo[4,5]furo[3,2-d]pyrimidine-9-carboxylate (90 mg, 0.27 mmol) and 4-amino-3,5-dichloro pyridine (66 mg, 0.411 mmol) in dimethyl formamide (10 ml) was cooled to −10-0° C. under nitrogen. Then sodium hydride (21 mg, 0.54 mmol) was added at once at the same temp. under nitrogen. Reaction mixture was cooled to 0-10° C. Water (300 ml) was added dropwise to the reaction mixture at 0-10° C. and acidified with dilute HCl. The precipitate obtained was filtered and dried in oven. The solid was purified by column chromatography using 20% ethyl acetate in chloroform. 25 mg pure product was obtained as off white solid.

m.p.—decomposes above 260° C.

IR (KBr): 3171, 3097, 2919, 2849, 1680, 1622, 1597, 1508, 1400, 1282, 1119, 1022, 903, 806 $cm^{-1}$.

$^1$H nmr (300 MHz, DMSO-$d_6$) δ 4.16 (s, 3H), 7.71 (d, 1H, J=8.4 Hz), 8.37 (d, 1H, J=8.4 Hz), 9.37 (s, 1H), 9.60 (s, 1H), 13.19 (s, 1H).

Example 3

N9-(3,5-dichloro-4-pyridyl)-6-methoxybenzo[4,5]furo[3,2-c]pyridine-9-carboxamide

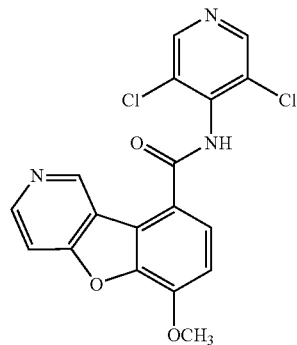

Step 1: 1-methoxy-2-(2-propenyloxy)benzene

To a well stirred solution of guaiacol (10.0 g, 80.55 mmol) and propargyl bromide (11.5 g, 96.66 mmol) in DMF (100 mL) was added anhydrous $K_2CO_3$ (22.0 g, 161.2 mmol) and the mixture was stirred at room temperature for 34 hours. The mixture was then filtered to remove inorganic material. Filtrate was concentrated under vacuo and diluted with water (250 mL). It was then extracted with ethyl acetate (3×100 mL). The combined organic layers were washed with water (2×100 mL) and dried over anhydrous sodium sulfate. Removal of solvent under vacuo gave the product (13.0 g) as brown oil.

IR (Neat): 3438, 2949, 1728, 1619, 1589, 1426, 1291, 1107, 1001, 957, 825, 758 $cm^{-1}$.

$^1$H nmr (300 MHz, $d_6$-DMSO): 2.49 (s, 1H), 3.86 (s, 3H), 4.76 (s, 2H), 6.95 (m, 4H).

Step 2: 7-methoxy-2-methylbenzo[b]furan

To a well stirred solution of 1-methoxy-2-(2-propenyloxy)benzene (from step 1) (13.0 g, 80.24 mmol) in N,N-diethyl aniline (130 mL) was added cesium fluoride (15.85 g, 104 mmol) and the mixture was heated to 215-220° C. for 4-5 hours. Reaction mixture was cooled to room temperature and 10% aqueous HCl solution (1.0 lit) was added followed by addition of ethyl acetate (300 mL). The mixture was the filtered through Celite bed. The organic layer was separated and washed with water (2×100 mL) and dried over anhydrous sodium sulfate. Removal of solvent under vacuo gave crude product (11.0 g) as dark brown oil. It was then purified through silica gel column using petroleum ether: ethyl acetate (9:1) as an eluent to afford the product as pale yellow oil (4.6 g).

IR(Neat): 3440, 2952, 1725, 1627, 1599, 1421, 1285, 1118, 1005, 951, 818, 748 cm$^{-1}$.

$^1$H nmr (300 MHz, d$_6$-DMSO): 2.47 (s, 3H), 4.00 (s, 3H), 6.36 (s, 1H), 7.06 (m, 3H).

Step 3:
7-methoxy-2-methylbenzo[b]furan-4-carboxaldehyde

To a well stirred solution of 7-methoxy-2-methylbenzo[b]furan (from step 2) (6.5 g, 40.07 mmol) in DCM (70.0 mL) was added stannous chloride (17.7 g, 68.26 mmol) followed by slow addition of 1,1-dichloromethyl methyl ether (4.6 g, 40.07 mmol) at −10-0° C. and stirred for 1-2 hrs. Ice cold water (100 mL) was added with vigorous stirring, the organic layer was separated and washed with water (2×50 mL) and dried over anhydrous sodium sulfate. Removal of solvent gave crude product (7.0 g). The crude product was purified by silica gel column using petroleum ether:ethyl acetate (9:1) as an eluent to afford the product as pale yellow oil (2.3 g).

m.p. 167-170° C.

IR (Neat): 3468, 3017, 1741, 1677, 1595, 1512, 1399, 1242, 1175, 1098, 937, 755 cm$^{-1}$.

$^1$H nmr (300 MHz, d$_6$-DMSO): δ 2.50 (s, 3H), 4.03 (s, 3H), 7.09 (d, 1H, J=8.1 Hz), 7.12 (s, 1H), 7.81 (d, 1H, J=8.4 Hz), 10.00 (s, 1H).

Step 4:
7-methoxy-2-methylbenzo[b]furan-4-carboxylic acid

To a well stirred solution of 7-methoxy-2-methylbenzo[b]furan-4-carboxaldehyde (from step 3) (4.0 g, 21.05 mmol) in acetone (40.0 mL) was added a solution of sulphamic acid (2.4 g, 25.26 mmol) in water (10.0 mL) followed by addition of a solution of sodium chlorite (2.8 g, 31.57 mmol) at 5-10° C. Ice cold water (250 mL) was added to reaction mixture and the product separated was filtered and dried at 60-70° C. to give intermediate-4 (3.2 g) as white solid.

m.p. 228-233° C.

IR (Neat) 3400, 1681, 1577, 1449, 1227, 1185, 1096, 966 cm$^{-1}$.

$^1$H nmr (300 MHz, d$_6$-DMSO) δ 2.47 (d, 3H, J=9.6 Hz), 3.98 (s, 3H), 6.93 (d, 1H, J=9.0 Hz), 6.96 (s, 1H), 7.81 (d, 1H, J=8.4 Hz), 12.66 (bs, 1H).

Step 5: Methyl-7-methoxy-2-methylbenzo[b]furan-4-carboxylate

To a well stirred suspension of 7-methoxy-2-methylbenzo[b]furan-4-carboxylic acid (from step 4) (4.5 g, 24.21 mmol) and powdered potassium carbonate (7.5 g, 54.61 mmol) in acetone (740.0 mL) was added dimethyl sulfate (4.1 g, 32.76 mmol) and refluxed for 2-3 hours. Reaction mixture was cooled to room temperature and water (500 mL) was added to it. The organic material separated was extracted with ethyl acetate (3×100 ml). The combined organic layers were washed with water ((2×100 mL) and dried over anhydrous sodium sulfate. Removal of solvent under vacuo gave product (4.0 g) as brown viscous oil.

m.p. 127-129° C.

IR (Neat): 3435, 1625, 1511, 1434, 1281, 1129, 1096, 940, 772 cm$^{-1}$.

$^1$H nmr (300 MHz, d$_6$-DMSO) δ 2.48 (d, 3H, J=9.6 Hz), 3.86 (s, 3H), 3.99 (s, 1H), 6.97 (d, 1H, J=9.0 Hz), 6.99 (s, 1H), 7.83 (d, 1H, J=8.4 Hz).

Step 6: Methyl-2-bromomethyl-7-methoxybenzo[b]furan-4-carboxylate

To a well stirred refluxing solution of AIBN (40.0 mg, 1.0%) and N-bromo succinimide (3.4 g, 19.05 mmol) in carbon tetrachloride (60.0 mL) was added a Methyl-7-methoxy-2-methylbenzo[b]furan-4-carboxylate (from step 5) (4.0 g, 18.16 mmol) and refluxed for 2-3 hours. Reaction mixture was cooled to room temperature and filtered thorough Celite bed. The filtrate was concentrated under vacuo to give product (3.1 g) as brown oil. The product obtained was taken ahead for next step without further purification.

Step 7: Methyl-2-formyl-7-methoxybenzo[b]furan-4-carboxylate

To a well stirred solution of Methyl-2-bromomethyl-7-methoxybenzo[b]furan-4-carboxylate (step 6) (3.1 g, 10.36 mmol) in dimethyl sulfoxide (30.0 mL) was added powdered sodium carbonate (1.64 g, 15.55 mmol) at 90-95° C. and stirred for 2-3 hours. Reaction mixture was cooled to room temperature and diluted with water (300 mL) and extracted with ethyl acetate (3×100 mL). The combined organic layers were washed with water (2×50 mL) and dried over anhydrous sodium sulfate. Removal of solvent gave crude product (2.9 g) as brown viscous oil. Purification by silica gel column using chloroform: ethyl acetate (95:5) as an eluent afforded 2.2 g of pure product.

m.p. 139-142° C.

IR (Neat): 3429, 1711, 1688, 1593, 1432, 1307, 1280, 1123, 1020, 973, 831, 737 cm$^{-1}$.

$^1$H nmr (300 MHz, d$_6$-DMSO) δ 3.92 (s, 3H), 4.06 (s, 1H), 7.32 (d, 1H, J=9.0 Hz), 8.03 (d, 1H, J=8.4 Hz), 8.24 (s, 1H), 9.94 (s, 1H).

Step 8: (Z)-3-(7-methoxy-4-methyloxycarbonyl-benzo[b]furan-2-yl)-2-propenoic acid To a well stirred solution of Methyl-2-formyl-7-methoxybenzo[b]furan-4-carboxylate (from step 7) (2.0 g, 8.53 mmol) in toluene (50.0 mL) was added malonic acid (1.33 g, 12.80 mmol) and Piperidine (0.5 ml). The reaction mixture was then refluxed for 3-4 hours. Reaction mixture was cooled to room temperature, acidified with 10% aqueous HCl solution and extracted with ethyl acetate (2×100 mL). The combined organic layers were washed with water (2×100 mL) and dried over anhydrous sodium sulfate. Removal of solvent under vacuo gave product (1.8 g) as light yellow solid.

m.p. 175-178° C.

IR (Neat): 3435, 1716, 1630, 1509, 1404, 1335, 1289, 1215, 1145, 1031, 951, 757 cm$^{-1}$.

$^1$H nmr (300 MHz, d$_6$-DMSO) δ 3.88 (s, 3H), 4.04 (s, 1H), 6.50 (s, 1H, J=15.9 Hz), 7.15 (d, 1H, J=5.7 Hz), 7.66 (d, 1H, J=15.6 Hz), 7.92 (d, 1H, J=8.4 Hz), 12.75 (bs, 1H).

Step 9: Methyl-2-[(Z)-2-azidocarbonyl)-1-ethenyl]-7-methoxybenzo[b]furan-4-carboxylate To a well stirred solution of (Z)-3-(7-methoxy-4-methyloxycarbonylbenzo[b]furan-2-yl)-2-propenoic acid (from step 8) (1.6 g, 5.79 mmol) and triethyl amine (1.0 mL) in dichloromethane (15 mL) was added a solution ethyl chloroformate (940 mg, 8.68 mmol) in dichloromethane (5.0 mL) at −10° C. and stirred for 2-3 hours. Water (50.0 mL) was added to reaction mixture; the organic phase was separated and dried over anhydrous sodium sulfate. Removal of solvent under vacuo gave intermediate-9 as oily residue (1.5 g). To a well stirred solution of this residue (1.5 g, 4.31 mmol) in acetone (15.0 mL) was added a solution of sodium azide (1.0 g, 15.38 mmol) in water (5.0 mL) at 5-10° C. and stirred for 2-3 hours. Reaction mixture was diluted with cold water (100 mL) and filtered to give the azido intermediate as yellow solid (1.3 g).

Step 10: Methyl-1-hydroxy-6-Methoxybenzo[4,5]furo[3,2-c]pyridine-9-carboxylate To a well stirred refluxing solution of tri-n-butyl amine (2.0 mL) in diphenyl ether (25.0 mL) was added a solution of Methyl-2-[(Z)-2-azidocarbonyl)-1-ethenyl]-7-methoxy-benzo[b]furan-4-carboxylate (from step 9) (1.3 g) in diphenyl ether (50.0 mL) and refluxed for 1-1.5 hours. The excess of diphenyl ether was removed under vacuo and the residue obtained was triturated with petroleum ether (3×25 mL) to give intermediate-11 as yellow solid (1.1 g).

m.p. 205-207° C.

IR (Neat): 3434, 1715, 1661, 1516, 1433, 1287, 1215, 1117, 1014, 755 cm$^{-1}$.

$^1$H nmr (300 MHz, d$_6$-DMSO): δ 3.81 (s, 3H), 4.01 (s, 1H), 6.79 (d, 1H, J=6.9 Hz), 7.16 (d, 1H, J=8.4 Hz), 7.46 (d, 1H, J=8.4 Hz), 7.61 (d, 1H, J=6.9 Hz), 11.57 (bs, 1H).

Step 11: Methyl-1-chloro-6-Methoxybenzo[4,5]furo[3,2-c]pyridine-9-carboxylate A solution of Methyl-1-hydroxy-6-Methoxybenzo[4,5]furo[3,2-c]pyridine-9-carboxylate (from step 10) (1.1 g) and phosphorous oxychloride (25 mL) was refluxed for 15-16 hours. Excess of phosphorous oxychloride was removed under vacuo. The residue obtained was diluted with water (10.0 mL) and made alkaline with solid sodium carbonate. The solid separated was filtered, washed with water and dried to get crude intermediate-12 (1.0 g) as brown solid. Purification by silica gel column using chloroform: ethyl acetate (9:1) as an eluent gave pure intermediate-12 (350 mg) as light yellow solid m.p. 195-197° C.

IR (cm$^{-1}$): 1718, 1668, 1507, 1421, 1271, 1223, 1109, 1001, 756 cm$^{-1}$.

$^1$H nmr (300 MHz, d$_6$-DMSO): δ 3.89 (s, 3H), 4.06 (s, 1H), 7.43 (d, 1H, J=8.4 Hz), 7.65 (d, 1H, J=8.4 Hz), 7.95 (d, 1H, J=5.4 Hz), 8.55 (d, 1H, J=5.4 Hz).

Step 12: Methyl-6-Methoxybenzo[4,5]furo[3,2-c]pyridine-9-carboxylate

A mixture of Methyl-1-chloro-6-Methoxybenzo[4,5]furo[3,2-c]pyridine-9-carboxylate (from step 11) (330 mg), 10% Pd on carbon (50 mg), triethyl amine (2.0 mL) and DMF (10.0 mL) was hydrogenated in a Parr apparatus at 50-55 psi of Hydrogen gas. Catalyst was removed by filtration and filtrate was concentrated under vacuo. The residue obtained was purified by silica gel column using chloroform:acetone (8:2) as an eluent to afford intermediate-13 (200 mg) as light yellow solid.

m.p. 210-213° C.

IR(Neat): 1718, 1672, 1518, 1431, 1272, 1218, 1113, 1011, 755 cm$^{-1}$.

$^1$H nmr (300 MHz, d$_6$-DMSO): δ 4.00 (s, 3H), 4.09 (s, 1H), 7.41 (d, 1H, J=8.4 Hz), 7.89 (d, 1H, J=5.7 Hz), 8.13 (d, 1H, J=9.0 Hz), 8.73 (d, 1H, J=5.4 Hz), 9.94 (s, 1H).

Step 13: 6-Methoxybenzo[4,5]furo[3,2-c]pyridine-9-carboxylic acid

A mixture of Methyl-6-Methoxybenzo[4,5]furo[3,2-c]pyridine-9-carboxylate (from step 12) (200 mg, 0.77 mmol), methanol (5.0 mL) and sodium hydroxide (160 mg, 3.88 mmol) was refluxed for 2-3 hours. Excess of methanol was removed under reduced pressure; the residue was diluted with water (5.0 mL) and acidified to pH 5-6 with acetic acid. The solid obtained was filtered and dried to afford intermediate 14 (130 mg) as off-white solid.

m.p. >260° C.

IR (Neat): 3433, 2075, 1634, 1288, 1219, 1115, 1017, 771 cm$^{-1}$.

$^1$H nmr (300 MHz, d$_6$-DMSO): δ 4.19 (s, 3H), 7.41 (d, 1H, J=8.4 Hz), 7.89 (d, 1H, J=5.7 Hz), 8.13 (d, 1H, J=9.0 Hz), 8.73 (d, 1H, J=5.4 Hz), 10.12 (s, 1H), 12.8 (bs, 1H).

Step 14: 4-Nitrophenyl-6-methoxybenzo[4,5]furo[3,2-c]pyridine-9-carboxylate

A mixture of 6-Methoxybenzo[4,5]furo[3,2-c]pyridine-9-carboxylic acid (from step 13) (65 mg, 0.178 mmol), p-nitrophenol (37 mg, 0.267), EDCl (51 mg, 0.267 mmol), 4,4-dimethyl amino pyridine (2.0 mg, 0.07 mmol) in DMF (3.0 mL) was heated to 70-75° C. for 4-5 hours. The residue obtained after removal of solvent under vacuo was triturated with water (5.0 mL) to give intermediate-15 (55 mg) as yellow solid.

m.p. >250° C.

IR (cm$^{-1}$): 3433, 2075, 1634, 1534, 1318, 1276, 1223, 1109, 1013, 776 cm$^{-1}$.

$^1$H nmr (300 MHz, d$_6$-DMSO): δ 4.14 (s, 3H), 7.51 (d, 1H, J=8.4 Hz), 7.76 (d, 2H, J=8.4 Hz), 7.92 (d, 1H, J=5.7 Hz), 8.41 (m, 3H), 8.73 (d, 1H, J=5.4 Hz), 9.87 (s, 1H).

Step 15: N9-(3,5-dichloro-4-pyridyl)-6-methoxybenzo[4,5]furo[3,2-c]pyridine-9-carboxamide To a well stirred solution of 4-nitrophenyl-6-methoxybenzo[4,5]furo[3,2-c]pyridine-9-carboxylate (from step 14) (55 mg, 0.15 mmol) and 4-amino-3,5-dichloropyridine (50 mg, 0.30 mmol) in DMF (2.0 mL) was added sodium hydride (60% dispersion in mineral oil) (18 mg, 0.45 mmol) at −5° C. and stirred for 3040 minutes. Excess of DMF was removed under reduce pressure, the residue obtained was diluted with water (5 mL) and acidified to pH 5-6 with acetic acid. The solid obtained was filtered, washed with water and dried to afford product (27 mg) as off-white solid.

m.p. >260° C.

IR (Neat): 3434, 1657, 1631, 1559, 1494, 1394, 1287, 1179, 1097, 892, 771 cm$^{-1}$.

$^1$H nmr (300 MHz, d$_6$-DMSO): δ 4.11 (s, 3H), 7.48 (d, 1H, J=8.4 Hz), 7.86 (d, 2H, J=5.4 Hz), 8.08 (d, 1H, J=8.4 Hz), 7.70 (d, 1H, J=5.4 Hz), 8.82 (s, 2H), 9.67 (s, 1H), 10.93 (s, 1H).

Example 4

N9-(3,5-dichloro-4-pyridyl)-6-difluoromethoxy-benzo[4,5]furo[2,3-d]pyridazine-9-carboxamide

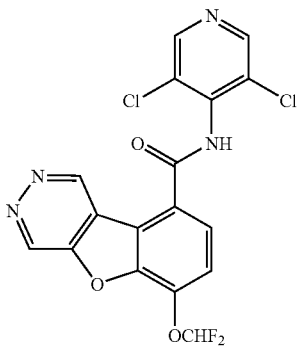

Step 1: 2-ethoxycarbonyl-7-hydroxy-3-methylbenzo[b]furan-4-carboxylic acid

The solution of 2-ethyl-4-methyl-7-methoxy-3-methylbenzo[b]furan-2,4-dicarboxylate (from step 5 of example 1) (13.0 g), sodium p-thiocresolate (20.26 g, 1.5 equiv.) and hexamethylphosphoric acid triamide (24.80 g, 1.5 equiv.) was heated in dry toluene at reflux temperature under nitrogen for 2-6 h. The reaction mixture was cooled to room temperature, water was added and aqueous layer was washed with dichloromethane. Aqueous layer was acidified at 10-15° C. with concentrated hydrochloric acid. The precipitated product was filtered and dried.
m.p.—above 270° C.

Step 2: 2,4-Diethyl-7-hydroxy-3-methylbenzo[b]furan-2,4-dicarboxylate

The solution of 2-ethoxycarbonyl-7-hydroxy-3-methylbenzo[b]furan-4-carboxylic acid (from step 1) (13 g), conc.$H_2SO_4$ in ethanol was heated to reflux temperature. Progress of reaction was monitored by TLC. At the end, reaction mixture was concentrated under vacuum. Then water (500 ml) was added to reaction mixture and the precipitate obtained was filtered and dried in oven. The crude solid was purified by silica gel column chromatography using 20% ethyl acetate in chloroform as eluent. 6.5 g buff colored solid was obtained.
m.p.—195-197° C.

Step 3: 2,4-Diethyl-7-difluoromethoxy-3-methylbenzo[b]furan-2,4-dicarboxylate A mixture of 2,4-Diethyl-7-hydroxy-3-methylbenzo[b]furan-2,4-dicarboxylate (from step 2) (6.50 g) and potassium carbonate (7.2 g) in N,N-dimethyl formamide (70 ml) was heated to reflux temp at 80-90° C. Then chlorodifluoromethane gas was bubbled into the reaction mixture at 80-90° C. Progress of reaction was monitored by TLC. At the end, reaction mixture was cooled to room temperature. Then water (300 ml) was added to reaction mixture and acidified with dilute hydrochloric acid. The precipitate obtained was filtered and dried in oven at 40-45° C. Buff colored solid (6.5 g) was obtained.
m.p.—74-78° C.

Step 4: Diethyl 3-bromomethyl-7-difluoromethoxy-benzo[b]furan-2,4-dicarboxylate This compound was synthesized from 2,4-diethyl-7-difluoromethoxy-3-methylbenzo[b]furan-2,4-dicarboxylate by the procedure described in step 6 of example 1.
m.p.—78-84° C.
IR (KBr):—3080, 2987, 2929, 1719, 1623, 1578, 1508, 1421, 1378, 3131, 1271, 1226, 1155, 1104, 1049, 966, 778, 746 cm$^{-1}$.
$^1$H nmr (300 MHz, DMSO-$d_6$):—δ 1.38 (t, 6H), 4.44 (m, 4H), 5.37 (s, 1H), 7.53 (d, 1H, J=8.1 Hz), 7.57 (t, 1H, J=72.6 Hz), 7.93 (d, 1H, J=8.7 Hz).

Step 5: Diethyl 7-difluoromethoxy-3-formyllbenzo[b]furan-2,4-dicarboxylate

This compound was synthesized from diethyl 3-bromomethyl-7-difluoromethoxybenzo[b]furan-2,4-dicarboxylate by the procedure described in step 7 of example 1.
m.p.—71-74° C.
IR (KBr):—3386, 2992, 2887, 1726, 1701, 1621, 1587, 1513, 1380, 1300, 1284, 1224, 1187, 1084, 1053, 959, 779, 732 cm$^{-1}$.
$^1$H nmr (300 MHz, DMSO-$d_6$):—δ 1.29 (t, 3H), 1.37 (t, 3H), 4.31 (q, 2H), 4.46 (q, 2H), 7.56 (d, 1H, J=8.7 Hz), 7.59 (t, 1H, J=72.6 Hz), 7.86 (d, 1H, J=8.7 Hz), 10.55 (s, 1H).

Step 6: Ethyl 6-difluoromethoxy-4-oxo-3,4-dihydrobenzo[4,5]furo[2,3-d]pyridazine-9-carboxylate This compound was synthesized from diethyl 7-difluoromethoxy-3-formyllbenzo[b]furan-2,4-dicarboxylate as per the procedure described in step 8 of example 1.
m.p.—210-214° C.
IR (KBr):—3171, 2984, 1720, 1673, 1593, 1477, 1374, 1286, 1198, 1095, 1041, 891, 757 cm$^{-1}$.
$^1$H nmr (300 MHz, DMSO-$d_6$):—δ 1.4 (t, 3H), 4.47 (q, 2H), 7.64 (t, 1H, J=72 Hz), 7.69 (d, 1H, J=8.4 Hz), 8.19 (d, 1H, J=8.4 Hz), 9.09 (s, 1H), 13.6 (s, 1H).

Step 7: Ethyl 4-chloro-6-difluoromethoxybenzo[4,5]furo[2,3-d]pyridazine-9-carboxylate This compound was synthesized from ethyl 6-difluoromethoxy-4-oxo-3,4-dihydrobenzo[4,5]furo[2,3-d]pyridazine-9-carboxylate by the procedure described in step 9 of example 1.
m.p.—185-188° C.
IR (KBr):—3098, 2994, 1715, 1635, 1593, 1578, 1427, 1383, 1337, 1283, 1162, 1140, 1090, 945, 846, 790 cm$^{-1}$.
$^1$H nmr (300 MHz, DMSO-$d_6$):—δ 1.44 (t, 3H), 4.54 (q, 2H), 7.69 (t, 1H, J=72.3 Hz), 7.84 (d, 1H, J=8.4 Hz), 8.28 (d, 1H, J=8.7 Hz), 10.35 (s, 1H).

Step 8: Ethyl 6-difluoromethoxybenzo[4,5]furo[2,3-d]pyridazine-9-carboxylate This compound was synthesized from ethyl 4-chloro-6-difluoromethoxybenzo[4,5]furo[2,3-d]pyridazine-9-carboxylate as per the procedure described in step 10 of example 1.
m.p.—148-152° C.
IR (KBr):—3051, 2993, 1718, 1633, 1596, 1447, 1405, 1283, 1201, 1121, 1081, 981, 792 cm$^{-1}$.

$^1$H nmr (300 MHz, DMSO-d$_6$):—δ 1.44 (t, 3H), 4.54 (q, 2H), 7.66 (t, 1H, J=72 Hz), 7.78 (d, 1H, J=8.4 Hz), 8.24 (d, 1H, J=8.4 Hz), 10.09 (s, 1H), 10.41 (s, 1H).

Step 9: 6-Difluoromethoxybenzo[4,5]furo[2,3-d]pyridazine-9-carboxylic acid

This compound was synthesized from ethyl 6-difluoromethoxybenzo[4,5]furo[2,3-d]pyridazine-9-carboxylate by the procedure described in step 11 of example 1.
m.p.—above 270° C.
IR (KBr):—3046, 2927, 2789, 2497, 1874, 1710, 1630, 1596, 1455, 1280, 1134, 1081, 982, 783, 735 cm$^{-1}$.
$^1$H nmr (300 MHz, DMSO-d$_6$):—δ 7.65 (t, 1H, J=72.3 Hz), 7.76 (d, 1H, J=8.4 Hz), 8.22 (d, 1H, J=8.4 Hz), 10.08 (s, 1H), 10.47 (s, 1H).

Step 10: 4-nitrophenyl 6-difluoromethoxybenzo[4,5]furo[2,3-d]pyridazine-9-carboxylate This compound was synthesized from 6-difluoromethoxybenzo[4,5]furo[2,3-d]pyridazine-9-carboxylic acid by the procedure described in step 12 of example 1.
IR (KBr):—3109, 3067, 2928, 1749, 1616, 1590, 1348, 1273, 1199, 1164, 1136, 1070, 972, 883, 861, 744 cm$^{-1}$.
$^1$H nmr (300 MHz, DMSO-d$_6$):—δ 7.75 (t, 1H, J=72 Hz), 7.81 (d, 1H, J=6.9 Hz), 7.89 (d, 1H, J=8.7 Hz), 8.44 (d, 1H, J=6.9 Hz), 8.54 (d, 1H, J=8.7 Hz), 10.14 (s, 1H), 10.31 (s, 1H).

Step 11: N9-(3,5-dichloro-4-pyridyl)-6-difluoromethoxybenzo[4,5]furo[2,3-d]pyridazine-9-carboxamide This compound was synthesized from 4-nitrophenyl 6-difluoromethoxybenzo[4,5]furo[2,3-d]pyridazine-9-carboxylate by the procedure described in step 13 of example 1.
m.p.—above 270° C.
IR (KBr):—3233, 3034, 2923, 2358, 1660, 1599, 1555, 1495, 1289, 11291082, 982, 855, 810 cm$^{-1}$.
$^1$H nmr (300 MHz, DMSO-d$_6$):—δ 7.65 (t, 1H, J=72.6 Hz), 7.89 (d, 1H, J=8.4 Hz), 8.24 (d, 1H, J=8.4 Hz), 8.84 (s, 1H), 10.08 (s, 1H), 10.17 (s, 1H), 11.26 (s, 1H).

Example 5

N9-(3,5-dichloro-4-pyridyl)-6-difluoromethoxybenzo[4,5]furo[2,3-d]pyridazine-9-carboxamide sodium salt

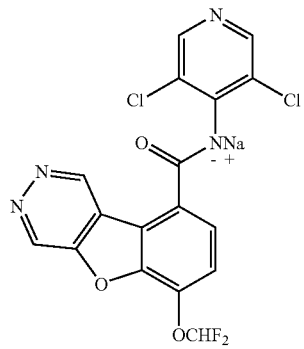

To the suspension of N9-(3,5-dichloro-4-pyridyl)-6-difluoromethoxybenzo[4,5]furo[2,3-d]pyridazine-9-carboxamide (example 4) (70 mg, 0.19 mmol) in THF, sodium hydride (15 mg, 0.38 mmol) was added at once at the same temperature under nitrogen. Progress of reaction was monitored by IR. At the end, reaction mixture was concentrated under vacuum.
IR (KBr):—3101, 2928, 1633, 1581, 1551, 1533, 1446, 1388, 1284, 1203, 1117, 1092, 1043, 994, 855, 810 cm$^{-1}$.
$^1$H nmr (300 MHz, DMSO-d$_6$):—δ 7.50 (t, 1H, J=73.2 Hz), 7.61 (d, 1H, J=8.1 Hz), 8.24 (d, 1H, J=8.7 Hz), 8.26 (s, 1H), 9.92 (s, 1H), 10.87 (s, 1H).

Example 6

2-ethyl-5-(4-nitrophenyl)-8-methoxy-1,2,3,4-tetrahydrobenzo[4,5]thieno[2,3-c]pyridine-2,5-dicarboxylate

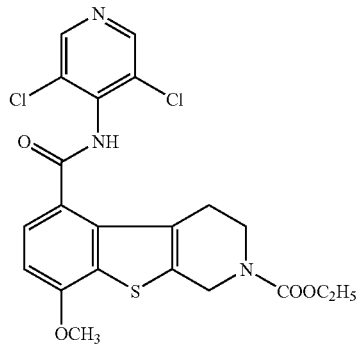

Step 1: ethyl 4-(2-methoxyphenylsulfanyl)-3-oxobutanoate

To a solution of 2-Methoxythiol (5.0 g, 3.57 mmol) in DMF (50 ml) was added potassium carbonate (6.29 g, 4.28 mmol), 4-chloroethylacetoacetate (6.44 g, 3.39 mmol) and stirred at room temperature for 12.0 hours. Water (100 ml) was added to the reaction mixture and extracted with ethyl acetate (3×125 ml). The combined ethyl acetate layers were washed with water (2×50 ml), dried over anhydrous sodium sulfate and concentrated under vacuum to give product as of yellow solid (6.0 g)
IR (KBr) 3061, 3070, 2905, 2838, 1725, 1628, 1595, 1570, 1408, 1309, 1263, 1176, 1027, 941, 839 cm$^{-1}$.
$^1$H nmr (300 MHz, DMSO-d$_6$) δ 1.1 (t, 3H), 3.75 (s, 2H), 3.81 (s, 3H), 3.96 (s, 1H), 4.06 (q, 2H, J=9.0 Hz), 6.88 (t, 1H, J=9.0 Hz), 6.98 (d, 1H, J=6.0 Hz), 7.17 (t, 1H, J=6.0 Hz), 7.21 (d, 1H).

Step 2: ethyl 2-(7-methoxybenzene[b]thiophen-3-yl)acetate

Ethyl 4-(2-methoxyphenylsulfanyl)-3-oxobutanoate (from step 1) (5 g, 1.86 mmol) was added to the polyphosphoric acid at 80-90° C. under stirring. Progress of reaction was monitored by TLC. After completion of the reaction, reaction mixture was cooled to room temp and ice (250 g) was added to the reaction mass. The organic mass was extracted by dichloromethane (3×100 ml). The combined organic phases were washed with water (3×100 ml) followed by brine (100 ml) and dried over anhydrous sodium sulfate. After concentrating organic volume purified on a silica column in pet ether: ethyl acetate (3%) to get pure product as of yellow solid (2.0 g).

IR (KBr) 3091, 3070, 2979, 2937, 2838, 1728, 1686, 1570, 1533, 1475, 1368, 1307, 1263, 1176, 1151, 1027, 941, 839, 784, 716 cm$^{-1}$.

$^1$H nmr (300 MHz, DMSO-d$_6$) δ 1.1 (t, 3H), 3.91 (s, 2H), 3.95 (s, 3H), 4.08 (q, 2H, J=9.0 Hz), 6.94 (d, 1H, J=6.0 Hz), 7.35 (t, 1H, J=6.0 Hz), 7.37 (d, 1H, J=6.0 Hz), 7.58 (s, 1H).

Step 3:
2-(7-methoxybenzene[b]thiophen-3-yl)acetamide

Ethyl 2-(7-methoxybenzene[b]thiophen-3-yl)acetate (from step 2) (2.0 g, 8.0 mmol) was dissolved in Methanol (10 ml) and to the solution added Ethylene glycol saturated with ammonia (10 ml) stirred at room temperature for 48.0 hours. Methanol was evaporated under vacuum Water (50 ml) was added to the reaction mixture and extracted with ethyl acetate (3×25 ml). The combined ethyl acetate layers were washed with water (2×50 ml), dried over anhydrous sodium sulfate and concentrated under vacuum to give product which was washed with pentane (2×25 ml) to get off-white solid (1.2 g).

IR (KBr) 3377, 3188, 2998, 2948, 2832, 1658, 1624, 1566, 1534, 1474, 1458, 1415, 1395, 1280, 1258, 1220, 1054, 935, 878, 778, 651. cm$^{-1}$.

$^1$H nmr (300 MHz, DMSO-d$_6$) δ 3.60 (s, 2H), 3.95 (s, 3H), 6.94 (d, 1H, J=6.0 Hz), 7.18 (t, 1H, J=9.0 Hz), 7.20 (d, 1H, J=6.0 Hz), 7.25 (s, 1H), 7.30 (s broad, 2H).

Step 4:
2-(7-methoxybenzene[b]thiophen-3-yl)ethylamine 2-(7-methoxybenzene[b]thiophen-3-yl)acetamide (from step 3) (1.0 g, 4.52 mmol) was dissolved in THF (20 ml) and heated to 80 C. under heating borane in THF (0.89 ml, 9.04 mmol) was added drop wise and stirred for 3 hours. Acidified with dilute hydrochloric acid (1.0 ml) THF was evaporated under vacuum and then basified with sodium hydroxide (2 ml) solution and extracted with diethyl ether (3×10 ml). The combined ethereal layers were washed with water (2×50 ml), dried over anhydrous sodium sulfate and concentrated under vacuum to give product to that ethyl acetate saturated with hydrochloric acid was added and precipitated solid was filtered as of yellow solid (600 mg).

IR (KBr) 3390, 3090, 2961, 2934, 2838, 1658, 1595, 1570, 1522, 1503, 1474, 1440, 1365, 1265, 1137, 1108, 1089, 1053, 1041, 934, 843 cm$^{-1}$.

$^1$H nmr (300 MHz, DMSO-d$_6$) δ 3.12 (s, 4H), 3.95 (s, 3H), 6.97 (d, 1H, J=9.0 Hz), 7.41 (t, 1H, J=9.0 Hz), 7.46 (t, 1H, J=9.0 Hz), 7.56 (s, 1H), 8.02 (s broad, 2H).

Step 5: Ethyl 2-(7-methoxybenzene[b]thiophen-3-yl)ethylcarbamate 2-(7-methoxybenzene[b]thiophen-3-yl)ethylamine (from step 4) (0.5 g, 1.94 mmol) was dissolved in THF (5 ml) and to the solution added ethylchloroformate (6.29 g, 4.28 mmol) and triethylamine (0.5 ml) and stirred at room temperature for 2.0 hours. Water (50 ml) was added to the reaction mixture and precipitated solid was filtered to get the product as of white solid (0.520 g).

IR (KBr) 3295, 3049, 2979, 2952, 2934, 2938, 1675, 1570, 1531, 1476, 1440, 1365, 1314, 1288, 1183, 1052, 960, 839, 786, 732 cm$^{-1}$.

$^1$H nmr (300 MHz, DMSO-d$_6$) δ 1.1 (t, 3H), 2.92 (t, 2H, J=6.0 Hz), 3.27 (t, 2H, J=6.0 Hz), 3.94 (s, 3H), 3.99 (q, 2H), 6.93 (d, 1H, J=9.0 Hz), 7.26 (s broad, 1H), 7.37 (d, 1H, J=6.0 Hz), 7.42 (t, 1H, J=9.0 Hz).

Step 6: Ethyl 8-methoxy-1,2,3,4-tetrahydrobenzo[4,5]thieno[2,3-c]pyridine-2-carboxylate Ethyl 2-(7-methoxybenzene[b]thiophen-3-yl)ethylcarbamate (from step 5) (0.30 g, 1.31 mmol) was dissolved in toluene (3 ml) and to the solution added para-formaldehyde (0.055 g, 1.84 mmol) and p-toluenesulfonic acid (0.011 g, 0.06 mmol) and stirred at 120° C. temperatures for 10 min. Water (25 ml) was added to the reaction mixture was extracted in ethyl acetate (2×25 ml) The combined ethyl acetate layers were washed with water (2×50 ml), dried over anhydrous sodium sulfate and concentrated under vacuum to give product as of white solid (0.180 g).

IR (KBr) 3070, 2999, 2979, 2796, 1673, 1584, 1555, 1458, 1432, 1337, 1223, 1122, 1044, 1002, 936, 922, 884, 808, 775, 732 cm$^{-1}$.

$^1$H nmr (300 MHz, DMSO-d$_6$) δ 1.1 (t, 3H), 2.80 (t, 2H, J=6.0 Hz), 3.75 (t, 2H, J=6.0 Hz), 3.94 (s, 3H), 4.08 (q, 2H), 4.69 (s, 2H), 6.92 (d, 1H, J=9.0 Hz), 7.15 (d, 1H, J=6.0 Hz), 7.42 (t, 1H, J=9.0 Hz).

Step 7: Ethyl 5-formyl-8-methoxy-1,2,3,4-tetrahydrobenzo[4,5]thieno[2,3-c]pyridine-2-carboxylate Ethyl 8-methoxy-1,2,3,4-tetrahydrobenzo[4,5]thieno[2,3-c]pyridine-2-carboxylate (from step 6) (0.18 g, 0.62 mmol) was dissolved in dichloromethane (5 ml) and cooled to 0° C. To the solution added stannic chloride (0.122 ml, 1.05 mmol) and dichloromethyl methylether (0.07 ml, 0.07 mmol) was added dropwise and stirred under cooling for 2 hours. Water (25 ml) was added to the reaction mixture was extracted in dichloromethane (2×25 ml) The combined organic layers were washed with water (2×50 ml), dried over anhydrous sodium sulfate and concentrated under vacuum to give product as solid (0.170 g).

IR (KBr) 3308, 3070, 2999, 2979, 2934, 2834, 1673, 1690, 1555, 1481, 1458, 1435, 1379, 1350, 1333, 1299, 1268, 1238, 1090, 1029, 921, 807 cm$^{-1}$.

$^1$H nmr (300 MHz, DMSO-d$_6$) δ 1.1 (t, 3H), 3.14 (t, 2H), 3.69 (t, 2H), 4.05 (s, 3H), 4.12 (q, 2H), 4.77 (s, 2H), 7.12 (d, 1H, J=9.0 Hz), 7.99 (d, 1H, J=9.0 Hz), 10.39 (s, 1H).

Step 7: 2-ethoxycarbonyl-8-methoxy-1,2,3,4-tetrahydrobenzo[4,5]thieno[2,3-c]pyridine-5-carboxylic acid The solution of Ethyl 5-formyl-8-methoxy-1,2,3,4-tetrahydrobenzo[4,5]thieno[2,3-c]pyridine-2-carboxylate (from step 6) (0.150 g, 0.470 mmol) in acetone (5 ml) was cooled to 10-20° C. Sulfamic acid (0.056 g, 0.587 mmol) was added at once to the reaction mixture at 10-20° C. Then solution of sodium chlorite (0.052 g, 0.707 mmol) in water (3 ml) was added dropwise at the same temp. Progress of reaction was monitored by TLC. At the end water (15 ml) was added to reaction mixture. Acetone was distilled off under vacuum. The solid obtained was filtered and suck dried. Yellow colored solid (0.110 g) was obtained.

IR (KBr) 3450, 3070, 2934, 2999, 2896, 2739, 1675, 1555, 1534, 1432, 1420, 1392, 1375, 1224, 1212, 1150, 1134, 1094, 996, 885 cm$^{-1}$.

$^1$H nmr (300 MHz, DMSO-d$_6$) δ 1.1 (t, 3H), 2.84 (t, 2H), 3.67 (t, 2H), 4.10 (s, 3H), 4.15 (q, 2H), 4.80 (s, 2H), 7.12 (d, 1H, J=9.0 Hz), 8.01 (d, 1H, J=9.0 Hz).

Step 8: 2-ethyl-5-(4-nitrophenyl)-8-methoxy-1,2,3,4-tetrahydrobenzo[4,5]thieno[2,3-c]pyridine-2,5-dicarboxylate A mixture of 2-ethoxycarbonyl-8-methoxy-1,2,3,4-tetrahydrobenzo[4,5]thieno[2,3-c]pyridine-5-carboxylic acid (from step 7) (150 mg, 0.446 mmol), 4-N,N-dimethyl amino pyridine (5 mg, 0.044 mmol), p-nitro phenol (74 mg, 0.535 mmol) and EDCI (120 mg, 0.535 mmol) in dichloromethane (5 ml) was stirred at room temp for 6-7 hrs. Progress of reaction was monitored by TLC. At the end, reaction mixture was concentrated under vacuum. Then water (25 ml) was added to reaction mixture and acidified with dilute HCl. The precipitate obtained was filtered and dried in oven. And purified in pet ether: acetone (10%) to get pure product 60 mg buff colored solid was obtained IR (KBr) 3435, 3115, 3078, 2984, 2939, 2842, 1735, 1704, 1591, 1566, 1488, 1461, 1347, 1385, 129, 1235, 1162, 1110, 1067, 1029, 907, 816, 786 cm$^{-1}$.

$^1$H nmr (300 MHz, DMSO-d$_6$) δ 1.1 (t, 3H), 2.90 (t, 2H), 3.67 (t, 2H), 4.10 (s, 3H), 4.15 (q, 2H), 4.80 (s, 2H), 7.12 (d, 1H, J=9.0 Hz), 7.67 (d, 2H, J=9.0 Hz), 8.14 (d, 1H, J=9.0 Hz) 8.36 (d, 2H, J=9.0 Hz).

Step 9: 2-ethyl-5-(4-nitrophenyl)-8-methoxy-1,2,3,4-tetrahydrobenzo[4,5]thieno[2,3-c]pyridine-2,5-dicarboxylate A suspension of 2-ethyl-5-(4-nitrophenyl)-8-methoxy-1,2,3,4-tetrahydrobenzo[4,5]thieno[2,3-c]pyridine-2,5-dicarboxylate (from step 8) (100 mg, 0.218 mmol) and 4-amino-3,5-dichloro pyridine (60 mg, 0.371 mmol) in dimethyl formamide (5 ml) was cooled to −10-0° C. under nitrogen. Then sodium hydride (13 mg, 0.328 mmol) was added at once at the same temp. Under nitrogen. Progress of reaction was monitored by TLC. At the end, reaction mixture was cooled to 0-10° C. Water (25 ml) was added drop wise to the reaction mixture at 0-10° C. and acidified with dilute HCl. The precipitate obtained was filtered and dried in oven. The solid was purified by isopropanol leaching to pure product 80 mg. m.p.—decomposes above 270° C.

IR (KBr): 3205, 2982, 1672, 1556, 1497, 1485, 1338, 1287, 1259, 1181, 1122, 1087, 1030, 946, 879 cm$^{-1}$.

$^1$H nmr (300 MHz, DMSO-d$_6$) δ 1.1 (t, 3H), 2.74 (t, 2H), 3.60 (t, 2H), 3.98 (s, 3H), 4.05 (q, 2H), 4.71 (s, 2H), 7.01 (d, 1H, J=9.0 Hz), 7.65 (d, 1H, J=9.0 Hz), 8.73 (s, 2H) 10.80 (s, 1H).

Example 7 tert-butyl 5-(3,5-dichloro-4-pyridylcarbamoyl)-8-methoxy-1,2,3,4-tetrahydrobenzo[4,5]thieno[2,3-c]pyridine-2-carboxylate

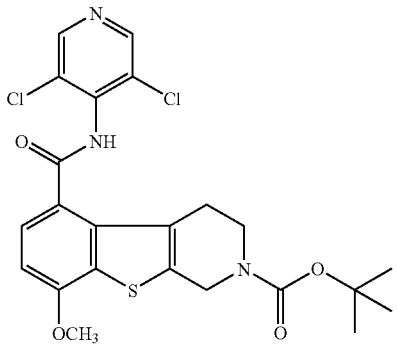

Step 1: 2-tert-butyloxycarbonyl-8-methoxy-1,2,3,4-tetrahydrobenzo[4,5]thieno[2,3-c]pyridine-5-carboxylic acid 2-Ethoxycarbonyl-8-methoxy-1,2,3,4-tetrahydrobenzo[4,5]thieno[2,3-c]pyridine-5-carboxylic acid (from step 7 of example 6) (700 mg) was suspended in ethanolic potassium hydroxide (10 ml) and water (2.5 ml) was added and stirred at 80° C. for 12 hours. Ethanol was evaporated under vacuum and co-evaporated in toluene. Ethyl acetate saturated with hydrochloric acid was added (10 ml) was added to the reaction mixture and precipitated solid was filtered and dried in oven to get pure hydrochloride salt (600 mg). The hydrochloride salt (600 mg), triethylamine (0.5 ml), BOC-anhydride (478 mg) in dichloromethane (5 ml) was stirred at room temp for 12 hrs. Progress of reaction was monitored by TLC. At the end, reaction mixture was concentrated under vacuum. Then water (25 ml) was added to reaction mixture and acidified with dilute HCl. The precipitate obtained was filtered and dried in oven. And purified in chloroform: ethyl acetate (2%) to get pure product 310 mg buff colored solid was obtained.

IR (KBr) 3430, 3011, 2953, 1690, 1550, 1473, 1463, 1392, 1363, 1257, 1243, 1190, 1043, 1011, 999, 875 cm$^{-1}$.

$^1$H nmr (300 MHz, DMSO-d$_6$) δ1.2 (s, 9H), 2.95 (t, 2H), 3.36 (t, 2H), 4.01 (t, 3H), 4.70 (s, 2H), 7.01 (d, 1H, J=9.0 Hz), 8.01 (d, 1H, J=9.0 Hz).

Step 2: 2-(tert-butyl)-5-(4-nitrophenyl)-8-methoxy-1,2,3,4-tetrahydrobenzo[4,5]thieno[2,3-c]pyridine-2,5-dicarboxylate A mixture of SM [WHAT IS SM?] (90 mg, 0.247 mmol), 4-N,N-dimethyl amino pyridine (3 mg, 0.024 mmol), p-nitro phenol (41 mg, 0.297 mmol) and EDCl (57 mg, 0.297 mmol) in dichloromethane (5 ml) was stirred at room temp for 6-7 hrs. Progress of reaction was monitored by TLC. At the end, reaction mixture was concentrated under vacuum. Then water (25 ml) was added to reaction mixture and acidified with dilute HCl. The precipitate obtained was filtered and dried in oven. And purified in chloroform: ethyl acetate (10%) to get pure product 110 mg buff colored solid was obtained IR (KBr) 3015, 2939, 2851, 1652, 1534, 1474, 1421, 1361, 1352, 1281, 1263, 1164, 1142, 1056, 1092, 1005, 848 cm$^{-1}$.

$^1$H nmr (300 MHz, DMSO-d$_6$) δ 1.2 (s, 9H), 2.97 (t, 2H), 3.38 (t, 2H), 4.05 (t, 3H), 4.78 (s, 2H), 7.05 (d, 1H, J=9.0 Hz), 7.55 (d, 2H, J=9.0 Hz), 8.01 (d, 1H, J=9.0 Hz) 8.2 (d, 2H, J=9.0 Hz).

Step 3: tert-butyl 5-(3,5-dichloro-4-pyridylcarbamoyl)-8-methoxy-1,2,3,4-tetrahydrobenzo[4,5]thieno[2,3-c]pyridine-2-carboxylate A suspension of 2-(tert-butyl)-5-(4-nitrophenyl)-8-methoxy-1,2,3,4-tetrahydrobenzo[4,5]thieno[2,3-c]pyridine-2,5-dicarboxylate (from step 2) (110 mg, 0.250 mmol) and 4-amino-3,5-dichloro pyridine (69 mg, 0.427 mmol) in dimethylformamide (5 ml) was cooled to −10-0° C. under nitrogen. Then sodium hydride (15 mg, 0.377 mmol) was added at once at the same temp. Under nitrogen. Progress of reaction was monitored by TLC. At the end, reaction mixture was cooled to 0-10° C. Water (25 ml) was added dropwise to the reaction mixture at 0-10° C. and acidified with dilute HCl. the precipitate obtained was filtered and dried in oven. And purified in chloroform: ethyl acetate (10%) to get pure product 90 mg buff colored solid was obtained IR (KBr): 3435, 3012, 2929, 2853, 1666, 1553, 1480, 1423, 1366, 1280, 1252, 1164, 1092, 1025, 868 cm$^{-1}$.

$^1$H nmr (300 MHz, DMSO-d$_6$) δ 1.2 (s, 9H), 2.89 (t, 2H), 3.60 (t, 2H), 4.02 (t, 3H), 4.70 (s, 2H), 7.05 (d, 1H, J=9.0 Hz), 7.69 (d, 1H, J=9.0 Hz), 8.78 (s, 2H), 10.84 (s, 1H).

Example 8

N5 (3,5-dichloro-4-pyridyl)-8-methoxy-1,2,3,4-tetrahydrobenzo[4,5]thieno[2,3-c]pyridine-5-carboxamide hydrochloride

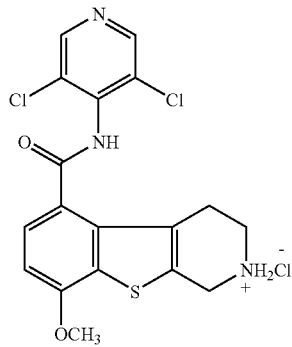

Tert-butyl 5-(3,5-dichloro-4-pyridylcarbamoyl)-8-methoxy-1,2,3,4-tetrahydrobenzo[4,5]thieno[2,3-c]pyridine-2-carboxylate (Example 7) (40 mg, mmol) was suspended in ethyl acetate saturated with hydrochloric acid (5 ml) stirred at room temp for 1 hours. Ethyl acetate was evaporated under vacuum and washed with diethyl ether and dried in oven to get pure salt 20 mg.

IR (KBr) 3020, 2928, 1634, 1554, 1503, 1482, 1441, 1393, 1251, 1215, 1097, 1075, 757 cm$^{-1}$.

$^1$H nmr (300 MHz, DMSO-d$_6$) δ 3.02 (t, 2H), 3.31 (t, 2H), 4.04 (t, 3H), 4.51 (s, 2H), 7.12 (d, 1H, J=9.0 Hz), 7.76 (d, 1H, J=9.0 Hz), 8.79 (s, 2H), 9.45 (s broad, 2H), 10.91 (s, 1H).

Example 9

Ethyl 9-(3,5-dichloro-4-pyridylcarbamoyl)-8-methoxy-1,2,3,4-tetrahydrobenzo[4,5]furo[3,2-c]pyridine-2-carboxylate

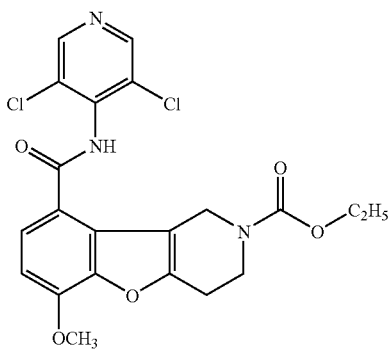

Step 1: Ethyl 7-methoxy-1-benzofuran-2-carboxylate

Isovanillin (10.0 g, 65.72 mmol) was dissolved in DMF (100 ml). To this solution potassium carbonate (22.7 g, 164.3 mmol) was added followed by addition of ethylbromoacetate (16.46 g, 98.58 mmol) and heated at 140° C. for 6 h. Reaction mixture was filtered on celite bed. Filtrate was evaporated on rotavapor and then diluted with water (250 ml) and extracted with ethyl acetate (50 ml×4). Organic layer was washed with water (25 ml×3), brine (25 ml), dried over sodium sulfate and concentrated to yield 11.0 g of the product as yellow solid.

$^1$H NMR (CDCl$_3$): δ 1.42 (t, 3H), 4.02 (s, 3H), 4.45 (q, 2H), 6.91 (d, 1H, J=6.9 Hz), 7.19-7.27 (m, 2H), 7.52 (s, 1H).

IR (KBr): 3128, 2984, 1714, 1578, 1494, 1324, 1297, 1193, 1090, 942, 732 cm$^{-1}$.

Step 2: (7-methoxy-1-benzofuran-2-yl)methanol

Ethyl 7-methoxy-1-benzofuran-2-carboxylate (from step 1) (1.0 g, 4.54 mmol) was dissolved in THF (25 ml). To this solution lithium aluminum hydride (0.344 g, 9.09 mmol) was added at 0° C. portion wise and stirred for 2 h. Reaction was quenched with ice and filtered and the filtrate was dried on sodium sulfate and concentrated on rotavap to yield 600 mg of the product as a pale yellow thick liquid.

$^1$H nmr (CDCl$_3$): δ 3.98 (s, 3H), 4.74 (s, 2H), 6.62 (s, 1H), 6.75-6.79 (m, 1H), 7.11-7.17 (m, 2H).

IR (KBr): 3392, 2941, 2840, 1735, 1606, 1622, 1588, 1493, 1436, 1284, 1095, 972, 932, 731 cm$^{-1}$.

Step 3: 2-(chloromethyl)-7-methoxy-1-benzofuran (7-methoxy-1-benzofuran-2-yl)methanol (from step 2) (1.5 g, 8.42 mmol) was dissolved in dichloromethane (25 ml) To this solution triethylamine (1.7 g, 16.85 mmol) and methane sulfonyl chloride (1.44 g, 16.85 mmol) was added at 0° C. and stirred for 2 h. Reaction mixture was diluted with water (10 ml) and extracted with ethyl acetate (25 ml×3). Organic layer was washed with water (10 ml×2), brine (15 ml), dried over sodium sulfate and concentrated to give 1.5 g of the product as pale yellow thick liquid.

$^1$H nmr (CDCl$_3$): δ 4.01 (s, 3H), 4.71 (s, 2H), 6.47 (s, 1H), 6.81-6.84 (m, 1H), 7.15-7.17 (m, 2H).

IR (KBr): 3113, 2963, 2713, 1621, 1601, 1435, 1359, 1270, 1173, 1060, 975, 819 cm$^{-1}$.

Step 4: (7-methoxy-1-benzofuran-2-yl)acetonitrile 2-(chloromethyl)-7-methoxy-1-benzofuran (from step 3)(1.0 g, 3.92 mmol) was dissolved in DMF (20 ml) and sodium cyanide (190 mg, 3.92 mmol) was added at 0° C. and reaction was stirred for 2 h at room temperature. Reaction was quenched by diluting with water (100 ml) and extracted with ethyl acetate (25 ml×3). Organic layer was washed with water (20 ml×2), brine (15 ml), dried over sodium sulfate and concentrated to yield 1.0 g of product brown thick liquid. Compound was purified by column chromatography using 100-200 mesh silica gel and eluted in 5% ethyl acetate-petroleum ether. Yield=500 mg (yellow solid)

$^1$H nmr (CDCl$_3$): δ 3.93 (s, 2H), 4.01 (s, 3H), 6.77 (s, 1H), 6.82 (d, 1H, J=6.9 Hz), 7.13-7.18 (m, 2H).

IR (KBr): 3020, 2923, 2258, 1622, 1607, 1508, 1494, 1436, 1311, 1272, 1214, 1095, 755 cm$^{-1}$

Step 5: 2-(7-methoxy-1-benzofuran-2-yl)ethanamine (7-methoxy-1-benzofuran-2-yl)acetonitrile (from step 4) (500 mg, 2.67 mmol) was dissolved in methanol (20 ml). To this conc. HCl (0.038 g, 1.068 mmol) and 10% Pd/C (250 mg) was added and kept for hydrogenation at 40 psi for 6 h.

Reaction mixture was filtered through celite and dried over sodium sulfate and concentrated to yield 500 mg of the product as brown thick liquid.

$^1$H-nmr (CDCl$_3$): δ 2.93 (t, 2H), 3.10 (t, 2H), 4.0 (s, 3H), 6.46 (s, 1H), 6.70 (d, 1H, J=6.9 Hz), 7.10-7.15 (m, 2H).

IR (KBr): 3429, 2985, 2450, 1623, 1492, 1438, 1284, 1269, 1202, 1183, 1096, 934, 731 cm$^{-1}$.

Step 6: Ethyl 2-(7-methoxy-1-benzofuran-2-yl)ethylcarbamate 2-(7-methoxy-1-benzofuran-2-yl)ethanamine (from step 5) (100 mg, 0.523 mmol) was dissolved in THF (4 ml). To this solution triethylamine (0.211 g, 2.09 mmol) and ethyl chloroformate (0.085 g, 0.784 mmol) was added at 0° C. and then stirred at room temperature for 5 h. THF was evaporated and the residue was purified by column chromatography using 100-200 mesh silica gel and eluted in 5% ethyl acetate-petroleum ether to obtain 30 mg of yellow thick liquid.

$^1$H nmr (CDCl$_3$): δ 1.22 (t, 3H), 3.01 (t, 2H), 3.57 (t, 2H), 4.0 (s, 3H), 4.12 (q, 2H), 4.79 (brs, 1H), 6.47 (s, 1H), 6.76 (d, 1H, J=6.9 Hz), 7.08-7.15 (m, 2H).

Step 7: 2-ethyoxycarbonyl-6-methoxy-1,2,3,4-tetrahydro[1]benzofuro[3,2-c]pyridine ethyl 2-(7-methoxy-1-benzofuran-2-yl)ethylcarbamate (from step 6) (50 mg, 0.190 mmol) was dissolved in toluene (5 ml). To this para formaldehyde (17 mg, 0.570 mmol) and p-toluene sulfonic acid (2.5 mg) was added and subjected to azeotropic distillation for 2 h. Toluene was evaporated and the residue was purified by column chromatography using 100-200 mesh silica gel and eluted in 10% acetone in petroleum ether. Yield of pure compound was 20 mg (white solid).

$^1$H nmr (CDCl$_3$): δ 1.3 (t, 3H), 2.89 (s, 2H), 3.87 (brs, 2H), 4.01 (s, 3H), 4.20 (q, 2H), 4.60 (brs, 2H), 6.78 (d, 1H, J=8.1 Hz), 7.02 (d, 1H, J=7.8 Hz), 7.15 (t, 1H).

IR (KBr): 3392, 2931, 1698, 1622, 1495, 1435, 1333, 1268, 1226, 1115, 1084, 1014, 775 cm$^{-1}$.

Step 8: 2-ethoxycarbonyl-6-methoxy-1,2,3,4-tetrahydro[1]benzofuro[3,2-c]pyridine-9-carbaldehyde 2-ethyoxycarbonyl-6-methoxy-1,2,3,4-tetrahydro[1]benzofuro[3,2-c]pyridine (from step 7) (0.420 g, 1.52 mmol) was dissolved in dichloromethane (25 ml). To this stannic chloride (0.675 g, 2.59 mmol) was added followed by addition of dichloromethylmethylether (0.17 g, 1.52 mmol) at −10° C. and stirred for 30 min. Reaction was quenched by pouring on crushed ice and extracted with ethyl acetate. Ethyl acetate layer was washed with water (10 ml×2), brine, dried over sodium sulfate and concentrated. The residue was purified by column chromatography using 100-200 mesh silica gel and eluted in 10% ethyl acetate in petroleum ether to get 170 mg of the product as white solid.

$^1$H-nmr (CDCl$_3$): δ 1.3 (t, 3H), 2.92 (brs, 2H), 3.87 (brs, 2H), 4.09 (s, 3H), 4.19 (q, 2H), 4.95 (s, 2H), 6.88 (d, 1H, J=8.4 Hz), 7.68 (d, 1H, J=8.4 Hz), 9.96 (s, 1H).

Step 9: 2-ethoxycarbonyl-6-methoxy-1,2,3,4-tetrahydro[1]benzofuro[3,2-c]pyridine-9-carboxylic acid 2-ethoxycarbonyl-6-methoxy-1,2,3,4-tetrahydro[1]benzofuro[3,2-c]pyridine-9-carbaldehyde (from step 8) (170 mg, 0.559 mmol) was dissolved in acetone (10 ml): water (2.5 ml). To this solution sulfamic acid (81.0 mg, 0.838 mmol) was added and then reaction was cooled to 0° C. Then sodium chlorite (85 mg, 0.950 mmol) in water (2.5 ml) was added drop wise to maintain temperature below 10° C. and reaction was further stirred for 2 h. Reaction was quenched with water (20 ml) and precipitate was filtered on and dried to give 120 mg of white solid as the product.

$^1$H-nmr (CDCl$_3$): δ 1.3 (t, 3H), 2.93 (brs, 2H), 3.86 (brs, 2H), 4.08 (s, 3H), 4.21 (q, 2H), 4.93 (brs, 2H), 6.82 (d, 1H, J=8.4 Hz), 8.03 (d, 1H, J=8.7 Hz).

Step 10: 4-nitrophenyl (2-ethoxycarbonyl-6-methoxy-1,2,3,4-tetrahydro[1]benzo furo[3,2-c]pyridine)-9-carboxylate 2-ethoxycarbonyl-6-methoxy-1,2,3,4-tetrahydro[1]benzofuro[3,2-c]pyridine-9-carboxylicacid (from step 9) (100 mg, 0.338 mmol), p-nitrophenol (94 mg, 677 mmol), EDCl (0.161 mg, 0.845 mmol) and TEA (6.0 mg, 0.067 mmol) was taken in THF (5 ml) and stir at room temperature for 4 h. Reaction was diluted with water (10 ml) and precipitate obtained was filtered and dried to yield 80 mg of product white solid.

$^1$H-nmr (CDCl$_3$): δ 1.25 (brs, 3H), 2.94 (brs, 2H), 3.85 (brs, 2H), 4.11 (s, 3H), 4.19 (q, 2H), 4.89 (brs, 2H), 6.86 (d, 1H, J=8.4 Hz), 7.43 (d, 2H, J=9.0 Hz), 8.13 (d, 1H, J=9.0 Hz), 8.35 (d, 2H, J=8.7 Hz).

Step 11: Ethyl 9-(3,5-dichloro-4-pyridylcarbamoyl)-8-methoxy-1,2,3,4-tetrahydro benzo[4,5]furo[3,2-c]pyridine-2-carboxylate 4-nitrophenyl (2-ethoxycarbonyl-6-methoxy-1,2,3,4-tetrahydro[1]benzofuro[3,2-c]pyridine)-9-carboxylate (from step 10) (80 mg, 0.192 mmol) in DMF (2.5 ml) was added dropwise to the flask containing sodium hydride (27 mg, 0.576 mmol) and 3,5-dichloro-4-aminopyridine (37 mg, 0.230 mmol) in DMF (2.5 ml) at −10° C. and stirred for 1 h. Reaction was quenched with ice, diluted with water (30 ml) and extracted with Ethyl acetate (10 ml×3). Organic layer was washed with water (10 ml), brine (10 ml), dried over sodium sulfate and concentrated to get 50 mg of the product as white solid. Compound was washed with diethyl ether. Yield of pure compound=35 mg (white solid).

$^1$H-nmr (CDCl$_3$): δ 1.25 (t, 3H), 2.92 (brs, 2H), 3.86 (brs, 2H), 4.12 (s, 3H), 4.15 (q, 2H), 4.74 (s, 2H), 6.83 (d, 1H, J=8.4 Hz), 7.61 (s, 2H), 7.66 (d, 1H, J=8.4 Hz), 8.6 (brs, 1H).

IR (KBr): 3019, 2849, 2400, 1683, 1579, 1477, 1402, 1304, 1215, 1120, 928, 767 cm$^{-1}$.

mp: Compound melts >250° C.

Example 10 tert-butyl 9-(3,5-dichloro-4-pyridylcarbamoyl)-6-methoxy-5-methyl-1,3,4,5-tetrahydro-1H-pyrido[4,3-b]indole-2-carboxylate

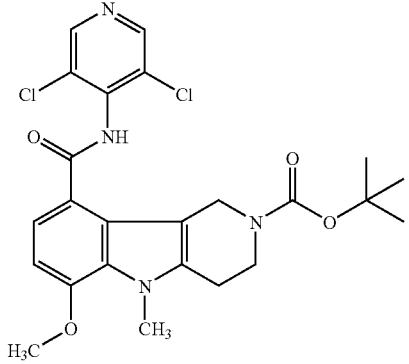

Step 1: Methyl 3-(2-chlorohydrazino)-4-methoxybenzoate

A mixture of Methyl 4-methoxy-3-amino-benzoate (0.044 mol) in 80 ml conc. HCl was stirred for 3 hrs. at room temperature, then solution of sodium nitrite (0.044 mol) in 20 ml water was added over 30 min. at −30° C. (bath temp.) and stirred for 30 min. A solution of stannous chloride (0.088 mol) in 40 ml conc. HCl was added drop wise maintaining a temperature bellow −20° C. and stirring was continued for 1 h. (It forms very thick mass). Reaction was quenched in 400 ml (20% NaOH) with proper cooling and extracted with diethyl ether (200×3 ml). Organic layer washed with water (100 ml) dried over sodium sulphate and concentrate below 40° C. Crude mass was taken in 50 ml diethyl ether and acidified with HCl saturated ethyl acetate to get hydrazine hydrochloride salt (60%) which was dried under vacuum.

$^1$H-nmr (DMSO-d$_6$): δ 10.06 (3H, bs, exchanged with D$_2$O), 7.90 (1H, bs), 7.65 (1H, dd, J=8.4 Hz, J=1.8 Hz), 7.59 (1H, d, J=1.8 Hz), 7.12 (1H, d, J=8.4 Hz), 3.92 (3H, s), 3.8 (3H, s).

Step 2: 2-tert-butyl 9-methyl 6-methoxy-1,3,4,5-tetrahydro-2H-pyrido[4,3-b]indole-2,9-dicarboxylate A mixture of Methyl 3-(2-chlorohydrazino)-4-methoxybenzoate (from step 1) (0.0042 mol) and N-Boc-4-piperidone (0.0063 mol) in ethanol (20 ml) was stirred for 18 h at room temperature. Reaction was concentrated under vacuum and product was isolated with silica gel column chromatography using 20% ethyl acetate in petroleum ether.

$^1$H-nmr (CDCl$_3$): δ 11.4 (1H, bs, exchange with D$_2$O), 7.63 (1H, d, J=8.7 Hz), 6.73 (1H, d, J=8.4 Hz), 4.79 (2H, bs), 3.98 (3H, s), 3.82 (3H, s), 3.64 (2H, t), 2.76 (2H, t), 1.42 (9H, s).

Step 3: 2-tert-butyl 9-methyl-6-methoxy-5-methyl-1,3,4,5-tetrahydro-2H-pyrido[4,3-b]indole-2,9-dicarboxylate To a solution of 2-tert-butyl 9-methyl 6-methoxy-1,3,4,5-tetrahydro-2H-pyrido[4,3-b]indole-2,9-dicarboxylate (from step 2) (0.0027 mol) in N,N-dimethylacetamide (20 ml) at 0° C. was added sodium hydride (0.0081 mol) Stirred for 30 min. at 0° C. then iodomethane (0.0040 mol) was added and stirring was continued for 2 h. Reaction was quenched with water and extracted with ethyl acetate washed with water and then with brine solution dried over sodium sulfate and concentrated. Product was purified by silica gel column chromatography using 10% ethyl acetate: petroleum ether.

$^1$H-nmr (CDCl$_3$): δ 7.72 (1H, d, J=7.5 Hz), 6.58 (1H, d, J=8.4 Hz), 4.79 (2H, bs), 3.98 (3H, s), 3.96 (3H, s), 3.91 (3H, s), 3.83 (2H, t), 2.78 (2H, t), 1.49 (9H, s).

Step 4: 2-tert-butyloxycarbonyl-6-methoxy-5-methyl-1,3,4,5-tetrahydro-2H-pyrido[4,3-b]indole-9-carboxylic acid To a solution of 2-tert-butyl 9-methyl-6-methoxy-5-methyl-1,3,4,5-tetrahydro-2H-pyrido[4,3-b]indole-2,9-dicarboxylate (from step 3) (0.0026 mol) in methanol (20 ml) was added 1N NaOH (0.010 mol) solution and refluxed for overnight. Reaction was then concentrated under vacuum diluted with small amount of water and then washed with ethyl acetate (10×2 ml). Aqueous layer was neutralized with 1N HCl solution up to pH 2. Solid which was precipitated out was filtered washed well with water and dried.

$^1$H-nmr (DMSO-d$_6$): δ 7.86 (1H, d, J=7.5 Hz), 6.61 (1H, d, J=8.4 Hz), 4.92 (2H, bs), 3.98 (3H, s), 3.92 (3H, s), 3.81 (2H, t), 2.80 (2H, t), 1.49 (9H, s).

Step 5: 2-tert-butyl 9-(4-nitrophenyl) 6-methoxy-5-methyl-1,3,4,5-tetrahydro-2H-pyrido[4,3-b]indole-9-dicarboxylate To solution of 2-tert-butyloxycarbonyl-6-methoxy-5-methyl-1,3,4,5-tetrahydro-2H-pyrido[4,3-b]indole-9-carboxylic acid (0.0005 mol) in THF (10 ml) was added Para nitro phenol (0.0011 mol), EDCl (0.0008 mol), DMAP (0.0001 mol) and resulting reaction mixture was stirred at room temperature overnight. Reaction was diluted with small amount of water and precipitated yellow solid was filtered out and dried.

$^1$H-nmr (DMSO-d$_6$): δ 8.36 (2H, d, J=7.0 Hz), 7.4 (1H, d, J=8.4 Hz), 7.60 (2H, d, J=7.0 Hz), 6.84 (1H, d, J=8.4 Hz), 4.72 (2H, bs), 4.00 (3H, s), 3.92 (3H, s), 3.66 (2H, t), 2.80 (2H, t), 1.38 (9H, s).

Step 6: tert-butyl 9-(3,5-dichloro-4-pyridinylcarbamoyl)-6-methoxy-5-methyl-1,3,4,5-tetrahydro-1H-pyrido[4,3-b]indole-2-carboxylate A mixture of 2-tert-butyl 9-(4-nitrophenyl) 6-methoxy-5-methyl-1,3,4,5-tetrahydro-2H-pyrido[4,3-b]indole-9-dicarboxylate (from step 5) (0.0006 mol) and 4-amino-3,5-dichloropyridine (0.0007 mol) in dry DMF (10 ml) was stirred at 0° C. for 20 min. to that solution was added sodium hydride (0.0018 mol) and stirred for 1 h. Reaction was quenched in water to get yellow suspension, 1N HCl was added slowly to get white solid which was filtered washed with water and dried.

$^1$H-nmr (DMSO-d$_6$): δ 10.47 (1H, s, exchanged with D$_2$O), 8.75 (2H, s), 7.48 (1H, d, J=8.1 Hz), 6.77 (1H, d, J=8.1 Hz), 4.47 (2H, bs), 3.96 (3H, s), 3.89 (3H, s), 3.68 (2H, t), 2.77 (2H, t), 1.38 (9H, s).

IR (KBr): 2976, 2932, 1697, 1661, 1556, 1568, 1479, 1246, 1167, 1054, 769 cm$^{-1}$.

Melting Point: 226° C.

Example 11 tert-butyl 9-(3,5-dichloro-4-pyridylcarbamoyl)-6-methoxy-5-benzyl-1,3,4,5-tetrahydro-1H-pyrido[4,3-b]indole-2-carboxylate

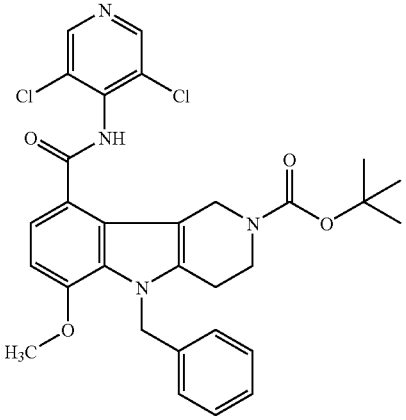

This compound was synthesised by following the process described from step 3 to step 6 for example 10 except for using benzyl bromide instead of iodomethane in step 3.

¹H-nmr (DMSO-d₆): 10.52 (1H, s, exchanged with D₂O), 8.75 (2H, s), 7.52 (1H, d, J=8.1 Hz), 7.25 (3H, m), 6.93 (2H, d, J=7.2 Hz), 6.80 (1H, d, J=8.4 Hz), 5.65 (2H, s), 4.50 (2H, bs), 3.86 (3H, s), 3.64 (2H, t), 2.69 (2H, t), 1.36 (9H, s).

IR (KBr): 3218, 2974, 2938, 1682, 1642, 1562, 1454, 1408, 1254, 1165, 1123, 1106, 1009, 727, 651 cm⁻¹.

Melting Point: 210° C.

Example 12 tert-butyl 9-(3,5-dichloro-4-pyridylcarbamoyl)-6-methoxy-5-cyclopropylmethyl-1,3,4,5-tetrahydro-1H-pyrido[4,3-b]indole-2-carboxylate

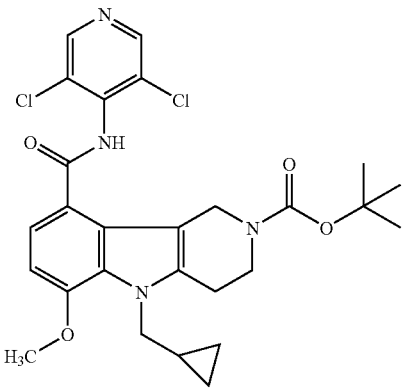

This compound was synthesised by following the process described from step 3 to step 6 for example 10 except for using cyclopropylmethylbromide instead of iodomethane in step 3.

¹H-nmr (DMSO-d₆): δ 10.49 (1H, s, exchanged with D₂O), 8.75 (2H, s), 7.49 (1H, d, J=8.4 Hz), 6.80 (1H, d, J=8.1 Hz), 4.52 (2H, bs), 4.25 (2H, d) 4.03 (3H, s), 3.82 (2H, t), 2.85 (2H, t), 1.25 (9H, s), 1.02 (1H, m), 0.387 (2H, d), 0.307 (2H, d).

IR (KBr): 3271, 2974, 2833, 1690, 1651, 1562, 1488, 1407, 1259, 1239, 1169, 1123, 1021, 773 cm⁻¹.

Melting point: 230° C.

Example 13

N9-(3,5-dichloro-4-pyridylcarbamoyl)-6-methoxy-5-methyl-1,3,4,5-tetrahydro-1H-pyrido[4,3-b]indole hydrochloride

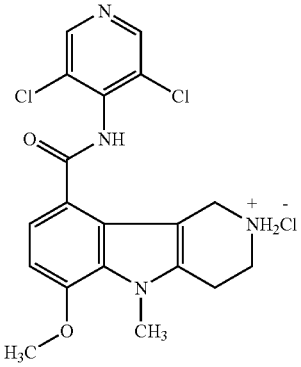

To a chilled 10 ml solution of ethyl acetate saturated with HCl was added tert-butyl 9-(3,5-dichloro-4-pyridinylcarbamoyl)-6-methoxy-5-methyl-1,3,4,5-tetrahydro-1H-pyrido[4,3-b]indole-2-carboxylate (example 10) (0.00025 mol) and stirred at 0° C. for 2 h. Ethyl acetate layer was decanted and diethyl ether was added to that stirred for 30 min. and then ether layer decanted same procedure was followed for 2-3 times to remove HCl and then filtered out and dried.

¹H-nmr (DMSO-d₆): δ 10.5 (1H, s, exchanged with D₂O), 9.12 (2H, bs), 8.73 (2H, s), 7.57 (1H, d, J=8.1 Hz), 6.83 (1H, d, J=8.7 Hz), 4.18 (2H, bs), 3.95 (3H, s), 3.90 (3H, s), 3.96 (2H, t), 3.01 (2H, t).

IR (KBr): 3266, 2956, 1622, 1657, 1568, 1483, 1451, 1406, 1254, 1122, 1075, 703 cm⁻¹

Example 14

N9-(3,5-dichloro-4-pyridylcarbamoyl)-6-methoxy-5-benzyl-1,3,4,5-tetrahydro-1H-pyrido[4,3-b]indole hydrochloride

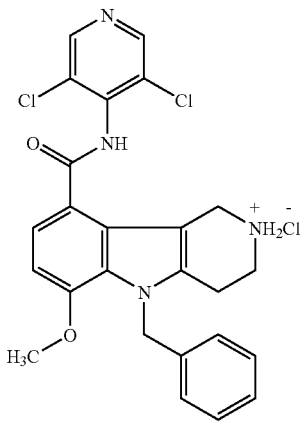

This compound was synthesized form example 11 using the process described for example 13.

¹H-nmr (DMSO-d₆): 10.64 (1H, s, exchanged with D₂O), 9.12 (2H, bs), 8.77 (2H, s), 7.63 (1H, d, J=8.4 Hz), 7.26 (3H, m), 7.01 (2H, d, J=7.2 Hz), 6.86 (1H, d, J=8.1 Hz), 5.66 (2H, s), 4.24 (2H, bs), 3.88 (3H, s), 3.46 (2H, t), 2.99 (2H, t).

IR (KBr): 3231, 2935, 1650, 1607, 1566, 1483, 1451, 1406, 1254, 1122, 1075, 703 cm⁻¹.

Melting point: Decomposes above 250° C.

Example 15

N9-(3,5-dichloro-4-pyridylcarbamoyl)-6-methoxy-2,5-methyl-1,3,4,5-tetrahydro-1H-pyrido[4,3-b]indole

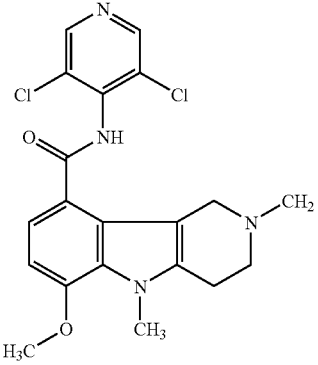

To a solution of N9-(3,5-dichloro-4-pyridylcarbamoyl)-6-methoxy-5-methyl-1,3,4,5-tetrahydro-1H-pyrido[4,3-b]indole hydrochloride (example 13) (0.0096 mmol) in ethanol was added sodium cyanoborohydride (0.241 mmol.) formaldehyde (0.241 mmol.) and Stirred for 15 min. Acetic acid was added to adjust pH to 5 and resulting reaction mass was stirred for 5 h. Reaction mass was concentrated on high vacuum added saturated solution of sodium bicarbonate and then extracted with dichloromethane, dried on sodium sulfate and concentrate. Product was purified by triturating in diethyl ether.

¹H-nmr (DMSO-d₆): δ10.47 (1H, s, exchanged with D₂O), 8.75 (2H, s), 7.48 (1H, d, J=8.1 Hz), 6.77 (1H, d, J=8.1 Hz), 3.96 (3H, s), 3.89 (3H, s), 3.75 (2H, bs), 2.97 (2H, bs), 2.89 (2H, bs), 2.51 (3H, s).

IR (KBr): 3232, 2942, 2169, 1657, 1566, 1471, 1402, 252, 1108, 1045, 801, 774 cm⁻¹.

Melting Point: 248° C.

Example 16

N9-(3,5-dichloro-4-pyridylcarbamoyl)-6-methoxy-2-methyl-5-benzyl-1,3,4,5-tetrahydro-1H-pyrido[4,3-b]indole

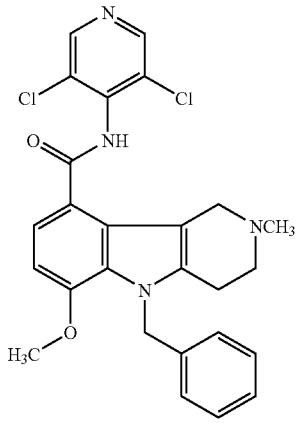

This compound was synthesized form example 14 using the process described for example 15.

¹H-nmr (DMSO-d₆): 10.52 (1H, s, exchanged with D₂O), 8.75 (2H, s), 7.52 (1H, d, J=8.1 Hz), 7.25 (3H, m), 6.93 (2H, d, J=7.2 Hz), 6.80 (1H, d, J=8.4 Hz), 5.65 (2H, s), 4.80 (3H, s), 3.47 (2H, bs), 2.68 (2H, bs), 2.63 (2H, bs), 2.31 (3H, s).

IR (KBr): 2922, 2809, 1670, 1577, 1546, 1510, 1410, 1350, 1296, 1112, 894, 804, 706 cm⁻¹.

Melting Point: Decomposes above 250° C.

Example 17 tert-butyl 9-(4-pyridinylcarbamoyl)-6-methoxy-5-methyl-1,3,4,5-tetrahydro-1H-pyrido[4,3-b]indole-2-carboxylate

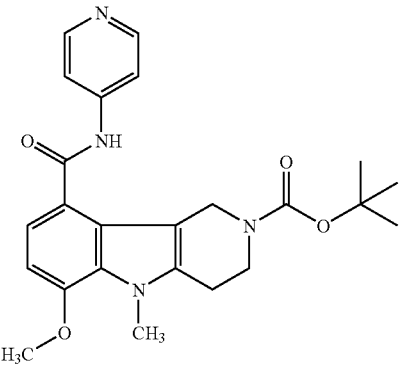

This compound was synthesized from 2-tert-butyl 9-(4-nitrophenyl) 6-methoxy-5-methyl-1,3,4,5-tetrahydro-2H-pyrido[4,3-b]indole-9-dicarboxylate (from step 5 of example 10) using the process described in step 6 of example 10. 4-amino-3,5-dichloropyridine was replaced by 4-aminopyridine.

Example 18

N9-(3,5-dichloro-4-pyridyl)-6-methoxybenzo[4,5]furo[2,3-d]pyridazine-9-carboxamide sodium salt

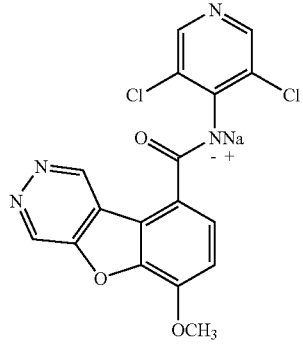

To the suspension of N9-(3,5-dichloro-4-pyridyl)-6-methoxybenzo[4,5]furo[2,3-d]pyridazine-9-carboxamide (example 1) (70 mg) in THF, sodium hydride (15 mg) was added at once at the same temperature under nitrogen. Progress of reaction was monitored by IR. At the end, reaction mixture was concentrated under vacuum.

IR (KBr): 3096, 2968, 2928, 1628, 1583, 1526, 1467, 1450, 1390, 1292, 1202, 1118, 1026, 885, 811 cm⁻¹.

¹H nmr (300 MHz, DMSO-d₆) δ 4.05 (s, 3H), 7.39 (d, 1H, J=8.4 Hz), 8.22 (d, 1H, J=8.4 Hz), 8.23 (s, 2H), 9.83 (s, 1H), 10.88 (s, 1H).

Example 19

N-(3,5-dichloropyridin-4-yl)-2-(ethoxycarbonyl)-8-methoxy-1,2,3,4-tetrahydro[1]benzofuro[2,3-c]pyridine-5-carboxamide

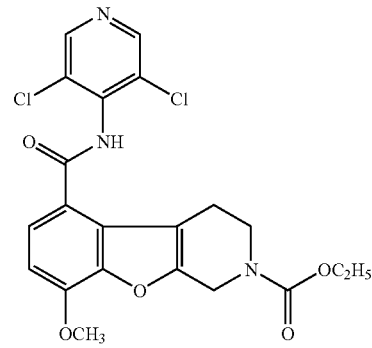

Step 1: (7-methoxy-1-benzofuran-3-yl)acetonitrile

The solution of 7-methoxy-1-benzofuran-3(2H)-one (reference) (7.5 g, 0.046 mol), cyanoacetic acid (19.55 g, 0.23 mol) and ammonium acetate (7.08 g, 0.092 mol) in xylene was refluxed for 16-18 h. using dean stark apparatus. Xylene was removed under diminished pressure. Brown black residue was taken in ethyl acetate, washed with water and concentrated. On purification on silica gel it yielded (7-methoxy-1-benzofuran-3-yl)acetonitrile (30%).

¹H-nmr (CDCl₃): δ 3.72 (s, 2H), 4.023 (s, 3H), 6.887 (d, 1H), 7.271-7.152 (m, 3H), 7.679 (s, 1H).

Step 2: 2-(7-methoxy-1-benzofuran-3-yl)ethanamine hydrochloride

To the suspension of lithium aluminium hydride (580 mg, 0.01 mol) in dry ether, a solution of (7-methoxy-1-benzofuran-3-yl)acetonitrile (from step 1) (750 mg, 0.004 mol) was added drop wise at 0° C. and stirred for half an hour. By adding minimum of water and excess of chloroform, it was stirred overnight. Chloroform layer was dried on any. Sodium sulphate and concentrated. Residue was dissolved in dry ether and hydrochloride salt (92%) was prepared by addition of ethyl acetate saturated with HCl.

¹H-nmr (DMSO-d₆): 2.968 (t, 2H, J=7.35 Hz), 3.087 (t, 2H, J=7.05 Hz), 3.926 (s, 3H), 7.276-7.182 (m, 2H), 8.082 (br, s, 2H, exchanges with D₂O).

Step 3: Ethyl 2-(7-methoxy-1-benzofuran-3-yl)ethylcarbamate

To the suspension of 2-(7-methoxy-1-benzofuran-3-yl) ethanamine hydrochloride (from step 2) (0.432 g, 1.9 mmol) in dry THF, triethylamine (0.769 g, 7.6 mmol) was added followed by ethyl chloroformate (0.265 g, 2.4 mmol) and stirred for 18 hrs. Water was added to it and extracted with ethyl acetate. Organic layer was concentrated and purified on Silica gel column to yield Ethyl 2-(7-methoxy-1-benzofuran-3-yl)ethylcarbamate (82%).

¹H-nmr (CDCl₃): 1.23 (t, 3H, J=6.9 Hz), 2.890 (t, 2H, J=6.9 Hz), 3.510 (q, 2H, J=6.5 Hz), 4.014 (s, 3H), 4.118 (q, 2H, J=7.1 Hz), 4.728 (br s, 1H, exchanges with D₂O), 6.823 (d, 1H, J=5.85 Hz), 7.165-7.238 (m, 2H), 7.476 (s, 1H).

Step 4: Ethyl 8-methoxy-3,4-dihydro[1]benzofuro[2,3-c]pyridine-2(1H)-carboxylate A solution of ethyl 2-(7-methoxy-1-benzofuran-3-yl)ethylcarbamate (from step 4) (0.649 g, 2.5 mmol), paraformaldehyde (0.150 g, 5.0 mmol) and 4-toluene sulphonic acid (0.0475 g, 0.125 mmol) was subjected to Dean-Stark for 2-3 hrs. After cooling to RT, water was added and organic layer was separated dried over anhy. sodium sulphate and concentrated. On purification on silica gel, it yielded ethyl 8-methoxy-3,4-dihydro[1]benzofuro[2,3-c]pyridine-2(1H)-carboxylate (96%).

¹H-nmr (CDCl₃): 1.29 (t, 3H, J=7.2 Hz), 2.73 (br s, 2H), 3.80 (br s, 2H), 4.01 (s, 3H), 4.19 (q, 2H, J=7.2 Hz), 4.65 (br s, 2H), 6.79 (d, 1H, J=7.8 Hz), 7.04 (d, 1H, J=7.5 Hz), 7.162 (t, 1H, J=7.6 Hz).

Step 6: Ethyl 5-formyl-8-methoxy-3,4-dihydro[1]benzofuro[2,3-c]pyridine-2(1H)-carboxylate To a solution of ethyl 8-methoxy-3,4-dihydro[1]benzofuro[2,3-c]pyridine-2(1H)-carboxylate (from step 5) (0.264 g, 0.96 mmol), in methylene chloride, was added stannic chloride (0.424 g, 1.6 mmol) and 1,1-dichloromethyl methyl ether (0.1655 g, 1.4 mmol) at −10° C. Reaction mass was diluted with dichloromethane, water was added to it and organic layer was thoroughly washed with water after separation. It was concentrated and purified to yield Ethyl 5-formyl-8-methoxy-3,4-dihydro[1]benzofuro[2,3-c]pyridine-2(1H)-carboxylate (97%).

¹H-nmr (CDCl₃): 1.34 (m, 3H), 3.15 (t, 2H, J=5.7 Hz), 3.78 (br s, 2H), 4.09 (s, 3H), 4.21 (m, 2H), 4.70 (br s, 2H), 6.89 (d, 1H, J=8.4 Hz), 7.72 (d, 1H, J=8.1), 10.04 (s, 1H).

Step 7: 2-(ethoxycarbonyl)-8-methoxy-1,2,3,4-tetrahydro[1]benzofuro[2,3-c]pyridine-5-carboxylic acid Ethyl 5-formyl-8-methoxy-3,4-dihydro[1]benzofuro[2,3-c]pyridine-2(1H)-carboxylate (from step 6) (0.310 g, 1.02 mmol) was taken in acetone water mixture. To this was added sulphamic acid (0.148 g, 1.53 mmol) and sodium chlorite (0.157 g, 1.73 mmol) and stirred for half an hour. After removing acetone under diminished pressure and dilution with water, it yielded 2-(ethoxycarbonyl)-8-methoxy-1,2,3,4-tetrahydro[1]benzofuro[2,3-c]pyridine-5-carboxylic acid (41%) which was filtered out, washed with water and dried.

¹H-nmr (DMSO-d): 1.22 (t, 3H, J=7.05 Hz), 2.94 (br s, 2H), 3.65 (t, 2H, J=5.4 Hz), 3.984 (s, 3H), 4.31 (q, 2H, J=7.1), 4.62 (br s, 2H), 7.00 (d, 1H, J=8.4 Hz), 7.81 (d, 1H, J=8.4 Hz), 12.7-12.8 (br s, 1H, exchanges with D₂O).

Step 8: 4-nitrophenyl 2-(ethoxycarbonyl)-8-methoxy-1,2,3,4-tetrahydro[1]benzo furo[2,3-c]pyridine-5-carboxylate A solution of 2-(ethoxycarbonyl)-8-methoxy-1,2,3,4-tetrahydro[1]benzofuro[2,3-c]pyridine-5-carboxylic acid (from step 7) (0.352 g, 1.1 mmol), 4-nitrophenol (0.229 g, 1.65 mmol), EDCl (0.253 g, 1.32 mmol) and 4-(N,N-dimethyl) aminopyridine (0.027 g, 0.22 mmol) in tetrahydrofuran was stirred overnight. Water was added to RM, extracted with ethyl acetate and org layer was concentrated after drying on anhy. Sod. Sulphate. The solid was chromatographed on silica gel to yield 4-nitrophenyl 2-(ethoxycarbonyl)-8-methoxy-1,2,3,4-tetrahydro[1]benzofuro[2,3-c]pyridine-5-carboxylate.

¹H-nmr (CDCl₃): 1.288 (t, 3H, J=7.2 Hz), 3.086 (br s, 2H), 3.729 (br s, 2H), 4.114 (s, 3H), 4.194 (q, 2H, J=7.1 Hz), 4.710 (br s, 2H), 6.896 (dd, 2H), 8.154 (dd, 2H).

Step 9: N-(3,5-dichloropyridin-4-yl)-2-(ethoxycarbonyl)-8-methoxy-1,2,3,4-tetra hydro[1]benzofuro[2,3-c]pyridine-5-carboxamide To a solution of 4-amino-3,5-dichloro pyridine (0.125 g, 0.765 mmol) in dry DMF, sodium hydride (0.0162 g, 0.675 mmol) was added at 0° C. followed by 4-nitrophenyl 2-(ethoxycarbonyl)-8-methoxy-1,2,3,4-tetrahydro[1]benzofuro[2,3-c]pyridine-5-carboxylate (0.197 g, 0.45 mmol). Water was added to RM. Solid filtered out and purified on Silica Gel column with CHCl₃: EtOAc to yield N-(3,5-dichloropyridin-4-yl)-2-(ethoxycarbonyl)-8-methoxy-1,2,3,4-tetrahydro[1]benzofuro[2,3-c]pyridine-5-carboxamide.

¹H-nmr (DMSO-d₆): 1.20 (t, 3H, J=6.9 Hz), 2.74 (br s, 2H), 3.64 (t, 2H), 4.01 (s, 3H), 4.095 (q, 2H, J=7.1 Hz), 4.63 (br s, 2H), 7.08 (d, 1H, J=8.1 Hz), 7.73 (d, 1H, J=8.4 Hz), 8.758 (s, 2H), 10.639 (s, 1H).

IR (KBr)(cm⁻¹):—3344, 3019, 2980, 1696, 1665, 1484, 1261, 1223.

Example 20

N-(3,5-dichloropyridin-4-yl)-8-methoxy-1,2,3,4-tetrahydro[1]benzofuro[2,3-c]pyridine-5-carboxamide hydrochloride

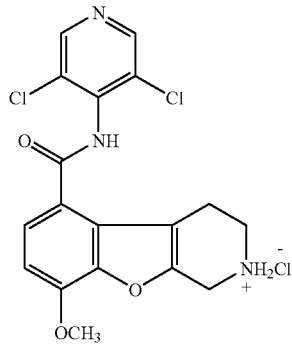

Step 1: 2-(tert-butoxycarbonyl)-8-methoxy-1,2,3,4-tetrahydro[1]benzofuro[2,3-c]pyridine-5-carboxylic acid 2-(ethoxycarbonyl)-8-methoxy-1,2,3,4-tetrahydro[1]benzofuro[2,3-c]pyridine-5-carboxylic acid (1.99 gm, 0.0063 mol) (from Step No. 7 of example 19) was taken in 3 N solution of potassium hydroxide (1.77 gm, 0.0315 mol) and refluxed for 2 Hrs. After extraction with ethyl acetate, Di-tert-butyl dicarbonate (2.75 gm, 0.0126 mol) was added to it and stirred it overnight at room temperature. Reaction mixture was extracted with solvent ether and acidified with potassium per sulphate. The solid 2-(tert-butoxycarbonyl)-8-methoxy-1,2,3,4-tetrahydro[1]benzofuro[2,3-c]pyridine-5-carboxylic acid (69%) was filtered out, washed with water and dried in vacuo.

$^1$H-nmr (DMSO-$d_6$): δ 1.4 (s, 9H), 2.926 (br s, 2H), 3.595 (t, 2H, J=5.4 Hz), 3.985 (s, 3H), 4.576 (s, 2H), 6.998 (d, 1H, J=8.4 Hz), 7.815 (d, 1H, J=8.4 Hz) 12.7 (br s, 1H, exchanges with $D_2O$).

Step 2: 4-nitrophenyl 2-(tert-butyloxycarbonyl)-8-methoxy-1,2,3,4-tetrahydro[1]benzofuro[2,3-c]pyridine-5-carboxylate This compound was synthesized from 2-(tert-butoxycarbonyl)-8-methoxy-1,2,3,4-tetrahydro[1]benzofuro[2,3-c]pyridine-5-carboxylic acid (from step 1) using the process described in step 8 of example 19.

Step 3: N-(3,5-dichloropyridin-4-yl)-2-(tert-butyloxycarbonyl)-8-methoxy-1,2,3,4-tetrahydro[1]benzofuro[2,3-c]pyridine-5-carboxamide This compound was synthesized from 4-nitrophenyl 2-(tert-butyloxycarbonyl)-8-methoxy-1,2,3,4-tetrahydro[1]benzofuro[2,3-c]pyridine-5-carboxylate (from step 2) using the process described in step 9 of example 19.

$^1$H-nmr (DMSO-$d_6$): δ 1.425 (s, 9H), 2.722 (s, 2H), 3.584 (t, 2H, J=4.8 Hz), 4.01 (s, 3H), 4.588 (s, 2H), 7.082 (d, 1H, J=8.4 Hz), 7.734 (d, 1H, J=8.4 Hz), 8.759 (s, 2H), 10.639 (s, 1H, exchanges with $D_2O$).

Step 4: N-(3,5-dichloropyridin-4-yl)-8-methoxy-1,2,3,4-tetrahydro[1]benzofuro[2,3-c]pyridine-5-carboxamide hydrochloride N-(3,5-dichloropyridin-4-yl)-2-(tert-butoxycarbonyl)-8-methoxy-1,2,3,4-tetrahydro[1]benzofuro[2,3-c]pyridine-5-carboxamide (from step 3) (645 mg, 0.0013 mol) was taken in dry ethyl acetate and ethyl acetate saturated with HCl was added to it at 0° C. it was then stirred for an hour. Ethyl acetate was removed under diminished pressure and dry solvent ether was added to it. Solid N-(3,5-dichloropyridin-4-yl)-8-methoxy-1,2,3,4-tetrahydro[1]benzofuro[2,3-c]pyridine-5-carboxamide hydrochloride (XIII) was filtered, washed with dry solvent ether and dried.

$^1$H NMR ($CD_3OD$): δ 3.040 (t, 2H, J=5.4 Hz), 3.443 (t, 2H, J=5.7 Hz), 3.984 (s, 3H), 4.393 (s, 2H), 7.005 (d, 1H, J=8.1 Hz), 7.77 (d, 1H, J=8.1 Hz), 8.569 (s, 2H).

IR (KBr; cm$^{-1}$) 3422, 3233, 2722, 1674, 1493, 1289, 1272, 1009.

Example 21

N-(3,5-dichloropyridin-4-yl)-6-methoxy-1,2,3,4-tetrahydro[1]benzofuro[3,2-c]pyridine-9-arboxamide hydrochloride

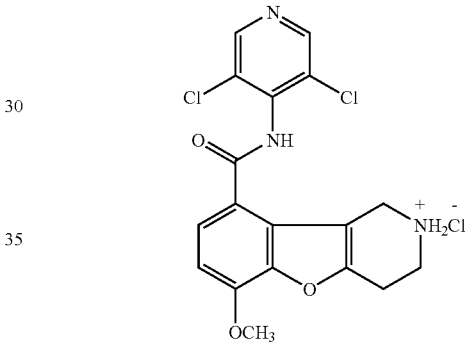

Step 1: 6-methoxy-1,2,3,4-tetrahydro[1]benzofuro[3,2-c]pyridine-9-carboxylic acid 2-ethoxycarbonyl-6-methoxy-1,2,3,4-tetrahydro[1]benzofuro[3,2-c]pyridine-9-carboxylic acid (from step 9 of example 9) (1.8 g, 6.10 mmol) was dissolved in methanol (10 ml). To this KOH (6.8 g, 122.03 mmol) dissolved in 10 ml water was added and reaction mixture was refluxed overnight. Reaction mixture was concentrated and residue was diluted with water (25 ml) and neutralized with (15 ml) saturated ammonium chloride solution. The precipitate obtained was filtered and dried under vacuum. Yield=1.6 g (pale yellow solid).

Step 2: 2-(tert-butoxycarbonyl)-6-methoxy-1,2,3,4-tetrahydro[1]benzofuro[3,2-c]pyridine-9-carboxylic acid 6-methoxy-1,2,3,4-tetrahydro[1]benzofuro[3,2-c]pyridine-9-carboxylic acid (from step 1) (1.6 g, 8.09 mmol) was dissolved in 1M NaOH (25 ml). To this solution di-tert-butyl dicarbonate (2.64 g, 12.14 mmol) was added and reaction was stirred overnight at room temperature. Reaction mixture was extracted with ether and aqueous layer was acidified with potassium hydrogen sulfate. The precipitate obtained was filtered and dried under vacuum. Yield=1.6 g (pale yellow solid)

$^1$H-nmr (DMSO-d$_6$): δ 1.42 (s, 9H), 2.81 (br s, 2H), 3.7 (t, 2H), 3.95 (s, 3H), 4.74 (br, s, 2H), 6.9 (d, 1H, J=8.4 Hz), 7.75 (d, 1H, J=8.4 Hz).

Step 3: 4-nitrophenyl 2-(tert-butyloxycarbonyl)-6-methoxy-1,2,3,4-tetrahydro[1]benzofuro[3,2-c]pyridine-9-carboxylate This compound was synthesized from 2-(tert-butoxycarbonyl)-6-methoxy-1,2,3,4-tetrahydro[1]benzofuro[3,2-c]pyridine-9-carboxylic acid (from step 2) using the process described in step 8 of example 19.

Step 4: N-(3,5-dichloropyridin-4-yl)-2-(tert-butyloxycarbonyl)-6-methoxy-1,2,3,4-tetrahydro[1]benzofuro[3,2-c]pyridine-9-carboxamide This compound was synthesized from 4-nitrophenyl 2-(tert-butyloxycarbonyl)-6-methoxy-1,2,3,4-tetrahydro[1]benzofuro[3,2-c]pyridine-9-carboxylate (from step 3) using the process described in step 9 of example 19.

$^1$H-nmr (DMSO-d$_6$): δ 1.39 (s, 9H), 2.84 (br s, 2H), 3.71 (br s, 2H), 4.01 (s, 3H), 4.52 (br s, 2H), 7.08 (d, 1H, J=8.4 Hz), 7.76 (d, 1H, J=8.1 Hz), 8.77 (s, 2H), 10.67 (s, 1H, exchanges with D$_2$O).

Step 5: N-(3,5-dichloropyridin-4-yl)-6-methoxy-1,2,3,4-tetrahydro[1]benzofuro[3,2-c]pyridine-9-carboxamide hydrochloride To the suspension of N-(3,5-dichloropyridin-4-yl)-2-(tert-butyloxycarbonyl)-6-methoxy-1,2,3,4-tetrahydro[1]benzofuro[3,2-c]pyridine-9-carboxamide (from step 4) (600 mg) in dry diethyl ether (10 ml), ethyl acetate saturated with HCl (4 ml) was added and stirred overnight. Reaction mixture was concentrated and the residue obtained was stirred in dry diethyl ether and filtered. The solid obtained was further purified by refluxing in isopropanol overnight. Yield=400 mg $^1$H-nmr (DMSO-d$_6$) δ: 3.11 (br s, 2H), 3.5 (br s, 2H), 4.03 (s, 3H), 4.29 (br s, 2H), 7.16 (d, 1H, J=8.7 Hz), 7.90 (d, 1H, J=8.4 Hz), 8.78 (s, 2H), 9.29 (br s, 2H, exchanges with D$_2$O), 10.78 (s, 1H, exchanges with D$_2$O).

Example 22

N-(3,5-dichloropyridin-4-yl)-2,9-dimethyl-8-methoxy-1-oxo-1,2,3,4-tetrahydro-β-carboline-5-carboxamide

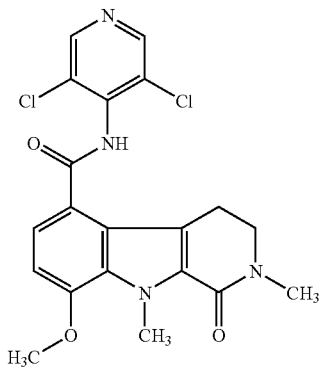

Step 1: Hydrazone Preparation

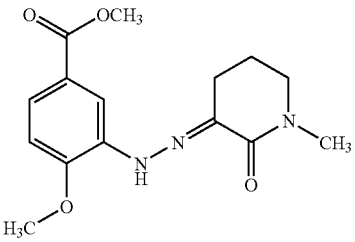

A suspension of 3-carbethoxy-2-piperidone (commercially available) (4.275 g, 25 mmol) in aq. NaOH (1.4 g, 25 mmol, 0.5 N) was stored at room temperature for 18 h. It was then acidified with 6N HCl and added with stirring at 0° C. to a fresh solution of substituted benzenediazonium chloride. (The later was prepared in the usual manner from Methyl 4-methoxy-3-amino-benzoate (4.52 g, 25 mmol) in HCl (125 mmol, 2.7 N) and NaNO$_2$ (1.76 g, 25.5 mmol) in water). The reaction mixture was adjusted to pH 3.5 by the addition of NaOAc (solution in water) followed by stirring at 0-10° C. for 5 h., to afford a precipitate. This was then filtered and used as such for further reaction without purification.

Step 2: Methyl 8-methoxy-1-oxo-1,2,3,4-tetrahydro-β-carboline-5-carboxylate

A solution of hydrazone (from step 1) (11.0 g crude) in acidic ethanol was heated to reflux for 18 h. The solvent was then removed under reduced pressure and the residue was purified by column chromatography to afford pure tetrahydrocarboline in 30 to 40% yield.

$^1$H-nmr (DMSO-d$_6$): 3.15 (2H, t, J=6.6 Hz); 3.43 (2H, m); 3.83 (3H, s); 3.96 (3H, s); 6.84 (1H, d, J=8.4 Hz); 7.70 (1H, d, J=8.1 Hz); 7.70 (1H, b); 11.90 (1H, b).

Step 3: Methyl 8-methoxy-9-methyl-1-oxo-1,2,3,4-tetrahydro-β-carboline-5-carboxylate A suspension of Methyl 8-methoxy-1-oxo-1,2,3,4-tetrahydro-β-carboline-5-carboxylate (from step 2) (1.32 g, 4.81 mmol), iodomethane (0.821 g, 57.8 mmol) and K$_2$CO$_3$ (1.77 g, 12.83 mmol) in DMF was stirred at room temperature for 18 h. minimum amount of water was added and the compound was extracted in ethyl acetate. The organic layer was separated, dried on anhydrous NaSO$_4$ and concentrated under reduced pressure to afford crude product which, on purification by column chromatography afforded the desired N-methyl derivative in 77% yield.

$^1$H-nmr (CDCl$_3$): 3.30 (2H, t, J=6.9 Hz); 3.55 (2H, m); 3.91 (3H, s); 3.98 (3H, s); 4.44 (3H, s); 5.72 (1H, b); 6.67 (1H, d, J=8.1 Hz); 7.74 (1H, d, J=8.4 Hz).

Step 4: Methyl 8-methoxy-2,9-dimethyl-1-oxo-1,2,3,4-tetrahydro-β-carboline-5-carboxylate To a solution of Methyl 8-methoxy-9-methyl-1-oxo-1,2,3,4-tetrahydro-β-carboline-5-carboxylate (from step 3) (0.1 g, 0.347 mmol) and iodomethane (0.069 g, 0.486 mmol) in dry DMF, NaH (0.01 g, 0.416 mmol) was added at once at 0° C. The reaction mixture was stirred for 5 h at room temperature water was added and the compound was extracted in ethyl acetate. Organic layer was separated, dried over anhydrous Na$_2$SO$_4$ and concentrated under reduced pressure to afford the desired dimethyl derivative in quantitative yield.

$^1$H-nmr (CDCl$_3$): 3.14 (3H, s); 3.31 (2H, t, J=6.9 Hz); 3.58 (2H, t, J=6.9 Hz); 3.90 (3H, s); 3.98 (3H, s); 4.45 (3H, s); 6.66 (1H, d, J=8.4 Hz); 7.74 (1H, d, J=8.4 Hz).

Step 5: 8-methoxy-2,9-dimethyl-1-oxo-1,2,3,4-tetrahydro-β-carboline-5-carboxylic acid A suspension of the ester (from step 4) (1 mmol) in alcohol like methanol was treated with aq. KOH (3 mmol) at room temperature for 1 to 3 days. The clear solution obtained was acidified and filtered to afford the desired acid in 70% yield.

$^1$H-nmr (DMSO-d$_6$): 3.00 (3H, s); 3.19 (2H, t, J=6.9 Hz); 3.57 (2H, t, J=6.9 Hz); 3.98 (3H, s); 4.47 (3H, s); 6.82 (1H, d, J=8.4 Hz); 7.66 (1H, d, J=8.4 Hz).

Step 6: p-nitrophenyl 8-methoxy-2,9-dimethyl-1-oxo-1,2,3,4-tetrahydro-β-carboline-5-carboxylate A solution of 8-methoxy-2,9-dimethyl-1-oxo-1,2,3,4-tetrahydro-β-carboline-5-carboxylic acid (from step 5) (1 mmol), p-nitrophenol (1.5 mmol), EDCl (1.5 mmol) and DMAP (0.1 mmol) in dry THF was stirred at r.t. for 18 h. Minimum water was then added and the precipitated p-nitrophenylester was filtered and washed with water and dried (50-60%).

$^1$H-nmr (DMSO-d$_6$): 3.00 (3H, s); 3.17 (2H, t, J=6.9 Hz); 3.55 (2H, t, J=6.9 Hz); 4.03 (3H, s); 4.38 (3H, s); 6.92 (1H, d, J=8.4 Hz); 7.64 (2H, d, J=9.0 Hz); 8.10 (1H, d, J=8.4 Hz); 8.36 (2H, d, J=9.3 Hz).

Step 7: N-(3,5-dichloropyridin-4-yl)-2,9-dimethyl-8-methoxy-1-oxo-1,2,3,4-tetrahydro-β-carboline-5-arboxamide To a solution of p-nitrophenyl ester (from step 6) (1 mmol) and 4-amino-3,5-dichloropyridine (1.2 mmol), NaH (1.2 mmol) was added at once and the reaction mixture was stirred for 18 h at room temperature it was then acidified with few drops of 6N HCl. Desired amide precipitated out that was filtered and dried (80-90%).

$^1$H-nmr (DMSO-d$_6$): 2.96 (2H, t, J=6.9 Hz); 2.99 (3H, s); 3.98 (3H, s); 4.36 (3H, s); 6.92 (1H, d, J=8.4 Hz); 7.53 (1H, d, J=8.1 Hz); 8.75 (2H, s); 10.60 (1H, s).

Melting above 250° C.

IR (Neat) (cm$^{-1}$): 3020, 1642, 1215, 771.

Example 23

N9-(3,5-dichloro-4-pyridyl)-6-difluoromethoxy-benzo[4,5]furo[3,2-c]pyridine-9-carboxamide

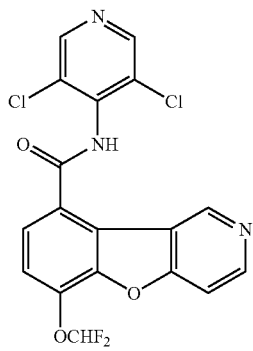

Step 1: 1-methoxy-2-(2-propenyloxy)benzene

To a well stirred solution of guaiacol (100.0 g, 0.805 moles) and propargyl bromide (135 g, 0.966 mmoles) in DMF (600 mL) was added anhydrous K$_2$CO$_3$ (222.0 g, 1.61 moles) and the mixture was stirred at room temperature for 34 hours. The mixture was then filtered to remove inorganic material. Filtrate was concentrated under vacuo and diluted with water (2.5 L). It was then extracted with ethyl acetate (3×1.0 L). The combined organic layers were washed with water (2×1.0 L) and dried over anhydrous sodium sulfate. Removal of solvent under vacuo gave the product (118.0 g) as brown oil.

IR (KBr): 2949, 1728, 1619, 1589, 1426, 1291, 1107, 1001, 957, 825, 758 cm$^{-1}$.

$^1$H nmr (300 MHz, d$_6$-DMSO): 2.49 (s, 1H), 3.86 (s, 3H), 4.76 (s, 2H), 6.95 (m, 4H).

Step 2: 7-methoxy-2-methylbenzo[b]furan

To a well stirred solution of 1-methoxy-2-(2-propenyloxy)benzene (118.0 g, 0.728 moles) in N,N-diethyl aniline (1.0 L) was added cesium fluoride (134 g, 0.874 mmoles) and the mixture was heated to 215-220° C. for 4-5 hours. Reaction mixture was cooled to room temperature and 10% aqueous HCl solution (3.0 lit) was added followed by addition of ethyl acetate (2.0 L). The mixture was the filtered through Celite bed. The organic layer was separated and washed with water (2×1.0 L) and dried over anhydrous sodium sulfate. Removal of solvent under vacuo gave crude product (72.0 g) as dark brown oil. It was then purified through silica gel column using petroleum ether: ethyl acetate (9:1) as an eluent to afford the product as pale yellow oil (4.6 g).

IR (KBr): 2952, 1725, 1627, 1599, 1421, 1285, 1118, 1005, 951, 818, 748 cm$^{-1}$.

$^1$H nmr (300 MHz, d$_6$-DMSO): 2.47 (s, 3H), 4.00 (s, 3H), 6.36 (s, 1H), 7.06 (m, 3H).

Step 3:
7-methoxy-2-methylbenzo[b]furan-4-carboxaldehyde

To a well stirred solution of 7-methoxy-2-methylbenzo[b]furan (72 g, 0.443 moles) in DCM (1.5 L) was added stannous chloride (150.3 g, 0.577 moles) followed by slow addition of 1,1-dichloromethyl methyl ether (56.1 g, 0.488 moles) at −10-0° C. and stirred for 1-2 hrs. Ice cold water (1.0 L) was added with vigorous stirring, the organic layer was separated and washed with water (2×550 mL) and dried over anhydrous sodium sulfate. Removal of solvent gave crude product (68.0 g). The crude product was purified by silica gel column using petroleum ether: ethyl acetate (9:1) as an eluent to afford the product as pale yellow oil (52 g).

m.p. 167-170° C.

IR (KBr): 3017, 1741, 1677, 1595, 1512, 1399, 1242, 1175, 1098, 937, 755 cm$^{-1}$.

$^1$H nmr (300 MHz, d$_6$-DMSO): δ 2.50 (s, 3H), 4.03 (s, 3H), 7.09 (d, 1H, J=8.1 Hz), 7.12 (s, 1H), 7.81 (d, 1H, J=8.4 Hz), 10.00 (s, 1H).

Step 4:
7-Hydroxy-2-methylbenzo[b]furan-4-carbaldehyde

To a freshly prepared solution of sodium-4-methyl benzene thiolate (prepared from 42 g of 4-methyl benzene thiol and 14 g of sodium hydroxide) in toluene (700 mL) was added 7-methoxy-2-methylbenzo[b]furan-4-carboxaldehyde (50.0 g) at reflux. Then HMPA (62.0 g) was added slowly and reaction mixture was stirred at the same temperature for 4-5 hr. reaction mixture was then bring to 50-60° C., water (500 mL) was added and layers were separated. The aqueous layer was acidified (pH 4-5). The solid separated was filtered, washed with water (3×200 mL) and dried to get light yellow solid product (44.0 g).

$^1$H nmr (300 MHz, d$_6$-DMSO) δ 2.50 (s, 3H), 7.11 (d, 1H, J=9.0 Hz), 7.13 (s, 1H), 7.69 (d, 1H, J=9.0 Hz), 9.99 (s, 1H), 10.98 (bs, 1H).

Step 5: 7-cyclopentyloxy-2-methyl benzo[b]furan-4-carboxaldehyde

To a well stirred suspension of 7-Hydroxy-2-methylbenzo[b]furan-4-carbaldehyde (39.0 g, 0.221 moles) in DMF (200 mL) was added powdered potassium carbonate (76.0 g, 0.555 moles) and cyclopentyl bromide (43.0 g, 0.287 moles) and stirred at 70-75° C. for 4-5 hrs. The reaction mixture was then cooled to room temperature and water (1.5 L) was added to it. The organic material separated was extracted with ethyl acetate (3×100 ml). The combined organic layers were washed with water ((2×500 mL) and dried over anhydrous sodium sulfate. Removal of solvent under vacuo gave product (55.0 g) as light brown viscous oil.

IR (KBr): 3432, 1710, 1639, 1501, 1429, 1278, 1122, 1093, 943, 770 cm$^{-1}$.

$^1$H nmr (300 MHz, d$_6$-DMSO) δ 1.6-2.02 (m, 8H), 2.50 (s, 3H), 5.13 (m, 1H), 7.03 (d, 1H, J=9.0 Hz), 7.11 (s, 1H), 7.75 (d, 1H, J=9.0 Hz), 9.99 (s, 1H).

Step 6: 7-cyclopentyloxy-2-methylbenzo[b]furan-4-carboxylic acid

To a well stirred solution of 7-cyclopentyloxy-2-methylbenzo[b]furan-4-carboxaldehyde (55.0 g, 0.225 moles), sulphamic acid (76.0 g, 0.787 moles) in acetone (600 mL) was added a solution of sodium chlorite (51.0 g, 0.562 moles) in water (150 mL) at 0-5° C. and stirred for 5-6 hrs. Ice cold water (1.0 L) was added to reaction mixture; solid separated was filtered and purified by acid-base technique to get 40.0 g of pure product.

IR (KBr): 3300, 1642, 1511, 1423, 1267, 1131, 1009, 958, 770 cm$^{-1}$.

$^1$H nmr (300 MHz, d$_6$-DMSO) δ 1.6-2.1 (m, 8H), 2.47 (s, 3H), 5.07 (m, 1H), 6.89 (d, 1H, J=9.0 Hz), 6.95 (s, 1H), 7.74 (d, 1H, J=8.4 Hz), 12.6 (bs, 1H).

Step 7: Methyl-7-cyclopentyloxy-2-methylbenzo[b]furan-4-carboxylate

To a suspension of 7-cyclopentyloxy-2-methylbenzo[b]furan-4-carboxylic acid (40.0 g, 0.153 moles) and potassium carbonate (42.0 g, 0.184) in acetone (400 mL) added dimethyl sulfate (24.0 g, 0.307 moles) and refluxed for 4-5 hrs. acetone (305 mL) was distilled off and reaction mixture was cooled to 5° C., ice cold water (500 mL) was and the solid separated was filtered, washed with water (2×100 mL) and dried to get off white solid (43.0 g).

IR (KBr): 3434, 1715, 1632, 1409, 1445, 1267, 1102, 1001, 938, 770 cm$^{-1}$.

$^1$H nmr (300 MHz, d$_6$-DMSO) δ 1.6-2.1 (m, 8H), 2.43 (s, 3H), 3.43 (s, 3H), 5.14 (m, 1H), 7.32 (d, 1H, J=9.0 Hz), 8.03 (d, 1H, J=8.4 Hz), 8.24 (s, 1H).

Step 8: Methyl-7-cyclopentyloxy-2-bromomethyl-benzo[b]furan-4-carboxylate

To a well stirred refluxing solution of AIBN (500 mg) and N-bromosuccinimide (30.5 g, 0.171 moles) in carbon tetrachloride (500 mL) was added a Methyl-7-cyclopentyloxy-2-methylbenzo[b]furan-4-carboxylate (43.0 g, 0.151 moles) and refluxed for 2-3 hours. Reaction mixture was cooled to room temperature and filtered thorough Celite bed. The filtrate was concentrated under vacuo to give product (3.1 g) as brown oil. The product obtained (50.0 g) was taken ahead for next step without further purification.

Step 9: Methyl-2-formyl-7-cyclopentyloxybenzo[b]furan-4-carboxylate

To a well stirred solution of Methyl-7-cyclopentyloxy-2-bromomethylbenzo[b]furan-4-carboxylate (50.0 g, 0.140 moles) in dimethyl sulfoxide (250.0 mL) was added powdered sodium carbonate (22.0 g, 0.21 mmoles) at 105-110° C. and stirred for 2-3 hours. Reaction mixture was cooled to room temperature and diluted with water (2.0 L) and extracted with ethyl acetate (3×500 mL). The combined organic layers were washed with water (2×500 mL) and dried over anhydrous sodium sulfate. Removal of solvent gave crude product (51 g) as brown viscous oil. Purification by silica gel column using chloroform: ethyl acetate (95:5) as an eluent afforded 21 g of pure product.

IR (KBr): 3429, 1711, 1688, 1593, 1432, 1307, 1280, 1123, 1020, 973, 831, 737 cm$^{-1}$.

$^1$H nmr (300 MHz, d$_6$-DMSO) δ 1.6-2.1 (m, 8H), 3.92 (s, 3H), 5.14 (m, 1H), 7.32 (d, 1H, J=9.0 Hz), 8.03 (d, 1H, J=8.4 Hz), 8.24 (s, 1H), 9.94 (s, 1H).

Step 10: (Z)-3-(7-cyclopentyloxy-4-methyloxycarbonylbenzo[b]furan-2-yl)-2-propenoic acid To a well stirred solution of Methyl-2-formyl-7-cyclopentyloxybenzo[b]furan-4-carboxylate (21.0 g, 0.0868 moles) in toluene (250.0 mL) was added malonic acid (13.5 g, 0.1302 moles) and Piperidine (5.0 ml). The reaction mixture was then refluxed for 3-4 hours. Reaction mixture was cooled to room temperature, acidified with 10% aqueous HCl solution and extracted with ethyl acetate (2×250 mL). The combined organic layers were washed with water (2×100 mL) and dried over anhydrous sodium sulfate. Removal of solvent under vacuo gave product (19 g) as light yellow solid.

IR (KBr): 3435, 1716, 1630, 1509, 1404, 1335, 1289, 1215, 1145, 1031, 951, 757 cm$^{-1}$.

$^1$H nmr (300 MHz, d$_6$-DMSO): δ 1.6-2.1 (m, 8H), 3.88 (s, 3H), 5.13 (m, 1H), 6.46 (d, 1H, J=15.0 Hz), 7.10 (d, 1H, J=9.0 Hz), 7.60 (d, 1H, J=15 Hz), 7.70 (s, 1H), 7.86 (d, 1H, J=9.0 Hz).

Step 11: Methyl-2-[(Z)-2-azidocarbonyl)-1-ethenyl]-7-methoxybenzo[b]furan-4-carboxylate To a suspension of (Z)-3-(7-cyclopentyloxy-4-methyloxycarbonylbenzo[b]furan-2-yl)-2-propenoic acid (19.0 g, 0.0575 moles) and triethyl amine (1.0 mL) in acetone (200 mL) was added a solution ethyl chloroformate (6.9 g, 0.0633 moles) in acetone (15.0 mL) at −10° C. and stirred for 1-2 hours. A solution of sodium azide (11.0 g, 0.172 moles) in water (30.0 mL) was added at −10° C. and stirred for 1-2 hrs. ice cold water (1.0 L) was added, the solid separated was filtered, dissolved in DCM (200 mL). DCM layer was dried over anhydrous sodium sulfate. Removal of solvent under vacuum gave 21.0 g of product as light yellow solid.

IR (KBr): 3315, 1718, 1638, 1512, 1414, 1333, 1282, 1208, 1134, 1029, 956, 758 cm$^{-1}$.

¹H nmr (300 MHz, d₆-DMSO): δ 1.6-2.1 (m, 8H), 3.88 (s, 3H), 5.14 (m, 1H), 6.51 (d, 1H, J=15.0 Hz), 7.12 (d, 1H, J=9.0 Hz), 7.87 (m, 3H).

Step 12: Methyl-1-hydroxy-6-cyclopentyloxybenzo[4,5]furo[3,2-c]pyridine-9-carboxylate To a well stirred refluxing solution of tri-n-butyl amine (5.0 mL, 25% by wt) in diphenyl ether (50.0 mL) was added a solution of Methyl-2-[(Z)-2-azidocarbonyl)-1-ethenyl]-7-methoxybenzo[b]furan-4-carboxylate (21.0, 0.0642 moles) in diphenyl ether (350.0 mL) and refluxed for 3-3 hours. The excess of diphenyl ether was removed under vacuo and the residue obtained was triturated with petroleum ether (3×100 mL) to give intermediate-12 as yellow solid (16.5 g).

IR (KBr): 3434, 1715, 1661, 1516, 1433, 1287, 1215, 1117, 1014, 755 cm⁻¹.

¹H nmr (300 MHz, d₆-DMSO): δ 1.6-2.1 (m, 8H), 3.87 (s, 3H), 5.16 (m, 1H), 7.22 (d, 1H, J=9.0 Hz), 7.50 (d, 1H, J=9.0 Hz), 7.87 (d, 1H, J=5.4 Hz), 8.42 (d, 1H, J=5.4 Hz), 1.27 (bs, 1H).

Step 13: Methyl-1-chloro-6-hydroxybenzo[4,5]furo[3,2-c]pyridine-9-carboxylate A solution of Methyl-1-hydroxy-6-cyclopentyloxybenzo[4,5]furo[3,2-c]pyridine-9-carboxylate (16.0 g) and phosphorous oxychloride (320 mL) was refluxed for 15-16 hours. Phosphorous oxychloride (300 mL) was removed under vacuo. Water (20.0 ml) was added at 60-70° C. Then after water (200 mL) was added, the solid obtained was filtered, washed with water (2×100 mL) and dried to get 8.8 g of product as yellow solid.

m.p. 195-197° C.

IR (KBr): 1718, 1668, 1507, 1421, 1271, 1223, 1109, 1001, 756 cm⁻¹.

¹H nmr (300 MHz, d₆-DMSO): δ 3.92 (s, 3H), 7.62 (t, 1H, J=72.0 Hz), 7.15 (d, 1H, J=9.0 Hz), 7.50 (d, 1H, J=5.4 Hz), 7.92 (d, 1H, J=5.1 Hz), 11.27 (bs, 1H).

Step 14: Methyl-1-chloro-6-difluoromethyloxybenzo[4,5]furo[3,2-c]pyridine-9-carboxylate To a suspension of Methyl-1-chloro-6-hydroxybenzo[4,5]furo[3,2-c]pyridine-9-carboxylate (8.8 g) and anhydrous potassium carbonate in dimethylformamide was purged mafron gas for 2-3 hrs at 70-80° C. Reaction mixture was filtered through Celite bed; filtrate obtained was concentrated under high vacuum to quarter of its volume. The residue obtained was diluted with water (100 mL) to get 8.0 g product as yellow solid.

m.p. 210-213° C.

IR (KBr): 1718, 1672, 1518, 1431, 1272, 1218, 1113, 1011, 755 cm⁻¹.

¹H nmr (300 MHz, d₆-DMSO): δ 3.86 (s, 3H), 7.62 (t, 1H, J=72.0 Hz), 7.15 (d, 1H, J=9.0 Hz), 7.50 (d, 1H, J=5.4 Hz), 7.92 (d, 1H, J=5.1 Hz).

Step 15: Methyl-6-difluoromethyloxybenzo[4,5]furo[3,2-c]pyridine-9-carboxylate A mixture of Methyl-1-chloro-6-difluoromethyloxybenzo[4,5]furo[3,2-c]pyridine-9-carboxylate (8.0 g), ammonium hydroxide (2.0 mL) and 10% Pd/C (4.0 g) in a mixture of methanol (100 mL) and dimethylformamide (5.0 mL) was hydrogenated in a Parr apparatus at 40-45 psi of hydrogen for 5-6 hrs. catalyst was removed by filtration and residue obtained was diluted with water. The solid product obtained was filtered and dried. Yield=6.5 g.

IR (KBr): 3433, 2075, 1720, 1634, 1288, 1219, 1115, 1017, 771 cm⁻¹.

¹H nmr (300 MHz, d₆-DMSO): δ 4.04 (s, 3H), 7.62 (t, 1H, J=72.0 Hz), 7.61 (d, 1H, J=8.4 Hz), 7.97 (d, 1H, J=5.4 Hz), 8.13 (d, 1H, J=8.4 Hz), 8.78 (d, 1H, J=5.4 Hz), 9.93 (s, 1H).

Step 16: 6-Difluoromethyloxybenzo[4,5]furo[3,2-c]pyridine-9-carboxylic acid

A solution of Methyl-6-difluoromethyloxybenzo[4,5]furo[3,2-c]pyridine-9-carboxylate (6.5 g, 0.0221 moles), sodium hydroxide (4.0 g, 0.110 moles) and water (10.0 mL) in methanol (60.0 mL) was refluxed for 1-1.5 hrs. Methanol was removed under reduced pressure. The residue obtained was diluted with water (50.0 mL) and acidified with acetic acid. The solid separated was filtered, washed with water (2×100 mL) and dried to get 5.5 g of product as off-white solid.

IR (KBr): 3433, 2075, 1559, 1634, 1289, 1215, 1145, 1031, 757 cm⁻¹.

¹H nmr (300 MHz, d₆-DMSO): δ 7.58 (t, 1H, J=72.0 Hz), 7.60 (d, 1H, J=8.4 Hz), 7.94 (d, 1H, J=5.4 Hz), 8.11 (d, 1H, J=8.4 Hz), 8.76 (d, 1H, J=5.4 Hz), 10.02 (s, 1H).

Step 17: 4-Nitrophenyl 6-difluoromethyloxybenzo[4,5]furo[3,2-c]pyridine-9-carboxylate A mixture of 6-Difluoromethyloxybenzo[4,5]furo[3,2-c]pyridine-9-carboxylic acid (5.5 g, 0.0197 moles), p-nitro phenol (4.1 g, 0.0295 moles), EDCl (5.7 g, 0.295 moles), 4,4-dimethyl amino pyridine (250 mg, 0.00197 moles) in DMF (603.0 mL) was heated to 70-75° C. for 4-5 hours. The residue obtained after removal of solvent under vacuo was triturated with water (50.0 mL) to give intermediate-18 (6.0 mg) as yellow solid.

m.p. >250° C.

IR (cm⁻¹): 3430, 2082, 1640, 1534, 1351, 1276, 1223, 1109, 1009, 778 cm⁻¹.

¹H nmr (300 MHz, d₆-DMSO): δ 7.51 (d, 1H, J=8.4 Hz), 7.76 (d, 2H, J=8.4 Hz), 7.80 (t, 1H, J=72.0 Hz) 7.92 (d, 1H, J=5.7 Hz), 8.41 (m, 3H), 8.73 (d, 1H, J=5.4 Hz), 9.87 (s, 1H).

Step 18: N9-(3,5-dichloro-4-pyridyl)-6-difluoromethoxybenzo[4,5]furo[3,2-c]pyridine-9-arboxamide To a well stirred solution of 4-Nitrophenyl 6-difluoromethyloxybenzo[4,5]furo[3,2-c]pyridine-9-carboxylate (6.0 mg, 0.015 moles) and 4-amino-3,5-dichloropyridine (4.9 mg, 0.030 moles) in DMF (50.0 mL) was added sodium hydride (60% dispersion in mineral oil) (900 mg, 0.0225 moles) at −5° C. and stirred for 30-40 minutes. Excess of DMF was removed under reduce pressure, the residue obtained was diluted with water (500 mL) and acidified to pH 5-6 with acetic acid. The solid obtained was filtered, washed with water and dried to afford crude product (5.6 g). Purification thorough silica gel column using 25Methanol in chloroform as eluent gave 2.7 g product as off-white solid.

m.p. >250° C.

IR (Neat): 3199, 1662, 1556, 1496, 1387, 1281, 1198, 1159, 1049, 999, 813, 778 cm⁻¹.

¹H nmr (300 MHz, d₆-DMSO): δ 7.61 (t, 1H), 7.73 (d, 1H, J=8.4 Hz), 7.95 (d, 1H, J=5.4 Hz), 8.08 (d, 1H, J=8.4 Hz), 8.75 (d, 1H, J=5.4 Hz), 8.84 (s, 2H), 9.63 (s, 1H), 11.17 (s, 1H).

Example 24

N9-(3,5-dichloro-4-pyridyl)-6-difluoromethoxybenzo[4,5]furo[3,2-c]pyridine-9-carboxamide sodium

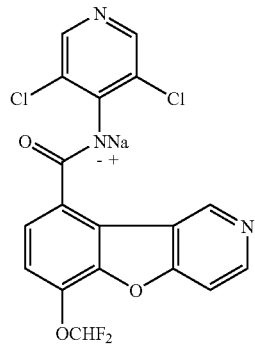

To a well stirred suspension of N9-(3,5-dichloro-4-pyridyl)-6-difluoromethoxybenzo[4,5]furo[3,2-c]pyridine-9-carboxamide (500 mg, 1.178 mmoles) in dry THF (10.0 mL) was a added sodium hydride (60% dispersion in oil) (45 mg, 1.119 mmoles) at 5-10° C. and stirred for 30 minutes. THF was removed under reduced pressure. The solid obtained was washed with n-pentane (2×5 mL) and dried under reduced pressure (520 mg).

m.p. >250° C.

IR (Neat): 3394, 1638, 1572, 1535, 1445, 1389, 1270, 1132, 992, 789 cm⁻¹.

¹H nmr (300 MHz, d₆-DMSO): δ 7.45 (d, 1H, J=9.0 Hz), 7.47 (t, 1H), 7.82 (d, 1H, J=8.4 Hz), 8.13 (d, 1H, J=8.4 Hz), 8.64 (d, 1H, J=5.4 Hz), 10.27 (s, 1H).

Example 25

3,5-dichloro-4-(6-difluoromethoxybenzo[4,5]furo[2,3-d]pyridazine-9-ylcarboxamido)-1-pyridiniumolate

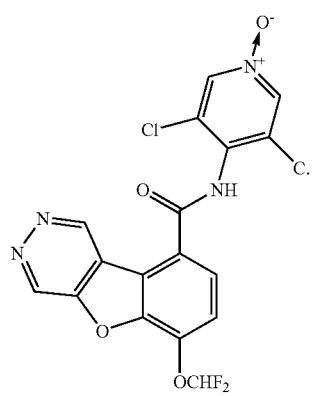

Step 1: 4-amino-3,5-dichloro pyridine-N-oxide

To a solution of 4-amino-3,5-dichloro pyridine (5.0 gm, 0.0306 moles) in chloroform (100 mL) was added 20% peracetic acid solution (200 ml, 0.597 moles) (20% peracetic acid was prepared as per Vogel's Practical Organic Chemistry, Vol. V, page no. 458). Reaction mixture was then stirred at room temperature for 48 hrs, cooled to 5-10° C. and quenched with sodium sulphite till iodide test disappeared. Chloroform as well as acetic acid was removed under reduced pressure. The residue obtained was purified on silica gel column using 5% methanol in chloroform as an eluent to give product as light yellow solid.

Yield: 1.7 g.

Step 2: 3,5-dichloro-4-(6-difluoromethoxybenzo[4,5]furo[2,3-d]pyridazine-9-ylcarboxamido)-1-pyridiniumolate To a well stirred suspension of 4-nitrophenyl 6-difluoromethoxybenzo[4,5]furo[2,3-d]pyridazine-9-carboxylate (100 mg, 0.2481 mmoles), 4-amino-3,5-dichloro pyridine-N-oxide (39 mg, 0.2233 mmoles) in DMF (5.0 mL) was added NaH (60%) (4×5 mg, 0.4962 mmoles) at 5-10° C. The reaction mixture was then allowed to come to room temperature in 2.0 hrs. Reaction mixture was then diluted with water (25 mL) and acidified with acetic acid. The slid separated was extracted with ethyl acetate (3×10 mL). The combined organic layers were washed with water and dried over anhy. sodium sulfate. The residue obtained after removal of solvent was purified on silica gel column using 8% methanol in chloroform as an eluent to give product as off-white solid.

Yield: 40 mg m.p. >250° C.

IR (KBr):—3233, 3065, 1659, 1633, 1602, 1484, 1428, 1343, 1241, 1194, 982, 855, 810 cm⁻¹.

¹H nmr (300 MHz, DMSO-d₆):—δ 7.41 (t, 1H, J=72 Hz), 7.65 (d, 1H, J=8.4 Hz), 7.90 (d, 1H, J=8.4), 8.23 (d, 1H, J=8.7 Hz), 8.82 (s, 2H), 10.08 (s, 1H), 10.17 (s, 1H), 11.09 (s, 1H).

Example 26

3,5-dichloro-4-(6-difluoromethoxybenzo[4,5]furo[3,2-c]pyridin-9-ylcarboxamido)-1-pyridiniumolate

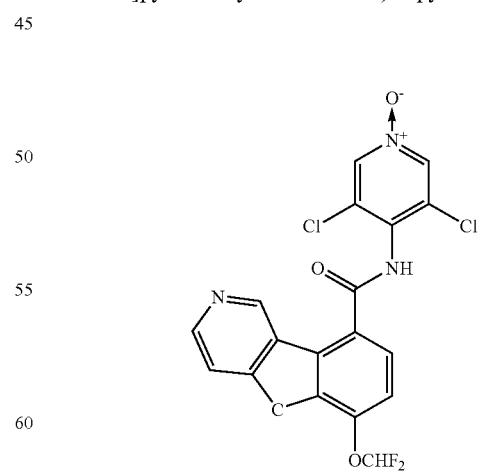

To a well stirred suspension of 4-nitrophenyl 6-difluoromethoxybenzo[4,5]furo[2,3-d]pyridine-9-carboxylate (330 mg, 0.8243 mmoles), 4-amino-3,5-dichloro pyridine-N-oxide (140 mg, 0.7831 mmoles, from step-1, Example 25) in DMF (5.0 mL) was added NaH (60%) (6×11 mg, 1.65 mmoles) at 5-10° C. The reaction mixture was then allowed to come to room temperature in 2.0 hrs. Reaction mixture was then diluted with water (25 mL) and acidified with acetic acid. The slid separated was extracted with ethyl acetate (4×15 mL). The combined organic layers were washed with water and dried over anhy. sodium sulfate. The residue obtained after removal of solvent was purified on silica gel column using 8% methanol in chloroform as an eluent to give product as off-white solid. Yield: 180 mg m.p. >250° C.

IR (KBr):—3436, 3233, 3034, 2923, 2358, 1660, 1599, 1555, 1495, 1289, 1129, 1082, 982, 855, 810 cm$^{-1}$.

$^1$H nmr (300 MHz, DMSO-d$_6$):—δ 7.60 (t, 1H, J=72 Hz), 7.72 (d, 1H, J=8.4 Hz), 7.96 (d, 1H, J=8.4), 8.06 (d, 1H, J=8.7 Hz), 8.76 (d, 1H, J=5.7 Hz), 8.80 (s, 2H), 9.63 (s, 1H), 10.97 (s, 1H).

Example 27

3,5-dichloro-4-(6-difluoromethoxybenzo[4,5]furo[3,2-c]pyridin-9-ylcarboxamido)-1-pyridiniumolate sodium

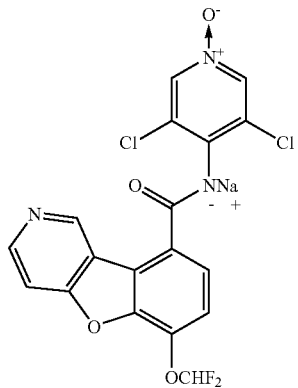

To a well stirred suspension of 3,5-dichloro-4-(6-difluoromethoxy benzo[4,5]furo[3,2-c]pyridin-9-ylcarboxamido)-1-pyridiniumolate (150 mg, 0.3409 mmoles) in THF (5.0 mL) was added 60% sodium hydride (14.5 mg, 0.3579 mmoles) at 5-10° C. under nitrogen atmosphere. The reaction mixture was then stirred for 2.0 hours at room temperature to get clear solution. The yellow solid obtained after solvent removal was triturated with diethyl ether, ether was removed by decantation. The yellow solid obtained was dried under vacuum.

Yield: 150 mg.

m.p.: >250° C.

IR (KBr):—3101, 2928, 1633, 1581, 15511533, 1446, 1388, 1284, 1203, 1117, 1092, 1043, 994, 855, 810 cm$^{-1}$.

$^1$H nmr (300 MHz, DMSO-d$_6$):—δ 7.42 (d, 1H, J=8.4 Hz), 7.46 (t, 1H, J=72 Hz), 7.82 (d, 1H, J=8.4), 8.14 (d, 1H, J=8.7 Hz), 8.25 (s, 2H), 8.64 (d, 1H, J=5.7 Hz), 10.30 (s, 1H).

Example 28

N9-(3,5-dichloro-4-pyridyl)-6-difluoromethoxy-3-ethyl-4-oxo-3,4-dihydro benzo[4,5]furo[2,3-d]pyridazine-9-carboxamide

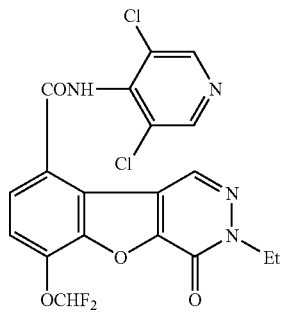

Step I: ethyl 6-difluoromethoxy-3-ethyl-4-oxo-3,4-dihydrobenzo[4,5]furo[2,3-d]pyridazine-9-carboxylate To a solution of ethyl 6-difluoromethoxy-4-oxo-3,4-dihydrobenzo[4,5]furo[2,3-d]pyridazine-9-carboxylate (from step 6 of example 4) (261 mg, 0.803 mmol) in n,n-dimethyl formamide, sodium hydride (33 mg, 0.803 mmol) was added at 20-30° C. under nitrogen. Ethyl bromide (95.4 mg, 0.88 mmol) was added to the reaction mixture. Progress of reaction was monitored by TLC. At the end, reaction mixture was cooled to 0-10° C. Water (100 ml) was added dropwise to the reaction mixture at 0-10° C. and acidified with dilute hydrochloric acid. The precipitate obtained was filtered and dried in oven. It was purified by silica gel column chromatography using 10% ethyl acetate in chloroform. White colored solid (130 mg) was obtained.

m.p.—162-164° C.

IR (KBr): 3081, 2962, 2852, 1741, 1615, 1562, 1454, 1386, 1283, 1162, 1140, 1090, 960, 885, 846, 764 cm$^{-1}$.

$^1$H nmr (300 MHz, DMSO-d$_6$): δ 1.38 (m, 6H), 4.30 (q, 2H), 4.47 (q, 2H), 7.63 (t, 1H, J=72.3 Hz), 7.68 (d, 1H, J=8.4 Hz), 8.18 (d, 1H, J=8.4 Hz), 9.07 (s, 1H).

Step II: 6-difluoromethoxy-3-ethyl-4-oxo-3,4-dihydrobenzo[4,5]furo[2,3-d]pyridazine-9-carboxylic acid A mixture of ethyl 6-difluoromethoxy-3-ethyl-4-oxo-3,4-dihydrobenzo[4,5]furo[2,3-d]pyridazine-9-carboxylate (from step 1) (120 mg, 0.34 mmol) and sodium hydroxide (20 mg, 0.51 mmol) in methanol (20 ml) was heated to reflux temp. Progress of reaction was monitored by TLC. At the end, reaction mixture was concentrated under vacuum. Then water (50 ml) was added to reaction mixture and acidified with dilute HCl. The precipitate obtained was filtered and dried in oven. 98 mg white colored solid was obtained.

m.p.—above 235-237° C.

IR (KBr):—2982, 2360, 1721, 1652, 1592, 1559, 1388, 1267, 1237, 1195, 1118, 1065, 964, 741, 705 cm$^{-1}$.

$^1$H nmr (300 MHz, DMSO-d$_6$):—δ 1.35 (t, 3H), 4.30 (q, 2H), 7.63 (t, 1H, J=72.3 Hz), 7.68 (d, 1H, J=9.0 Hz), 8.18 (d, 1H, J=8.7 Hz), 9.18 (s, 1H).

Step III: 4-nitrophenyl 6-difluoromethoxy-3-ethyl-4-oxo-3,4-dihydrobenzo[4,5]furo[2,3-d]pyridazine-9-carboxylate A mixture of 6-difluoromethoxy-3-ethyl-4-oxo-3,4-dihydrobenzo[4,5]furo[2,3-d]pyridazine-9-carboxylic acid (form step II) (90 mg, 0.276 mmol), triethyl amine (41 mg, 0.415 mmol), p-nitro phenol (43 mg, 0.304 mmol) and EDCl (79 mg, 0.415 mmol) in tetrahydrofuran (3 ml) was stirred at room temp for 16-17 hrs. Progress of reaction was monitored by TLC. At the end, reaction mixture was concentrated under vacuum. Then water (50 ml) was added to reaction mixture and acidified with dilute HCl. The precipitate obtained was filtered and dried in oven. 87 mg buff colored solid was obtained.

m.p. 140-142° C.

IR (KBr):—3115, 3081, 2962, 1741, 1668, 1589, 1518, 1499, 1346, 1333, 1266, 1205, 1108, 1051, 960, 858, 804, 745 cm$^{-1}$.

$^1$H nmr (300 MHz, DMSO-d$_6$):—δ 1.32 (t, 3H), 4.30 (q, 2H), 7.78 (m, 4H), 8.42 (d, 2H, J=9.0 Hz), 8.49 (d, 1H, J=8.4 Hz), 9.00 (s, 1H).

Step IV: N9-(3,5-dichloro-4-pyridyl)-6-difluoromethoxy-3-ethyl-4-oxo-3,4-dihydro benzo[4,5]furo[2,3-d]pyridazine-9-carboxamide A suspension of 4-nitrophenyl 6-difluoromethoxy-3-ethyl-4-oxo-3,4-dihydrobenzo[4,5]furo[2,3-d]pyridazine-9-carboxylate (from step iii) (81 mg, 0.18 mmol) and 4-amino-3,5-dichloro pyridine (32 mg, 0.19 mmol) in dimethyl formamide (3 ml) was cooled to −30-40° C. under nitrogen. Then sodium hydride (15 mg, 0.36 mmol) was added lotwise at the same temp. under nitrogen. Progress of reaction was monitored by TLC. At the end, reaction mixture was cooled to 0-10° C. Water (100 ml) was added dropwise to the reaction mixture at 0-10° C. and acidified with dilute HCl. The precipitate obtained was filtered and dried in oven. The solid was purified by column chromatography using 20% acetone in chloroform. 178 mg pure product was obtained as off white solid.

m.p.—above 270° C.

IR (KBr):—3117, 2930, 1678, 1600, 1494, 1407, 1262, 1125, 1080, 823 cm$^{-1}$.

$^1$H nmr (300 MHz, DMSO-d$_6$):—δ 1.37 (t, 3H), 4.28 (q, 2H), 7.63 (t, 1H, J=72.6 Hz), 7.78 (d, 1H, J=8.4 Hz), 8.17 (d, 1H, J=8.4 Hz), 8.83 (s, 3H), 11.20 (s, 1H).

Example 29

N9-(3,5-dichloro-4-pyridyl)-3-(4-chlorophenyl)-6-difluoromethoxy-4-oxo-3,4-dihydrobenzo[4,5]furo[2,3-d]pyridazine-9-carboxamide

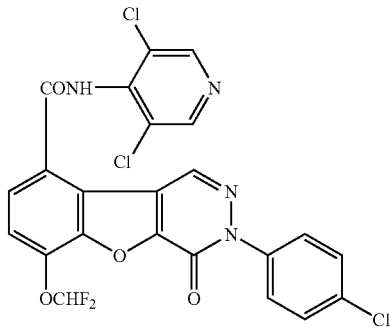

Step I: ethyl 3-(4-chlorophenyl)-6-difluoromethoxy-4-oxo-3,4-dihydrobenzo[4,5]furo[2,3-d]pyridazine-9-carboxylate To a solution of ethyl 6-difluoromethoxy-4-oxo-3,4-dihydrobenzo[4,5]furo[2,3-d]pyridazine-9-carboxylate (from step 6 of example 4) (168 mg, 0.4 mmol) in ethanol (20 ml), p-chloro phenylhydrazine hydrochloride (72 mg, 0.4 mol) and sodium carbonate (43 mg, 0.4 mmol) was added at room temp. The reaction mixture was stirred at room temp. for 4 hrs. Ethanol was distilled out under vacuum. The concentrated mass was heated to reflux temperature in acetic acid. Progress of reaction was monitored by TLC. At the end, water was added, the solid obtained was filtered and suck dried. The solid was dried in oven. White colored solid (160 mg) was obtained.

m.p. 182-184° C.

IR (KBr): 3064, 2989, 1718, 1688, 1592, 1282, 1149, 1093, 1046, 823 cm$^{-1}$.

$^1$H nmr (300 MHz, DMSO-d$_6$):—δ 1.42 (t, 3H), 4.50 (q, 2H), 7.72 (m, 6H), 8.23 (d, 1H, J=8.4 Hz), 9.23 (s, 1H).

Step II: 3-(4-chlorophenyl)-6-difluoromethoxy-4-oxo-3,4-dihydrobenzo[4,5]furo[2,3-d]pyridazine-9-carboxylic acid A mixture of ethyl 3-(4-chlorophenyl)-6-difluoromethoxy-4-oxo-3,4-dihydrobenzo[4,5]furo[2,3-d]pyridazine-9-carboxylate (from step 1) (160 mg, 0.36 mmol) and sodium hydroxide (24 mg, 0.51 mmol) in methanol (10 ml) was heated to reflux temp. Progress of reaction was monitored by TLC. At the end, reaction mixture was concentrated under vacuum. Then water (50 ml) was added to reaction mixture and acidified with dilute HCl. The precipitate obtained was filtered and dried in oven. 140 mg yellow colored solid was obtained.

m.p.—above 250° C.

IR (KBr): 3095, 2641, 1686, 1591, 1492, 1283, 1149, 1094, 969, 825 cm$^{-1}$.

$^1$H nmr (300 MHz, DMSO-d$_6$):—δ 7.72 (m, 6H), 8.21 (d, 1H, J=8.4 Hz), 9.23 (s, 1H).

Step III: 4-nitrophenyl 3-(4-chlorophenyl)-6-difluoromethoxy-4-oxo-3,4-dihydro benzo[4,5]furo[2,3-d]pyridazine-9-carboxylate A mixture of 3-(4-chlorophenyl)-6-difluoromethoxy-4-oxo-3,4-dihydrobenzo[4,5]furo[2,3-d]pyridazine-9-carboxylic acid (from step II) (140 mg, 0.34 mmol), triethyl amine (38 mg, 0.3774 mmol), p-nitro phenol (52 mg, 0.3774 mmol) and EDCl (97 mg, 0.51 mmol) in tetrahydrofuran (3 ml) was stirred at room temp for 16-17 hrs. Progress of reaction was monitored by TLC. At the end, reaction mixture was concentrated under vacuum. Then water (50 ml) was added to reaction mixture and acidified with dilute HCl. The precipitate obtained was filtered and dried in oven. 130 mg buff colored solid was obtained.

m.p.—149-151° C.

IR (KBr): 3115, 2963, 1740, 1687, 1592, 1527, 1490, 1347, 1273, 1212, 1086, 961, 924, 826 cm$^{-1}$.

$^1$H nmr (300 MHz, DMSO-d$_6$):—δ 7.75 (t, 1H, J=72 Hz), 7.81 (d, 1H, J=6.9 Hz), 7.89 (d, 1H, J=8.7 Hz), 8.44 (d, 1H, J=6.9 Hz), 8.54 (d, 1H, J=8.7 Hz), 10.14 (s, 1H), 10.31 (s, 1H).

Step IV: N9-(3,5-dichloro-4-pyridyl)-3-(4-chlorophenyl)-6-difluoromethoxy-4-oxo-3,4-dihydrobenzo[4,5]furo[2,3-d]pyridazine-9-carboxamide A suspension of 4-nitrophenyl 3-(4-chlorophenyl)-6-difluoromethoxy-4-oxo-3,4-dihydro benzo[4,5]furo[2,3-d]pyridazine-9-carboxylate (from step 111) (130 mg, 0.245 mmol) and 4-amino-3,5-dichloro pyridine (44 mg, 0.27 mmol) in dimethylformamide (3 ml) was cooled to −30-40° C. under nitrogen Then sodium hydride (10 mg, 0.49 mmol) was added lot wise at the same temp. under nitrogen, Progress of reaction was monitored by TLC. At the end, reaction mixture was cooled to 0-10° C. Water (100 ml) was added drop wise to the reaction mixture at 0-10° C. and acidified with dilute HCl. the precipitate obtained was filtered and dried in oven. The solid was purified by column chromatography using 20% acetone in chloroform. 23 mg pure product was obtained as off white solid.

m.p.—above 270° C.
IR (KBr): 3204, 3111, 3032, 2972, 1699, 1657, 1599, 1554, 1491, 1282, 1213, 1084, 1057, 921, 835 cm$^{-1}$.
$^1$H nmr (300 MHz, DMSO-d$_6$):—δ 7.65 (m, 5H), 7.83 (d, 1H, J=8.1 Hz), 8.22 (d, 1H, J=8.4 Hz), 8.83 (s, 2H), 8.96 (s, 1H), 11.25 (s, 1H).

Example 30

N9-(3,5-dichloro-4-pyridyl)-6-difluoromethoxy-3-butyl-4-oxo-3,4-dihydrobenzo[4,5]furo[2,3-d]pyridazine-9-carboxylate

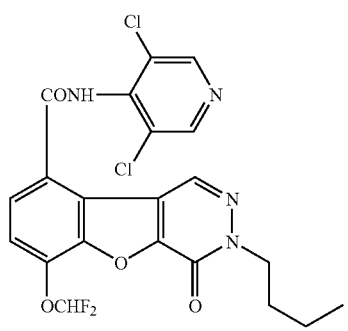

Step I—ethyl 6-difluoromethoxy-3-butyl-4-oxo-3,4-dihydrobenzo[4,5]furo[2,3-d]pyridazine-9-carboxylate This compound was synthesized by the same procedure as described in step 1 of example 28 except ethyl bromide was replaced by n-butyl bromide.
$^1$H nmr (300 MHz, DMSO-d$_6$):—δ 0.92 (t, 3H), 1.38 (m, 5H), 1.77 (p, 2H), 4.27 (t, 2H), 4.48 (q, 2H), 7.64 (t, 1H, J=72.3 Hz), 7.68 (d, 1H, J=8.4 Hz), 8.18 (d, 1H, J=8.7 Hz), 9.10 (s, 1H).

Step II-6-difluoromethoxy-3-butyl-4-oxo-3,4-dihydrobenzo[4,5]furo[2,3-d]pyridazine-9-carboxylic acid This compound was synthesized by the same procedure as described in step II of example 28.

$^1$H nmr (300 MHz, DMSO-d$_6$):—δ 0.92 (t, 3H), 1.33 (m, 2H), 1.77 (p, 2H), 4.27 (t, 2H), 7.62 (t, 1H, J=72.3 Hz), 7.68 (d, 1H, J=8.4 Hz), 8.18 (d, 1H, J=8.7 Hz), 9.16 (s, 1H).

Step III—4-nitrophenyl 6-difluoromethoxy-3-butyl-4-oxo-3,4-dihydrobenzo[4,5]-furo[2,3-d]pyridazine-9-carboxylate This compound was synthesized by the same procedure as described in step III of example 28.
$^1$H nmr (300 MHz, DMSO-d$_6$):—δ 0.90 (t, 3H), 1.33 (m, 2H), 1.75 (p, 2H), 4.26 (t, 2H), 7.77 (m, 4H), 8.42 (d, 2H, J=9.0 Hz), 8.47 (d, 1H, J=8.4 Hz), 8.98 (s, 1H).

Step IV—N9-(3,5-dichloro-4-pyridyl)-6-difluoromethoxy-3-butyl-4-oxo-3,4-dihydrobenzo[4,5]furo[2,3-d]pyridazine-9-carboxylate This compound was synthesized by the same procedure as described in step IV of example 28.
m.p.—210-212° C.
IR (KBr):—3434, 2929, 1694, 1660, 1494, 1282, 1209, 1124, 1094, 1060, 637, 615 cm$^{-1}$.
$^1$H nmr (300 MHz, DMSO-d$_6$):—δ 0.90 (t, 3H), 1.33 (m, 2H), 1.75 (p, 2H), 4.25 (t, 2H), 7.63 (t, 1H, J=72.3 Hz), 7.77 (d, 1H, J=8.1 Hz), 8.18 (d, 1H, J=8.4 Hz), 8.83 (s, 3H), 11.21 (s, 1H).

Example 31

N9-(3,5-dichloro-4-pyridyl)-6-difluoromethoxy-3-cyclopentyl-4-oxo-3,4-dihydrobenzo[4,5]furo[2,3-d]pyridazine-9-carboxylate

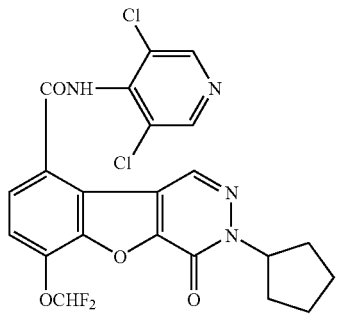

Step I—ethyl 6-difluoromethoxy-3-cyclopentyl-4-oxo-3,4-dihydrobenzo[4,5]furo[2,3-d]pyridazine-9-carboxylate This compound was synthesized by the same procedure as described in step 1 of example 28 except ethyl bromide was replaced by cyclopentyl bromide.
$^1$H nmr (300 MHz, DMSO-d$_6$):—δ 1.40 (t, 3H), 1.68 (bm, 2H), 1.86 (bm, 4H), 2.05 (bm, 2H), 4.47 (q, 2H), 5.49 (bm, 1H), 7.63 (t, 1H, J=72.3 Hz), 7.68 (d, 1H, J=8.1 Hz), 8.18 (d, 1H, J=8.4 Hz), 9.12 (s, 1H).

Step II—6-difluoromethoxy-3-cyclopentyl-4-oxo-3,4-dihydrobenzo[4,5]furo[2,3-d]pyridazine-9-carboxylic acid This compound was synthesized by the same procedure as described in step II of example 28.

$^1$H nmr (300 MHz, DMSO-d$_6$):—δ 1.68 (bm, 2H), 1.91 (bm, 4H), 2.15 (bm, 2H), 5.15 (bm, 1H), 7.65 (m, 2H), 8.18 (d, 1H, J=8.7 Hz), 9.59 (s, 1H).

Step III—4-nitrophenyl-difluoromethoxy-3-cyclopentyl-4-oxo-3,4-dihydrobenzo[4,5]furo[2,3-d]pyridazine-9-carboxylate This compound was synthesized by the same procedure as described in step III of example 28.
$^1$H nmr (300 MHz, DMSO-d$_6$):—δ 1.66 (bm, 2H), 1.84 (bm, 4H), 2.04 (bm, 2H), 5.49 (bm, 1H), 7.75 (m, 4H), 8.41 (d, 2H, J=9.3 Hz), 8.48 (d, 1H, J=9.0 Hz), 9.01 (s, 1H).

Step IV—N9-(3,5-dichloro-4-pyridyl)-6-difluoromethoxy-3-cyclopentyl-4-oxo-3,4-dihydrobenzo[4,5]furo[2,3-d]pyridazine-9-carboxylate This compound was synthesized by the same procedure as described in step IV of example 28.
m.p.—above 250° C.
IR (KBr):—3433, 2926, 2363, 2170, 1672, 1490, 1399, 1280, 1200, 1089, 892, 816, 771 cm$^{-1}$.
$^1$H nmr (300 MHz, DMSO-d$_6$):—δ 1.65 (bm, 2H), 1.84 (bm, 4H), 2.05 (bm, 2H), 5.49 (bm, 1H), 7.62 (t, 1H, J=72.9 Hz), 7.77 (d, 1H, J=8.7 Hz), 8.16 (d, 1H, J=8.7 Hz), 8.82 (s, 2H), 8.85 (s, 1H), 11.21 (s, 1H).

In Vitro Studies

Inhibition of Phosphodiesterase Enzymes (PDE4)
In this assay, PDE4 enzyme converts [$^3$H] cAMP to the corresponding [$^3$H] 5'-AMP in proportion to the amount of PDE4 present. The [$^3$H] 5'-AMP then was quantitatively converted to free [$^3$H] adenosine and phosphate by the action of snake venom 5'-nucleotidase. Hence, the amount of [$^3$H] adenosine liberated is proportional to PDE4 activity.
The assay was performed with modification of the method of Thompson and Appleman (Biochemistry; 1971; 10; 311-316) and Schwartz and Passoneau (Proc. Natl. Acad. Sci. U.S.A. 1974; 71; 3844-3848), both references incorporated herein by reference in their entirety, at 34° C. In a 200 ul total reaction mixture, the reaction mixture contained 12.5 mM of Tris, 5 mM MgCl$_2$, 1 μM cAMP (cold) and $^3$H cAMP (0.1 uCi), (Amersham). Stock solutions of the compounds to be investigated were prepared in DMSO in concentrations such that the DMSO content in the test samples did not exceed 0.05% by volume to avoid affecting the PDE4 activity. Drug samples were then added in the reaction mixture (25 μl/tube). The assay was initiated by addition of enzyme mix (75 μl) and the mixture was incubated for 20 minutes at 34° C. The reaction was stopped by boiling the tubes for 2 mins at 100° C. in a water bath. After cooling on ice for 5 minutes and addition of 50 ug/reaction of 5'-nucleotidase snake venom from Crotalus atrox (Sigma) incubation was carried out again for 20 min. at 34° C. The unreacted substrate was separated from ($^3$H) Adenosine by addition of Dowex AG 1-X8 (Biorad Lab), (400 ul) which was prequilibrated (1:1:1) in water and ethanol. Reaction mixture was then thoroughly mixed, placed on ice for 15 minutes, vortexed and centrifuged at 14,000 r.p.m. for 2 mins. After centrifugation, a sample of the supernatant was taken and added in 24 well optiplates containing Scintillant (1 ml) and mixed well. The samples in the plates were then determined for radioactivity in a Top Counter and the PDE4 activity was estimated. PDE4 enzyme was present in quantities that yield <30% total hydrolysis of substrate (linear assay conditions).

Results were expressed as percent inhibition (IC$_{50}$) in nM concentrations. The IC$_{50}$ values were determined from the concentration curves by nonlinear regression analysis.

| Example No. | IC$_{50}$ (nM) |
| --- | --- |
| 01 | 1.375 |
| 02 | 493.8 |
| 03 | 0.73 |
| 04 | 3.41 |
| 05 | 4.15 |
| 06 | 34.27% at 1 μM |
| 07 | 416.2 |
| 08 | 31.75% at 1 μM |
| 09 | 1.75 |
| 10 | 27.74% at 1 μM |
| 11 | 177.3 |
| 12 | 48.79% at 1 μM |
| 13 | 20.99% at 1 μM |
| 14 | 3526 |
| 15 | 12.90% at 1 μM |
| 16 | 2275 |
| 17 | 33.67% at 1 μM |
| 18 | 4.08 |
| 19 | 7.53 |
| 20 | 17.45 |
| 21 | 20.45 |
| 22 | 34.54% at 1 μM |
| 23 | 0.25 |
| 24 | 0.02 |
| 25 | 3.99 |
| 26 | 2.69 |
| 27 | 2.42 |

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined in the appended claims.

All patents, patent applications, and non-patent publications cited in this specification are herein incorporated by reference to the same extent as if each individual patent, patent application, or publication was specifically and individually indicated to be incorporated herein by reference.

We claim:
1. A compound of the formula (1)

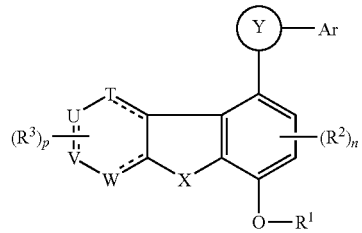

wherein:
R$^1$ is alkyl or alkyl substituted by one or more halogen groups;
R$^2$ is hydrogen;
R$^3$ is hydrogen;
Ar is a heteroaryl ring or a heteroaryl ring substituted by one or more halogen groups;
n is 2;
p is 3;

T, V and W are C;
U is N;
each dotted line [----] in the ring represents a bond;
X is O;
Y is —C(O)NR$^4$;
R$^4$ is hydrogen;
or a tautomer, stereoisomer, pharmaceutically acceptable salt or N-oxide thereof.

2. The compound according to claim 1 wherein R$^1$ is alkyl substituted by one or more halogen groups and Ar is heteroaryl substituted by one or more halogen groups.

3. The compound according to claim 1 wherein Ar is pyridyl, pyridyl substituted by one or more halogen groups, pyridyl-N-oxide or pyridyl-N-oxide substituted by one or more halogen groups.

4. The compound according to claim 3 wherein Ar is

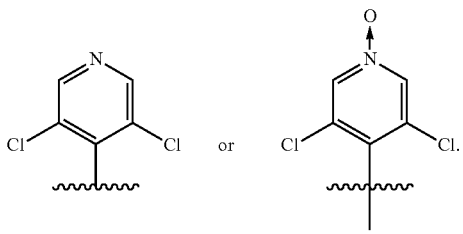

5. The compound according to claim 1, wherein R$^1$ is selected from —CH$_3$ and —CHF$_2$.

6. A compound according to claim 1, wherein the compound is 3,5-Dichloro-4-(6-difluoromethoxybenzo[4,5]furo[3,2-c]pyridin-9-ylcarboxamido)-1-pyridiniumolate.

7. A pharmaceutical composition comprising a compound according to claim 1 and at least one pharmaceutically acceptable excipient.

8. A compound having the formula

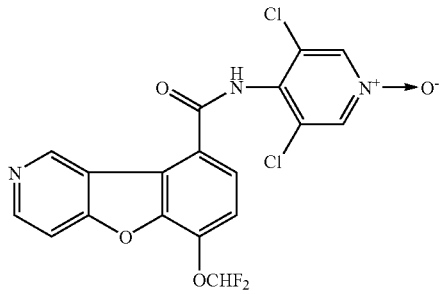

or a pharmaceutically acceptable salt thereof.

9. A compound according to claim 8, wherein the pharmaceutically acceptable salt is a sodium salt.

10. A pharmaceutical composition comprising a compound of claim 8 and at least one pharmaceutically acceptable excipient.

11. A compound having the formula

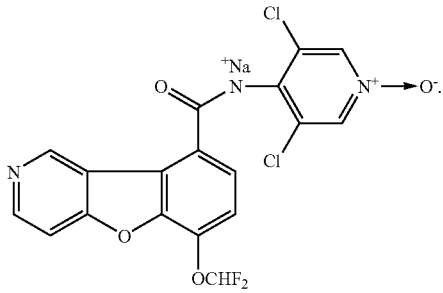

12. A pharmaceutical composition comprising a compound of claim 11 and at least one pharmaceutically acceptable excipient.

13. A compound selected from N9-(3,5-dichloro-4-pyridyl)-6-methoxybenzo[4,5]furo[3,2-c]pyridine-9-carboxamide, N9-(3,5-dichloro-4-pyridyl)-6-difluoromethoxybenzo[4,5]furo[3,2-c]pyridine-9-carboxamide, and pharmaceutically acceptable salts thereof.

14. The compound of claim 13, wherein the compound is N9-(3,5-dichloro-4-pyridyl)-6-difluoromethoxybenzo[4,5]furo[3,2-c]pyridine-9-carboxamide sodium.

15. A compound which is:
Methyl-1-hydroxy-6-methoxybenzo[4,5]furo[3,2-c]pyridine-9-carboxylate;
Methyl-1-chloro-6-methoxybenzo[4,5]furo[3,2-c]pyridine-9-carboxylate;
Methyl-6-methoxybenzo[4,5]furo[3,2-c]pyridine-9-carboxylate;
6-Methoxybenzo[4,5]furo[3,2-c]pyridine-9-carboxylic acid;
4-Nitrophenyl 6-methoxybenzo[4,5]furo[3,2-c]pyridine-9-carboxylate;
Methyl-1-hydroxy-6-cyclopentyloxybenzo[4,5]furo[3,2-c]pyridine-9-carboxylate;
Methyl-1-chloro-6-hydroxybenzo[4,5]furo[3,2-c]pyridine-9-carboxylate;
Methyl-1-chloro-6-difluoromethyloxybenzo[4,5]furo[3,2-c]pyridine-9-carboxylate;
Methyl-6-difluoromethyloxybenzo[4,5]furo[3,2-c]pyridine-9-carboxylate;
6-Difluoromethyloxybenzo[4,5]furo[3,2-c]pyridine-9-carboxylic acid;
4-Nitrophenyl 6-difluoromethyloxybenzo[4,5]furo[3,2-c]pyridine-9-carboxylate;
or a pharmaceutically acceptable salt thereof.

* * * * *